US008252829B2

(12) United States Patent
Duggan

(10) Patent No.: US 8,252,829 B2
(45) Date of Patent: Aug. 28, 2012

(54) AMINOPYRROLIDINONE DERIVATIVES AND USES THEREOF

(75) Inventor: Mark E. Duggan, Wellesley, MA (US)

(73) Assignee: Link Medicine Corporation, Cambridge, MA (US)

( * ) Notice: Subject to any disclaimer, the term of this patent is extended or adjusted under 35 U.S.C. 154(b) by 0 days.

(21) Appl. No.: 12/795,065

(22) Filed: Jun. 7, 2010

(65) Prior Publication Data

US 2011/0021590 A1 Jan. 27, 2011

Related U.S. Application Data

(60) Provisional application No. 61/184,386, filed on Jun. 5, 2009, provisional application No. 61/295,023, filed on Jan. 14, 2010.

(51) Int. Cl.
A61K 31/4178 (2006.01)
C07D 233/64 (2006.01)

(52) U.S. Cl. .................. 514/397; 548/311.4; 548/314.7; 548/335.5

(58) Field of Classification Search .................. 514/397; 548/314.7, 311.4, 335.5
See application file for complete search history.

(56) References Cited

U.S. PATENT DOCUMENTS

| 6,001,835 | A | 12/1999 | Dinsmore et al. |
| 6,063,930 | A | 5/2000 | Dinsmore et al. |
| 6,093,737 | A | 7/2000 | Anthony et al. |
| 7,285,565 | B2 | 10/2007 | Zhu et al. |
| 7,345,043 | B2 | 3/2008 | Anandan et al. |
| 2003/0191279 | A1 | 10/2003 | Goldstein et al. |
| 2005/0197336 | A1 | 9/2005 | Anandan et al. |
| 2007/0129437 | A1 | 6/2007 | Korodi |
| 2009/0012091 | A1 | 1/2009 | Yu |

FOREIGN PATENT DOCUMENTS

| EP | 1656931 A1 | 5/2006 |
| GB | 2450771 A | 1/2009 |
| JP | 2002275064 A | 9/2002 |
| JP | 2009051827 A | 3/2009 |
| JP | 2009051828 A | 3/2009 |
| WO | WO-89/12627 A1 | 12/1989 |
| WO | WO-91/12247 A1 | 8/1991 |
| WO | WO-92/20642 A1 | 11/1992 |
| WO | WO-93/02048 A1 | 2/1993 |
| WO | WO-96/18644 A1 | 6/1996 |
| WO | WO-96/36596 A1 | 11/1996 |
| WO | WO-97/30992 A1 | 8/1997 |
| WO | WO-97/36900 A1 | 10/1997 |
| WO | WO-98/16523 A2 | 4/1998 |
| WO | WO-98/28269 A1 | 7/1998 |
| WO | WO-98/57961 A1 | 12/1998 |
| WO | WO-99/50276 A1 | 10/1999 |
| WO | WO-00/18744 A1 | 4/2000 |
| WO | WO-00/51547 A2 | 9/2000 |
| WO | WO-01/05780 A1 | 1/2001 |
| WO | WO-01/17992 A1 | 3/2001 |
| WO | WO-01/18006 A1 | 3/2001 |
| WO | WO-01/19798 A2 | 3/2001 |
| WO | WO-01/27105 A1 | 4/2001 |
| WO | WO-01/74784 A1 | 10/2001 |
| WO | WO-02/00651 A2 | 1/2002 |
| WO | WO-02/080853 A2 | 10/2002 |
| WO | WO-03/004460 A2 | 1/2003 |
| WO | WO-03/057205 A2 | 7/2003 |
| WO | WO-2004/014370 A2 | 2/2004 |
| WO | WO-2004/014902 A2 | 2/2004 |
| WO | WO-2004/022523 A2 | 3/2004 |
| WO | WO-2004/026873 A1 | 4/2004 |
| WO | WO-2004/037817 A1 | 5/2004 |
| WO | WO-2005/012221 A1 | 2/2005 |
| WO | WO-2005/044797 A1 | 5/2005 |
| WO | WO-2005/077345 A1 | 8/2005 |
| WO | WO-2005/077368 A2 | 8/2005 |
| WO | WO-2005/077373 A2 | 8/2005 |
| WO | WO-2006/041831 A2 | 4/2006 |
| WO | WO-2006/063010 A2 | 6/2006 |
| WO | WO-2006/074262 A1 | 7/2006 |
| WO | WO-2006/084369 A1 | 8/2006 |
| WO | WO-2006/104280 A1 | 10/2006 |

(Continued)

OTHER PUBLICATIONS

C. W. Thornber, Chem. Soc. Rev. 1979, 8, 563-580.*
Appels et al., The Oncologist, 2005, 10, 565-578.*
F. Ferrara, Blood, 2009, 113, 4824-25.*
Schafer et al. Drug Discovery Today 2008, 13 (21/22), 913-916.*
Medicines in Development for Mental Illnesses 2010.*
Horig et al., Journal of Translational Medicine 2004, 2(44).*
Bell et al., "3-Aminopyrrolidinone Farnesyltransferase Inhibitors: Design of Macrocyclic Compounds with Improved Pharmacokinetics and Excellent Cell Potency",*J. Med. Chem.*, 45:2388-2409 (2002).
Bell et al., "3-Aminopyrrolidinone Farnesyltransferase Inhibitors: Design of Macrocyclic Compounds with Improved Pharmacokinetics and Excellent Cell Potency", *J. Med. Chem.*, 45:2388-2409 (2002) (Bell supporting information).
Bell et al., "Design and Biological Activity of (S)-4-(5-{[1-(3-Chlorobenzyl)-2-oxopyrrolidin-3-ylamino]methyl}imidazol-1-ylmethyl) benzonitrile, a 3-Aminopyrrolidinone Farnesyltransferase Inhibitor with Excellent Cell Potentcy", *Journal of Medicine Chemistry*, 44(18):2933-2949 (2001).

(Continued)

Primary Examiner — Jason M Nolan
(74) Attorney, Agent, or Firm — Mintz Levin Cohn Ferris Glovsky and Popeo, P.C.; Ivor R. Elrifi; Jennifer L. Loebach

(57) ABSTRACT

The present invention provides compounds of formula I:

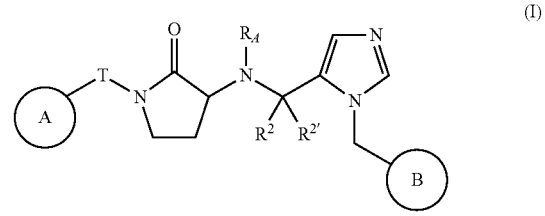

(I)

or a pharmaceutically acceptable salt thereof, wherein each of Ring A, Ring B, T, $R^2$, $R^{2'}$, and $R^A$ is as defined and described herein and methods for treating subjects or patients with a disease, disorder, or condition.

2 Claims, 2 Drawing Sheets

FOREIGN PATENT DOCUMENTS

| | | |
|---|---|---|
| WO | WO-2006/129199 A1 | 12/2006 |
| WO | WO-2007/015064 A1 | 2/2007 |
| WO | WO-2007/029121 A2 | 3/2007 |
| WO | WO-2007/070556 A2 | 6/2007 |
| WO | WO-2007/070600 A2 | 6/2007 |
| WO | WO-2007/088999 A1 | 8/2007 |
| WO | WO-2007/089857 A2 | 8/2007 |
| WO | WO-2007/100351 A2 | 9/2007 |
| WO | WO-2007/146712 A2 | 12/2007 |
| WO | WO-2008/002490 A2 | 1/2008 |
| WO | WO-2008/005262 A1 | 1/2008 |
| WO | WO-2008/061795 A2 | 5/2008 |
| WO | WO-2008/064218 A2 | 5/2008 |
| WO | WO-2008/091670 A2 | 7/2008 |
| WO | WO-2009/020677 A2 | 2/2009 |
| WO | WO-2009/049021 A1 | 4/2009 |
| WO | WO-2009/055331 A2 | 4/2009 |
| WO | WO-2009/065131 A1 | 5/2009 |
| WO | WO-2009/076337 A1 | 6/2009 |
| WO | WO-2009/096352 A1 | 8/2009 |

OTHER PUBLICATIONS

Puntambekar et al., "Insights into the structural requirements of farnesyltransferase inhibitors as potential anti-tumor agents based on 3D-QSAR CoMFA and CoMSIA models", *European Journal of Medicinal Chemistry*, 43(1):142-154 (2008).

Record from CAS Registry RN 1026428-61-4, Entered STN: Jun. 8, 2008.

Record from CAS Registry RN 1027012-05-0, Entered STN: Jun. 10, 2008.

* cited by examiner

AMINOPYRROLIDINONE DERIVATIVES AND USES THEREOF

RELATED APPLICATIONS

This patent application claims priority under 35 U.S.C. §119(e) to U.S. Provisional Patent Application Ser. Nos. 61/184,386, filed Jun. 5, 2009, and 61/295,023, filed Jan. 14, 2010, each of which is herein incorporated by reference in its entirety.

INCORPORATION OF SEQUENCE LISTING

The contents of the text file named "39823-517001US-3 ST25.txt", which was created on Sep. 30, 2010 and is 5KB in size, are hereby incorporated by reference in their entirety.

BACKGROUND

A variety of disorders are associated with abnormal protein folding and/or aggregation. For example, several neurodegenerative diseases and/or conditions associated with cognitive impairment are often characterized by intracellular and/or extracellular accumulation of specific proteins. To give but a couple of examples, Alzheimer's disease (AD) and Parkinson's Disease both involve abnormal protein folding and/or aggregation of specific proteins.

Pharmacologic treatment of neurodegenerative diseases such as Parkinson's disease and AD specifically, and of cognitive impairment and dementia more generally may be divided into three main areas: pharmacologic interventions targeting the specific underlying pathophysiology; pharmacological agents that ameliorate specific symptoms; and behavioral interventions. There remains a need for improved pharmacologic approaches in the treatment of neurodegenerative diseases.

SUMMARY

The present invention encompasses the finding that certain aminopyrrolidinone derivatives are useful in therapeutic and other applications, including those described herein. In certain embodiments, the invention provides a compound of formula

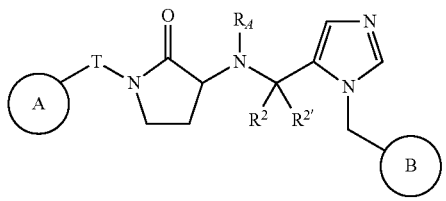

I or a pharmaceutically acceptable salt thereof, wherein

Ring A is C3-7 membered saturated or partially unsaturated carbocyclic ring, phenyl, a 5-6 membered monocyclic saturated, partially unsaturated or aromatic heterocyclic ring having 1-4 heteroatoms independently selected from nitrogen, oxygen, or sulfur, or an 8-10 membered bicyclic saturated, partially unsaturated or aromatic ring having 0-4 heteroatoms independently selected from nitrogen, oxygen, or sulfur, wherein Ring A is optionally substituted with 1-5 $R^1$ groups;

each $R^1$ is independently selected from —R, halogen, —OR, —CN, —NO$_2$, —SR, —S(O)R, —SO$_2$R, —C(O)R, —CO$_2$R, —OC(O)R, —C(O)N(R)$_2$, —OC(O)N(R)$_2$, —NRC(O)R, —NRC(O)N(R)$_2$, —NRSO$_2$R, —SO$_2$N(R)$_2$, —N(R)$_2$, —C(R)$_3$, —Si(CH$_3$)$_3$, or an optionally substituted group selected from phenyl, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur;

each R is independently hydrogen, deuterium, or an optionally substituted group selected from C$_{1-6}$ aliphatic, phenyl, a 5-6 membered monocyclic heteroaryl ring having 1-4 heteroatoms independently selected from nitrogen, oxygen, or sulfur, or an 8-10 membered bicyclic aryl ring having 0-4 heteroatoms independently selected from nitrogen, oxygen, or sulfur, or wherein:

two R on the same nitrogen are taken together to form a 5-6 membered saturated, partially saturated, or aromatic ring having 1-3 heteroatoms independently selected from nitrogen, oxygen, and sulfur;

$R_A$ is hydrogen, deuterium, or C$_{1-6}$ aliphatic;

T is a valence bond or a bivalent C$_{1-2}$ alkylene chain wherein T is optionally substituted with one or two R groups, and wherein two R groups on T are optionally taken together with their intervening atom(s) to form a 3-8-membered saturated monocyclic ring having 0-2 heteroatoms independently selected from nitrogen, oxygen, or sulfur;

each of $R^2$ and $R^{2'}$ is independently hydrogen, deuterium, halogen, or optionally substituted C$_{1-6}$ aliphatic;

Ring B is phenyl, a 5-6 membered monocyclic heteroaryl ring having 1-4 heteroatoms independently selected from nitrogen, oxygen, or sulfur, or an 8-10 membered bicyclic saturated, partially unsaturated or aromatic ring having 0-4 heteroatoms independently selected from nitrogen, oxygen, or sulfur, wherein Ring B is optionally substituted with 1-5 $R^3$ groups; and each $R^3$ is independently selected from —R, halogen, —OR, —CN, —NO$_2$, —SR, —S(O)R, —SO$_2$R, —SO$_2$N(R)$_2$, —C(O)R, —CO$_2$R, —OC(O)R, —OC(O)N(R)$_2$, —C(O)N(R)$_2$, —NRC(O)R, —NRC(O)N(R)$_2$, —NRSO$_2$R, —N(R)$_2$, —C(R)$_3$, —Si(CH$_3$)$_3$, or an optionally substituted group selected from phenyl, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur.

In certain embodiments, the invention provides a compound or pharmaceutically acceptable salt thereof, wherein Ring B is of the formula:

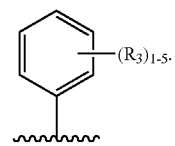

In certain embodiments, the invention provides a compound or pharmaceutically acceptable salt thereof, wherein at least one of $R^3$ is selected from the group consisting of R, halogen, —OR, —CN, and —N(R)$_2$.

In certain embodiments, the invention provides a compound or pharmaceutically acceptable salt thereof, wherein $R^3$ is CN.

In certain embodiments, the invention provides a compound or pharmaceutically acceptable salt thereof, wherein $R_4$ is hydrogen.

In certain embodiments, the invention provides a compound or pharmaceutically acceptable salt thereof, wherein $R^2$ and $R^{2'}$ are each hydrogen.

In certain embodiments, the invention provides a compound or pharmaceutically acceptable salt thereof, wherein Ring A is selected from the group consisting of phenyl, 6-membered monocyclic saturated or partially unsaturated or aromatic heterocyclic ring having 1-4 heteroatoms independently selected from nitrogen, oxygen, or sulfur, and a 10-membered bicyclic ring having 1-3 heteroatoms independently selected from nitrogen, oxygen, or sulfur, and each is optionally substituted with 1-5 $R^1$ groups.

In certain embodiments, the invention provides a compound or pharmaceutically acceptable salt thereof, wherein Ring A is selected from the group consisting of phenyl, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indaznlyl, henzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, chromanyl, naphthyl, or 1,2,3,4-tetrahydronaphthalenyl, wherein each ring is optionally substituted with 1-2 $R^1$ groups.

In certain embodiments, the invention provides a compound or pharmaceutically acceptable salt thereof, wherein Ring A is selected from the group consisting of phenyl, chromanyl, and 1,2,3,4-tetrahydronaphthalenyl.

In certain embodiments, the invention provides a compound or pharmaceutically acceptable salt thereof, wherein at least one $R^1$ is selected from the group consisting of R, halogen, —OR, —CN, —N(R)$_2$, —CF$_3$, —CHF$_2$, or CH$_3$.

In certain embodiments, the invention provides a compound or pharmaceutically acceptable salt thereof, wherein at least one $R^1$ is selected from halogen, $C_1$-$C_6$ aliphatic, —CN, —CHF$_2$, —CF$_3$, and phenyl.

In certain embodiments, the invention provides a compound or pharmaceutically acceptable salt thereof, wherein T is a valence bond or —CH$_2$—.

In certain embodiments, the invention provides a pharmaceutical composition comprising a compound of the invention or pharmaceutically acceptable salt thereof and a pharmaceutically acceptable excipient.

The present invention also provides methods of preparing such compounds and various compositions and uses of such compounds. In certain embodiments, the invention provides a method of treating a proteinopathic subject, wherein the method comprises administering to the subject a compound of the invention or a pharmaceutically acceptable salt thereof.

In certain embodiments, the invention provides a method, wherein the proteinopathic subject is suffering from a neurodegenerative disease, a cognitive impairment, dementia, depression, anxiety, a lysosomal storage disease, an ocular disease, an inflammatory disease, a cardiovascular disease, a proliferative disease, immunologic disease, a myopathy, diabetes, obesity, traumatic brain injury, an immunological disease or a mitochondrial disease.

In certain embodiments, the invention provides a method, wherein neurodegenerative disease is selected from Parkinson's disease, diffuse Lewy body disease, multiple system atrophy, pantothenate kinase-associated neurodegeneration, amyotrophic lateral sclerosis, Huntington's disease, and Alzheimer's disease.

In certain embodiments, the invention provides a method, wherein the proteinopathic subject is suffering from a mitochondrial disease, wherein decreased mitochondrial function is responsible, wholly, or in part, for the symptoms of the disease.

In certain embodiments, the invention provides a method, wherein the disease that the subject is suffering from is selected from MELAS, Leber syndrome, type 2 diabetes, Alzheimer's disease, Parkinson's disease, Crohn's disease, mitochondrial myopathy, progressive supranclear palsy, Lewy body disease, ALS (amyotophic lateral sclerosis/Lou Gehrig's disease), and Huntington's disease.

In certain embodiments, the invention provides a method, wherein the amount administered is an amount sufficient to improve mitochondrial health in the subject.

DETAILED DESCRIPTION

Figure 1:
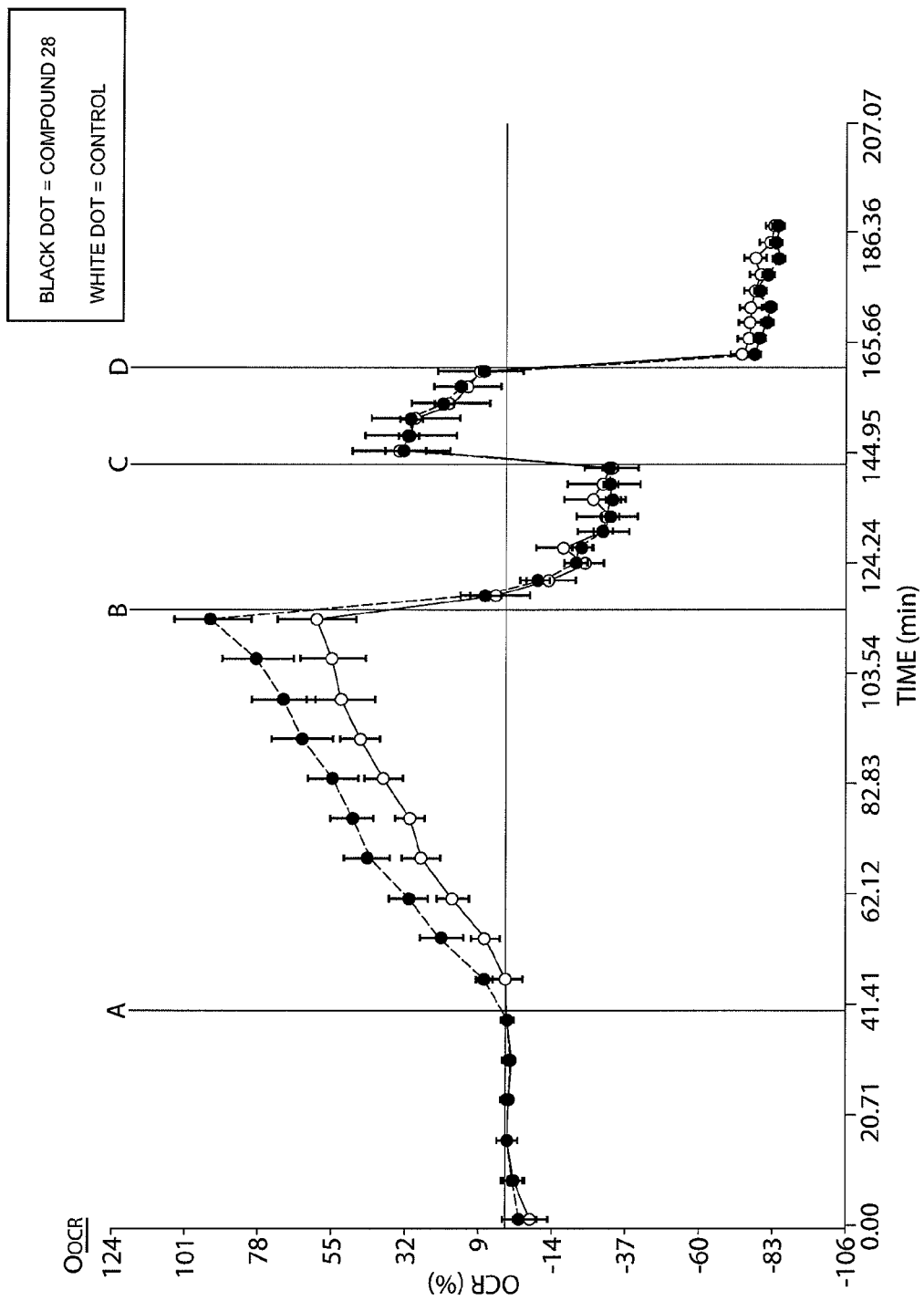
FIG. 1 is a graph that shows respiratory of compound 28 at 1 nM/2.5 days incubation; Oxygen Consumption Rate (OCR) vs. time (% of base line)(Avg). Compound 28 demonstrated a 50% increase in mitochondrial respiration.

1. General Description of Compounds of the Invention:

In certain embodiments, the present invention provides a compound of formula I:

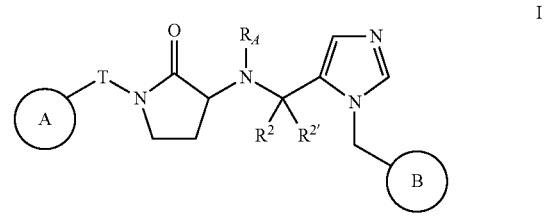

or a pharmaceutically acceptable salt thereof, wherein:

Ring A is $C_{3-7}$ membered saturated or partially unsaturated carbocyclic ring, phenyl, a 5 or 6 membered monocyclic saturated, partially unsaturated or aromatic heterocyclic ring having 1, 2, 3, or 4 heteroatoms independently selected from nitrogen, oxygen, or sulfur, or an 8, 9, or 10 membered bicyclic saturated, partially unsaturated or aromatic ring having 0, 1, 2, 3, or 4 heteroatoms independently selected from nitrogen, oxygen, or sulfur, wherein Ring A is optionally substituted with 1, 2, 3, 4, or 5 $R^1$ groups;

each $R^1$ is independently selected from —R, halogen, —OR, —CN, —NO$_2$, —SR, —S(O)R, —SO$_2$R, —C(O)R, —CO$_2$R, —OC(O)R, —C(O)N(R)$_2$, —OC(O)N(R)$_2$, —NRC(O)R, —NRC(O)N(R)$_2$, —NRSO$_2$R, —SO$_2$N(R)$_2$, —N(R)$_2$, —C(R)$_3$, —Si(CH$_3$)$_3$, or an optionally substituted group selected from phenyl, a 5 or 6 membered monocyclic heteroaryl ring having 1, 2, 3, or 4 heteroatoms independently selected from nitrogen, oxygen, or sulfur, or an 8, 9, or 10 membered bicyclic ring having 0, 1, 2, 3, or 4 heteroatoms independently selected from nitrogen, oxygen, or sulfur;

each R is independently hydrogen, deuterium, or an optionally substituted group selected from $C_{1-6}$ aliphatic, phenyl, a 5 or 6 membered monocyclic heteroaryl ring having 1, 2, 3, or 4 heteroatoms independently selected from nitrogen, oxygen, or sulfur, or an 8-10 membered bicyclic aryl ring having 0, 1, 2, 3, or 4 heteroatoms independently selected from nitrogen, oxygen, or sulfur, or wherein:
  two R on the same nitrogen are taken together to form a 5 or 6 membered saturated, partially saturated, or aromatic ring having 1, 2, or 3 heteroatoms independently selected from nitrogen, oxygen, and sulfur;
$R^4$ is hydrogen, deuterium, or $C_{1-6}$ aliphatic;
T is a valence bond or a bivalent $C_{1-2}$ alkylene chain wherein T is optionally substituted with one or two R groups, and wherein two R groups on T are optionally taken together with their intervening atom(s) to form a 3, 4, 5, 6, 7, or 8-membered saturated monocyclic ring having 0, 1, or 2 heteroatoms independently selected from nitrogen, oxygen, or sulfur;
each of $R^2$ and $R^{2'}$ is independently hydrogen, deuterium, halogen, or optionally substituted $C_{1-6}$ aliphatic, or wherein;
  $R^2$ and $R^{2'}$ are taken together to form a 5 or 6 membered saturated or partially saturated ring having 0, 1, 2, or 3 heteroaroms independently selected from nitrogen, oxygen, and sulfur;
Ring B is phenyl, a 5 or 6 membered monocyclic heteroaryl ring having 1, 2, 3, or 4 heteroatoms independently selected from nitrogen, oxygen, or sulfur, or an 8, 9, or 10 membered bicyclic saturated, partially unsaturated or aromatic ring having 0, 1, 2, 3, or 4 heteroatoms independently selected from nitrogen, oxygen, or sulfur, wherein Ring B is optionally substituted with 15 $R^3$ groups; and
each $R^3$ is independently selected from —R, halogen, —OR, —CN, —$NO_2$, —SR, —S(O)R, —$SO_2R$, —$SO_2N(R)_2$, —C(O)R, —$CO_2R$, —OC(O)R, —OC(O)N(R)$_2$, —C(O)N(R)$_2$, —NRC(O)R, —NRC(O)N(R)$_2$, —$NRSO_2R$, —N(R)$_2$, —C(R)$_3$, —Si(CH$_3$)$_3$, or an optionally substituted group selected from phenyl, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur.

2. Definitions:

As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

As used herein, the term "in vitro" refers to events that occur in an artificial environment, e.g., in a test tube or reaction vessel, in cell culture, etc., rather than within an organism (e.g., animal, plant, and/or microbe).

As used herein, the term "in vivo" refers to events that occur within an organism (e.g., animal, plant, and/or microbe).

As used herein, the term "nucleic acid", in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid", "DNA", "RNA", and/or similar terms include nucleic acid analogs, i.e., analogs having other than a phosphodiester backbone. For example, the so-called "peptide nucleic acids", which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, at least 4, at least 5, at least 6, at least 7, at least 8, at least 9, at least 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids", meaning nucleic acids (e.g., polynucleotides and residues, including nucleotides and/or nucleosides) that have not been chemically modified in order to facilitate or achieve delivery.

As used herein, the term "patient" or "subject" refers to any organism to which a composition of this invention may be administered, e.g., for experimental, diagnostic, prophylactic, and/or therapeutic purposes. Typical subjects include animals (e.g., mammals such as mice, rats, rabbits, non-human primates, and humans; insects; worms; etc.). In some embodiments, a subject may be infected with, suffering from, and/or susceptible to a disease, disorder, and/or condition, and/or may be of normal genotype, or have one or more engineered transgenes inserted in their genome.

As used herein, the term "proteinopathic subject" refers to a subject that is diagnosed with or affected by, or at risk of developing a proteinopathy (e.g., predisposed, for example genetically predisposed, to developing a proteinopathy) including any disorder characterized by abnormal protein metabolism or accumulation. The term "subject with a proteinopathy" refers to a subject that is diagnosed with or affected by a proteinopathy, including any disorder characterized by abnormal protein metabolism or accumulation. The term "subject at risk of developing a proteinopathy" refers to a person that is predisposed, for example genetically predisposed, to developing a proteinopathy) and/or any disorder characterized by abnormal protein metabolism or accumulation. Proteinopathy includes neurodegenerative diseases, cognitive impairment, depression, anxiety, lysosomal storage diseases, immunologic diseases, inflammatory diseases, cardiovascular diseases, myopathy, diabetes, obesity, mitochondrial diseases, ocular diseases, traumatic brain injury, and some proliferative diseases. In one aspect of the invention, the proteinopathic subject is a subject with a mitochondrial disorder. Proteinopathic subjects can be readily identified by persons of ordinary skill in the art by symptomatic diagnosis and neurologic examination and/or in some instances in conjunction with genetic screening, brain scans, SPEC, PET imaging, etc.

In the methods of the invention, the term "proteinopathy" includes neurodegenerative diseases including Parkinson's Disease, diffuse Lewy body disease, multiple system atrophy (MSA—the nomenclature initially included three distinct terms: Shy-Drager syndrome, striatonigral degeneration (SD), and olivopontocerebellar atrophy (OPCA)), pantothenate kinase-associated neurodegeneration (e.g., PANK1), cognitive impairment, dementia, amyotrophic lateral sclerosis (ALS), Huntington's Disease (HD), and Alzheimer's Disease (AD) and includes other abnormal protein metabolism or accumulation implicated in other pathological disorders such as depression, anxiety, lysosomal storage disease, immune disease, mitochondrial disease, ocular disease, inflammatory disease, cardiovascular disease, proliferative disease, myopathy, diabetes, and obesity.

As used herein, the term "synucleinopathic subject" or "subject with a synucleinopathy" refers to a subject that is diagnosed with, affected by, or at risk of developing a synucleinopathy (e.g., predisposed or susceptible, for example genetically predisposed, to developing a synucleinopathy) and/or any neurodegenerative disorder characterized by pathological synuclein aggregations. Several neurodegenerative disorders including Parkinson's disease (PD), diffuse Lewy body disease (DLBD), and multiple system atrophy (MSA) are collectively grouped as synucleinopathies. Subjects suffering from or susceptible to synucleinopathies can be readily identified by persons of ordinary skill in the art by symptomatic diagnosis and neurologic examination and/or in some instances in conjunction with genetic screening, brain scans, SPEC, PET imaging, etc.

The term "synucleionopathy" is used herein to refer to diseases, disorders, or conditions that are associated with or characterized by pathological accumulation of α-synuclein. According to the present invention, disorders such as (but not limited to) PD, DLBD, and MSA are considered to be synucleinopathies.

As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence) or can be a portion, e.g., a characteristic portion, thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof. As used herein, the term "proteinopathy" refers to diseases, disorders, and/or conditions associated with the pathogenic accumulation and/or aggregation of one or more types of proteins (for example, but not limited to e.g., α-synuclein, amyloid beta proteins, and/or tau proteins). In some embodiments, a proteinopathy may involve alterations in one or more of protein folding, degradation (e.g., autophagy) transportation, etc. Some proteinopathies may be neurodegenerative diseases, some may be inflammatory diseases, some may be cardiovascular diseases, some may be proliferative diseases, etc. Included under the umbrella definition of proteinopathies are such specific pathologies as synucleinopathies, tauopathies, amyloidopathies, TDP-43 proteinopathies and others. In some embodiments, the proteinopathy is selected from the group consisting of atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia. Exemplary proteins involved in proteinopathies include: α-synuclein in the case of PD, Lewy body disease, and other synucleinopathies; Tau and Aβ in the case of AD and certain other neurodegenerative diseases; SOD1 and TDP-43 in the case of ALS; huntingtin in the case of Huntington's disease, rhodopsin in the case of retinitis pigmentosa, and a number of proteins in the case of the diseases collectively known as lysosomal storage disease. Indeed, in lysosomal storage diseasess, there is often an accumulation of certain lipids eg glucosylceramide or cholesterol, or of certain proteins (e.g., subunit c of ATP synthase), or of certain damaged organelles or organelle fragments eg fragmented mitochondria. In some embodiments, the proteinopathy is a synucleinopathy.

In some embodiments, the proteinopathy is an amyloidopathy. The present invention provides methods relevant to amyloidopathies. For example, in some embodiments, the present invention provides a method of reducing amyloid beta toxicity in a cell, the method comprising administering to a cell a therapeutically effective amount of a provided compound. In some embodiments, the present invention provides a method of reducing the accumulation of amyloid beta proteins in a cell, the method comprising administering to a cell a therapeutically effective amount of a provided compound. In some embodiments, the cell is a neuronal cell. In some embodiments, the cell expresses amyloid beta proteins. In some embodiments, the present invention provides a method of reducing amyloid beta toxicity in the brain, the method comprising administering to a human a therapeutically effective amount of a provided compound. In some embodiments, the present invention provides a method of reducing the accumulation of amyloid beta proteins in the brain, the method comprising administering to a human a therapeutically effective amount of a provided compound. In certain embodiments, the amyloidopathy is Alzheimer's disease.

In some embodiments, the amyloidopathy is selected from the group consisting of atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia. In some embodiments, the amyloidopathy is Alzheimer's disease. In some embodiments, the amyloidopathy is vascular dementia. In some embodiments, the amyloidopathy is cognitive impairment.

In some embodiments, the proteinopathy is taupathy. The present invention provides methods related to taupathies. Taupathies are neurodegenerative disorders characterized by the presence of filamentous deposits, consisting of hyperphosphorylated tau protein, in neurons and glia. Abnormal tau phosphorylation and deposition in neurons and glial cells is one of the major features in taupathies. The term tauopathy, was first used to describe a family with frontotemporal dementia (FTD) and abundant tau deposits. This term is now used to identify a group of diseases with widespread tau pathology in which tau accumulation appears to be directly associated with pathogenesis. Major neurodegenerative taupathies includes sporadic and hereditary diseases characterized by filamentous tau deposits in brain and spinal cord.

In the majority of taupathies, glial and neuronal tau inclusions are the sole or predominant CNS lesions. Exemplary such taupathies include amytrophic lateral sclerosis (ALS), parkinsonism, argyrophilic grain dementia, diffuse neurofibrillary tangles with calcification, frontotemporal dementia linked to chromosome 17, corticobasal degeneration, Pick's disease, progressive supranuclear palsy, progressive subcortical gliosis, and tangle only dementia.

In some embodiments, the taupathy is selected from the group consisting of atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia. In some embodiments, the taupathy is Alzheimer's disease.

In general, a "small molecule" is understood in the art to be an organic molecule that is less than about 2000 g/mol in size. In some embodiments, the small molecule is less than about 1500 g/mol or less than about 1000 g/mol. In some embodiments, the small molecule is less than about 800 g/mol or less than about 500 g/mol. In some embodiments, small molecules are non-polymeric and/or non-oligomeric. In some embodiments, small molecules are not proteins, peptides, or amino acids. In some embodiments, small molecules are not nucleic acids or nucleotides. In some embodiments, small molecules are not saccharides or polysaccharides.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

An individual who is "suffering from" a disease, disorder, and/or condition has been diagnosed with and/or displays one or more symptoms of a disease, disorder, and/or condition.

An individual who is "susceptible to" a disease, disorder, and/or condition typically has not been diagnosed with a disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition. In some embodiments, an individual is considered to be susceptible to a particular disease, disorder, and/or condition because that individual is determined to have an increased risk of developing the disease, disorder, or condition than is observed in the general population.

As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

As used herein, the term "therapeutically effective amount" means an amount of a substance (e.g., a therapeutic agent, composition, and/or formulation) that elicits a desired biological response. In some embodiments, a therapeutically effective amount of a substance is an amount that is sufficient, when administered to a subject suffering from or susceptible to a disease, disorder, and/or condition, to treat, diagnose, prevent, and/or delay and/or alleviate one or more symptoms of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a formulation to treat a disease, disorder, and/or condition is the amount that alleviates, ameliorates, relieves, inhibits, prevents, delays onset of; reduces severity of and/or reduces incidence of one or more symptoms or features of the disease, disorder, and/or condition. Furthermore, an effective amount may be administered via a single dose or via multiple doses within a treatment regimen. In some embodiments, individual doses or compositions are considered to contain a "therapeutically effective amount" when they contain an amount effective as a dose in the context of a treatment regimen. Those of ordinary skill in the art will appreciate that a dose or amount may be considered to be effective if it is or has been demonstrated to show statistically significant effectiveness when administered to a population of patients; a particular result need not be achieved in a particular individual patient in order for an amount to be considered to be therapeutically effective as described herein.

As used herein, the term "treat", "treatment", or "treating" refers to any method used to partially or completely alleviate, ameliorate, relieve, inhibit, delay onset of, reduce severity of and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition. As used herein, "preventing" means causing the clinical symptoms of the disease state not to develop i.e., inhibiting the onset of disease, in a subject that may be exposed to or predisposed to the disease state, but does not yet experience or display symptoms of the disease state.

The term "stereochemically isomeric forms" of compounds, as used herein, include all possible compounds made up of the same atoms bonded by the same sequence of bonds but having different three-dimensional structures which are not interchangeable, which the compounds may possess. The present invention encompasses each and every stereochemically isomeric form of a designated compound. Furthermore, the present invention encompasses all such stereochemically isomeric forms (e.g., all diastereomers and/or enantiomers) in pure form and/or in any combination with one another, including in racemic mixtures.

Some of the compounds provided herein may exist in tautomeric forms. Such forms are encompassed by the present invention, whether or not explicitly depicted in displayed chemical formulas.

Compounds of the present invention may be provided in the form of "prodrugs", as is known in the art. For examples of common known prodrug derivatives, see:
  a) Design of Prodrugs, edited by H. Bundgaard, (Elsevier, 1985) and *Methods in Enzymology*, 42:309-396, edited by K. Widder, et al. (Academic Press, 1985);
  b) A Textbook of Drug Design and Development, edited by Krogsgaard-Larsen;
  c) Bundgaard, Chapter 5 "Design and Application of Prodrugs", by H. Bundgaard, p. 113-191 (1991);
  d) H. Bundgaard, *Advanced Drug Delivery Reviews*, 8:1-38 (1992);
  e) H. Bundgaard, et al., *Journal of Pharmaceutical Sciences*, 77:285 (1988); and
  f) N. Kakeya, et al., *Chem. Pharm. Bull.*, 32:692 (1984).

The methods and structures described herein relating to compounds of the invention may be applied to, for example, pharmaceutically acceptable acid or base addition salts, prodrugs, tautomeric forms, and/or stereoisomerric forms of described compounds.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkylene" refers to a saturated bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, chromanyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein, the term "valence" is defined as the maximum number of univalent atoms (originally hydrogen or chlorine atoms) that may combine with an atom of the element under consideration, or with a fragment, or for which an atom of this element can be substituted. Thus, the term "monovalent" as used herein refers to an atom or fragment that may combine with one other atom or fragment. The term "bivalent" as used herein refers to an atom or fragment that may combine with two other atoms or fragments.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium (herein denoted as 'D'), halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S) R$^\circ$; —(CH$_2$)$_{0-4}$N(R$^\circ$)C(O)NR$^\circ_2$; —N(R$^\circ$)C(S)NR$^\circ_2$; —(CH$_2$)$_{0-4}$N(R$^\circ$)C(O)OR$^\circ$; —N(R$^\circ$)N(R$^\circ$)C(O)R$^\circ$; —N(R$^\circ$) N(R$^\circ$)C(O)NR$^\circ_2$; —N(R$^\circ$)N(R$^\circ$)C(O)OR$^\circ$; —(CH$_2$)$_{0-4}$C(O) R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ_3$; —(CH$_2$)$_{0-4}$OC(O)R$^\circ$; —OC(O) (CH$_2$)$_{0-4}$SR—, SC(S)SR$^\circ$; —(CH$_2$)$_{0-4}$SC(O)R$^\circ$; —(CH$_2$)$_{0-4}$ C(O)NR$^\circ_2$; —C(S)NR$^\circ_2$; —C(S)SR$^\circ$; —SC(S)SR$^\circ$, —(CH$_2$)$_{0-4}$OC(O)NR$^\circ_2$; —C(O)N(OR$^\circ$)R$^\circ$; —C(O)C(O) R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS (O)$_2$R$^\circ$; —S(O)$_2$NR$^\circ_2$; —(CH$_2$)$_{0-4}$S(O)R$^\circ$; —N(R$^\circ$)S(O)$_2$ NR$^\circ_2$; N(R$^\circ$)S(O)$_2$R$^\circ$; —N(OR$^\circ$)R$^\circ$; —C(NH)NR$^\circ_2$; —P(O)$_2$R$^\circ$; —P(O)R$^\circ_2$; —OP(O)R$^\circ_2$; —OP(O)(OR$^\circ$)$_2$; SiR$^\circ_3$; —(C$_{1-4}$ straight or branched)alkylene)O—N(R$^\circ$)$_2$; or —(C$_{1-4}$ straight or branched) alkylene)C(O)O—N(R$^\circ$)$_2$, wherein each R$^\circ$ may be substituted as defined below and is independently hydrogen, deuterium, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently hydrogen, deuterium, halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR$^*_2$, =NNHC(O)R*, =NNHC(O)OR*, =NNHS(O)$_2$R*, —NR*, =NOR*, —O(C(R$^*_2$))$_{2-3}$O—, or —S(C(R$^*_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR$^*_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O) R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "protecting group", as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3 (p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fern), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pane), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pine), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl 5,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethyl idene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Certain provided compounds may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. In certain embodiments, the present invention relates to a compound represented by any of the structures outlined herein, wherein the compound is a single stereoisomer.

Contemplated equivalents of compounds described herein include compounds which otherwise correspond thereto, and which have the same general properties thereof, wherein one or more simple variations of substituents are made which do not adversely affect the efficacy of the compound. In general, provided compounds may be prepared by the methods illustrated in the general reaction schemes as, for example, described below, or by modifications thereof, using readily available starting materials, reagents and conventional synthesis procedures: In these reactions, it is also possible to make use of variants, which are in themselves known, but are not mentioned here.

For purposes of this invention, the chemical elements are identified in accordance with the Periodic Table of the Elements, CAS version, *Handbook of Chemistry and Physics*, 67th Ed., 1986-87, inside cover.

In one aspect, the present invention provides a pharmaceutical composition comprising one or more of the compounds described herein and a pharmaceutically acceptable carrier. In another aspect, the present invention provides pharmaceutical compositions, which comprise a therapeutically effective amount of one or more compounds described herein, formulated together with one or more pharmaceutically acceptable carriers (additives) and/or diluents. As described in detail herein, pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As set out herein, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect refers to the relatively non-toxic, inorganic and organic acid addition salts of provided compounds. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. See, for example, Berge et al. (1977) "Pharmaceutical Salts", *J. Pharm. Sci.* 66:1-19; incorporated herein by reference.

Pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the provided compounds may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of provided compounds. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically-acceptable organic primary, secondary or tertiary amine. Appropriate base salt forms include, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. See, for example, Berge et al., supra. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

The phrases "systemic administration", "administered systemically", "peripheral administration", and "administered peripherally" as used herein mean the administration of a compound, drug or other material other than directly into the central nervous system, such that it enters the patient's system and, thus, is subject to metabolism and other like processes, for example, subcutaneous administration.

As used herein, the term "subject with cognitive impairment" refers to a subject that is diagnosed with, affected by, or at risk of developing cognitive impairment. The cognitive impairment may stem from any etiology. Exemplary causes of cognitive impairment include neurodegenerative diseases, neurological diseases, psychiatric disorders, genetic diseases, infectious diseases, metabolic diseases, cardiovascular diseases, vascular diseases, aging, trauma, malnutrition, childhood diseases, chemotherapy, auto immune diseases, and inflammatory diseases. Particular disease that are associated with cognitive impairment include, but are not limited to, atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Crcutzfeldt-Jakob disease), Fragile X syndrome, phenylketonuria, malnutrition, neurofibromatosis, maple syrup urine disease, hypercalcemia, hypothyroidism, hypercalcemia, and hypoglycemia. The degree of cognitive impairment may be assessed by a health care professional. A variety of standardized test are available for assessing cognition, including, but not limited to, the Mini-Mental Status Examination, the Dementia Symptom Assessmant Scale, and the ADAS. Such tests typically provide a measurable score of congnitive impairment.

As used herein, the term "subject with depression" refers to a subject that is diagnosed with, affected by, or at risk of developing depression.

As used herein, the term "subject with anxiety" refers to a subject that is diagnosed with, affected by, or at risk of developing anxiety. The anxiety may stein from a variety of causes. Based on mouse studies, farnesyl transferase inhibitors may be used as anxiolytics.

The term "lipotoxicity" as used herein refers to exposure to high concentrations of fatty acids.

The term "glucotoxicity" as used herein refers to exposure to high concentrations of glucose.

The term "glucolipotoxicity" as used herein refers to exposure to the combination of both high glucose and high lipids.

As used herein, the term "autophagic flux" refers to autophagic turnover i.e., the rate of formation and clearance of autophagosomes (APs) cells.

As used herein, the term "stimulate mitophagy" means that the mitochondrial clearance process is stimulated resulting in the production of new fully functional mitochondria. In one aspect, a stimulation of mitophagy increases net mitochondrial function.

As used herein, the term "subject with a mitochondrial disorder" refers to a subject that it suffering from a disease or disorder, wherein decreased mitochondrial function is responsible, wholly or in part, for its symptoms. The term "subject with a mitochondrial disorder" refers to a subject that is diagnosed with or affected by a mitochondrial disorder. The term "subject at risk of developing a mitochondrial disorder" refers to a person that is predisposed, for example, genetically predisposed, to developing a mitochondrial disorder. Mitochondrial disorders include for example, MELAS, Leber syndrome, type 2 diabetes, Alzheimer's disease, Parkinson's disease, Crohn's disease, myopathies (e.g. inclusion body myositis), progressive supranuclear palsy (PSP), Lewy Body Disease (LBD), ALS (amyotophic lateral sclerosis/Lou Gehrig's disease), Huntington's disease and other mitochondrial disorders disclosed herein.

3. Description of Exemplary Compounds:

In certain embodiments, Ring A is phenyl substituted with 1-5 $R^1$ groups. In certain embodiments, Ring A is unsubstituted phenyl.

In certain embodiments, Ring A is a $C_{3-7}$ membered saturated or partially unsaturated carbocyclic ring. In some embodiments, Ring A is cyclopropyl. In other embodiments, Ring A is cyclopentyl or cyclohexyl.

In certain embodiments, Ring A is naphthyl substituted with 1-5 $R^1$ groups. In certain embodiments, Ring A is unsubstituted naphthyl. In some embodiments, Ring A is 1,2,3,4-tetrahydronaphthyl.

In some embodiments, Ring A is a 5-6 membered monocyclic saturated, partially unsaturated or aromatic heterocyclic ring having 1-4 heteroatoms independently selected from nitrogen, oxygen, or sulfur, and optionally substituted with 1-5 $R^1$ groups. In some embodiments, Ring A is a 5 membered monocyclic heteroaryl ring having 1-3 heteroatoms independently selected from nitrogen, oxygen, or sulfur, and optionally substituted with 1-2 $R^1$ groups. In other embodiments, Ring A is a 6 membered monocyclic heteroaryl ring having 1-2 nitrogens independently selected from nitrogen, oxygen, or sulfur, and optionally substituted with 1-2 $R^1$ groups.

In certain embodiments, Ring A is an 8-10 membered bicyclic ring having 0-4 heteroatoms independently selected from nitrogen, oxygen, or sulfur, and optionally substituted with 1-5 $R^1$ groups. In some embodiments, Ring A is an 8 membered bicyclic ring having 1-3 heteroatoms independently selected from nitrogen, oxygen, or sulfur, and optionally substituted with 1-3 $R^1$ groups. In some embodiments, Ring A is a 9 membered bicyclic ring having 1-3 heteroatoms independently selected from nitrogen, oxygen, or sulfur, and optionally substituted with 1-3 $R^1$ groups. In some embodiments, Ring A is a 10 membered bicyclic ring having 1-3 heteroatoms independently selected from nitrogen, oxygen, or sulfur, and optionally substituted with 1-3 $R^1$ groups. In some embodiments, Ring A is an 8-10 membered bicyclic ring comprised of 0-2 aromatic rings and optionally substituted with 1-5 $R^1$ groups.

Exemplary Ring A heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one, or chromanyl, wherein each ring is optionally substituted with 1-2 $R^1$ groups.

In some embodiments, Ring A is of the following formula:

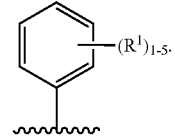

In some embodiments, Ring A is of any of the following formulae:

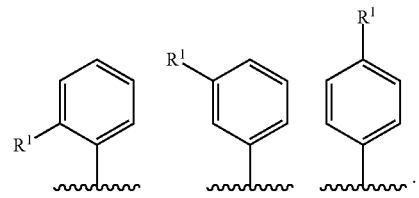

In some embodiments, Ring A is of any of the following formulae:
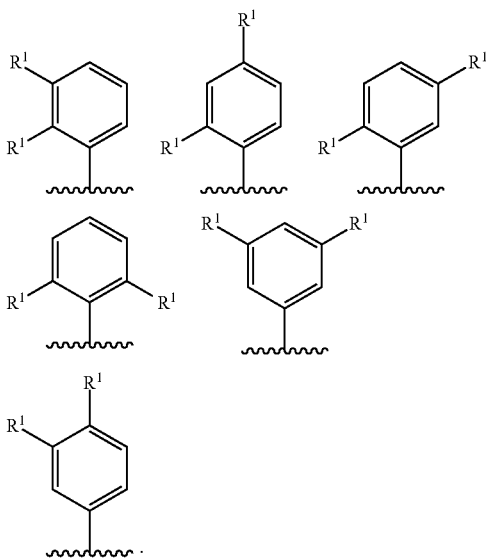
In some embodiments, Ring A is of any of the following formulae:
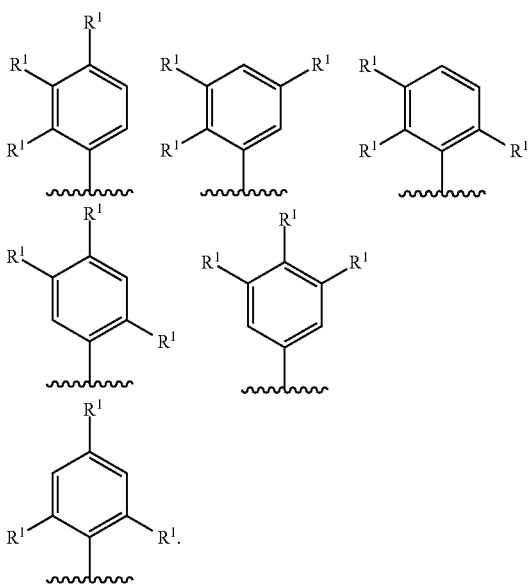
In some embodiments, Ring A is of any of the following formulae:
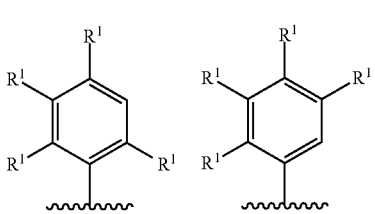
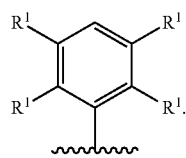
In some embodiments, Ring A is:
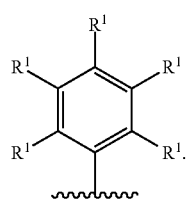
In certain embodiments, Ring A is:
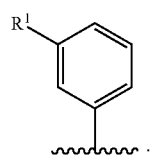
In certain embodiments, Ring A is:
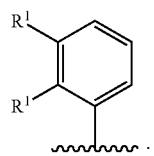
In certain embodiments, Ring A is:
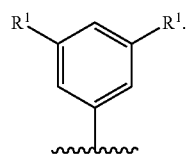
In certain embodiments, Ring A is:
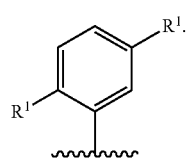

In certain embodiments, Ring A is any of the following moieties:

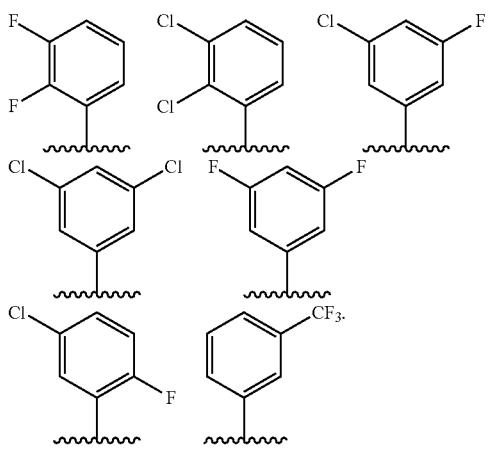

In certain embodiments, Ring A is any of the following moieties:

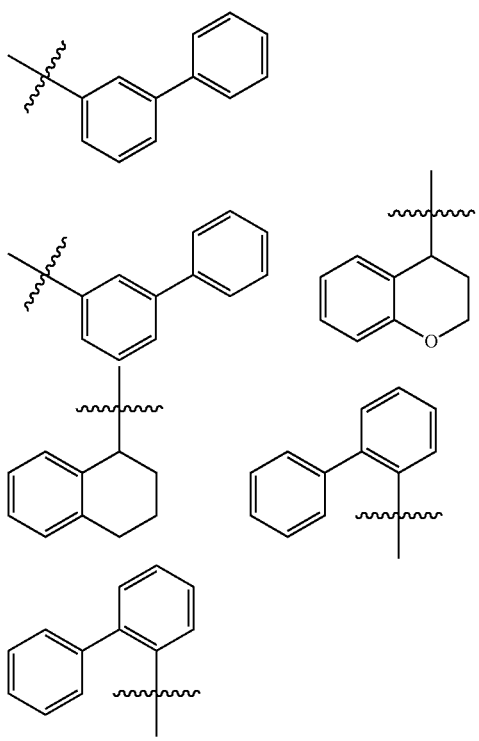

As defined above, each $R^1$ is independently selected from —R, halogen, —OR, —CN, —NO₂, —SR, —S(O)R, —SO₂R, —C(O)R, —CO₂R, —OC(O)R, —C(O)N(R)₂, —OC(O)N(R)₂, —NRC(O)R, —NRC(O)N(R)₂, —NRSO₂R, —SO₂N(R)₂, —N(R)₂, —C(R)₃, —Si(CH₃)₃, or an optionally substituted group selected from phenyl, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur. In some embodiments, each $R^1$ is independently R, halogen, —OR, —CN, or —N(R)₂. In some embodiments, each $R^1$ is independently R, halogen, —OR, or —CN. In some embodiments, each $R^1$ is independently selected from hydrogen, deuterium, methyl, ethyl, propyl, butyl, pentyl, hexyl, —CF₃, —CF₂H, —CFH₂, —CF₂CF₃, —CFHCF₃, —CH₂CF₃, —CF₂CF₂H, —CF₂CFH₂, —CF₂CH₃, —CFHCF₂H, —CFHCFH₂, and —CFHCH₃.

In some embodiments, at least one $R^1$ is selected from the group consisting of R, halogen, —OR, —CN, N(R)₂, —CF₃, —CHF₂ and —CH₃.

In some embodiments, at least one $R^1$ is selected from the group consisting of hydrogen, methyl, ethyl, propyl, and butyl.

In some embodiments, at least one $R^1$ is —OR, wherein R is independently selected from hydrogen, methyl, ethyl, propyl, —CF₃, —CF₂H, and —CF₂CF₃.

In some embodiments, each $R^1$ is independently selected from F, Cl, Br, and I. In some embodiments each $R^1$ is independently selected from F and Cl. In some embodiments, each $R^1$ is F. In some embodiments, each $R^1$ is Cl.

In some embodiments, each $R^1$ is independently —OR, wherein R is independently selected from hydrogen, methyl, ethyl, propyl, —CF₃, —CF₂H, —CFH₂, —CF₂CF₃, —CFHCF₃, —CH₂CF₃, —CF₂CF₂H, —CF₂CFH₂, —CF₂CH₃, —CFHCF₂H, —CFHCFH₂, or —CFHCH₃.

In certain embodiments, $R^1$ is substituted phenyl. In certain embodiments, $R^1$ is unsubstituted phenyl.

In certain embodiments, $R^1$ is substituted naphthyl. In certain embodiments, $R^1$ is unsubstituted naphthyl.

In some embodiments, $R^1$ is an optionally substituted 5-6 membered monocyclic heteroaryl ring having 1-4 heteroatoms independently selected from nitrogen, oxygen, or sulfur. In some embodiments, $R^1$ is an optionally substituted 5 membered monocyclic heteroaryl ring having 1-3 heteroatoms independently selected from nitrogen, oxygen, or sulfur. In other embodiments, $R^1$ is an optionally substituted 6 membered monocyclic heteroaryl ring having 1-2 nitrogens independently selected from nitrogen, oxygen, or sulfur.

In certain embodiments, $R^1$ is an optionally substituted 8-10 membered bicyclic ring having 0-4 heteroatoms independently selected from nitrogen, oxygen, or sulfur. In some embodiments, $R^1$ is an optionally substituted 8 membered bicyclic ring having 1-3 heteroatoms independently selected from nitrogen, oxygen, or sulfur. In some embodiments, $R^1$ is an optionally substituted 9 membered bicyclic ring having 1-3 heteroatoms independently selected from nitrogen, oxygen, or sulfur. In some embodiments, $R^1$ is an optionally substituted 10 membered bicyclic ring having 1-3 heteroatoms independently selected from nitrogen, oxygen, or sulfur. In some embodiments, $R^1$ is an optionally substituted 8-10 membered bicyclic ring comprised of 0-2 aromatic rings.

Exemplary optionally substituted $R^1$ heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, or chromanyl.

In some embodiments, each $R^1$ is independently —N(R)₂, wherein each R is independently hydrogen, methyl or ethyl. In some embodiments, two R on the same nitrogen are taken together to form a 5-6 membered saturated, partially saturated, or aromatic ring having 1-3 heteroatoms independently selected from nitrogen, oxygen, and sulfur. In some embodiments, two R on the same nitrogen are taken together to form a 5 membered saturated, partially saturated, or aromatic ring having 1-3 heteroatoms independently selected from nitrogen, oxygen, and sulfur. In some embodiments, two R on the same nitrogen are taken together to form a 6 membered saturated, partially saturated, or aromatic ring having 1-3 heteroatoms independently selected from nitrogen, oxygen, and sulfur.

In some embodiments, each $R^1$ is independently —SR, —S(O)R, or —$SO_2R$ wherein each R is independently hydrogen, methyl, ethyl, or propyl.

In some embodiments, each $R^1$ is independently —C(O)R or —$CO_2R$, wherein each R is independently hydrogen, methyl, ethyl, propyl, or trifluoromethyl.

In some embodiments, each $R^1$ is independently —C(O)R or —$CO_2R$, wherein each R is independently hydrogen, methyl, ethyl, or propyl.

In some embodiments, each $R^1$ is independently —C(O)N($R$)$_2$, —NRC(O)R, —NRC(O)N($R$)$_2$, or —$NRSO_2R$, wherein each R is independently hydrogen, methyl, ethyl, or propyl. In certain embodiments, $R^1$ is —$NHSO_2R$.

In some embodiments, each $R^1$ is independently selected from —$CF_3$, —$CF_2H$, —$CFH_2$, —$CF_2CF_3$, —$CFHCF_3$, —$CH_2CF_3$, —$CF_2CF_2H$, —$CF_2CFH_2$, —$CF_2CH_3$, —$CFHCF_2H$, —$CFHCFH_2$, and —$CFHCH_3$.

In some embodiments, $R_A$ is selected from hydrogen, deuterium, or $C_{1-6}$ aliphatic. In some embodiments, $R_A$ is hydrogen.

As defined generally above, T is a valence bond or a bivalent $C_{1-2}$ alkylene chain wherein T is optionally substituted with one or two R groups, and wherein two R groups on T are optionally taken together with their intervening atom(s) form a 3-8 membered saturated monocyclic ring having 0-2 heteroatoms independently selected from nitrogen, oxygen, or sulfur.

In some embodiments, T is a valence bond.

In other embodiments, T is a bivalent $C_{1-2}$ alkylene chain optionally substituted with one or two R groups. In some embodiments, T is a bivalent $C_{1-2}$ alkylene chain substituted with one or two R groups. In some embodiments, T is an unsubstituted bivalent $C_{1-2}$ alkylene chain. In some embodiments, T is a bivalent $C_1$ alkylene chain optionally substituted with one or two R groups. In some embodiments, T is a bivalent $C_2$ alkylene chain optionally substituted with one or two R groups. In some embodiments, T is optionally substituted with two R groups, wherein the two R groups are optionally taken together with their intervening atom(s) form a 3-8 membered saturated monocyclic ring having 0-2 heteroatoms independently selected from nitrogen, oxygen, or sulfur. In some embodiments, T is optionally substituted with two R groups, wherein the two R groups are taken together with their intervening atoms form a 3 membered saturated monocyclic ring having 0-2 heteroatoms independently selected from nitrogen, oxygen, or sulfur. In some embodiments, T is optionally substituted with two R groups, wherein the two R groups are taken together with their intervening atoms to form a 4-membered saturated monocyclic ring having 0-2 heteroatoms independently selected from nitrogen, oxygen, or sulfur. In certain embodiments, T is optionally substituted with two R groups, wherein the two R groups are taken together to form a cyclopropyl ring. In certain embodiments, T is optionally substituted with two R groups, wherein the two R groups are taken together to form a cyclobutyl ring.

In certain embodiments, T is —$CH_2$—, —$CD_2$-, or —$CH_2CH_2$—. In certain embodiments, T is —$CH_2$—. In certain embodiments, T is —$CD_2$-. In certain embodiments, T is —$CH_2CH_2$—. In certain embodiments, T is —$CH_2(CH_3)CH_2$—.

As defined generally above, each of $R^2$ and $R^{2'}$ is independently hydrogen, deuterium, halogen, or optionally substituted $C_{1-6}$ aliphatic. In some embodiments, $R^2$ is hydrogen. In some embodiments, $R^{2'}$ is hydrogen. In some embodiments, $R^2$ and $R^{2'}$ are both hydrogen. In some embodiments, $R^2$ is deuterium. In some embodiments, $R^{2'}$ is deuterium. In some embodiments, $R^2$ is fluorine. In some embodiments, $R^{2'}$ is fluorine. In some embodiments, $R^2$ is optionally substituted $C_{1-6}$ aliphatic. In some embodiments, $R^{2'}$ is optionally substituted $C_{1-6}$ aliphatic. In some embodiments, $R^2$ is optionally substituted $C_{1-6}$ aliphatic and $R^{2'}$ is hydrogen. In some embodiments, $R^2$ is hydrogen and $R^{2'}$ is optionally substituted $C_{1-6}$ aliphatic. In certain embodiments, at least one of $R^2$ or $R^{2'}$ is deuterium. In certain embodiments, at least one of $R^2$ or $R^{2'}$ is fluorine.

In certain embodiments, Ring B is phenyl substituted with 1-5 $R^3$ groups. In certain embodiments, Ring B is unsubstituted phenyl.

In certain embodiments, Ring B is naphthyl substituted with 1-5 $R^3$ groups. In certain embodiments, Ring B is unsubstituted naphthyl.

In some embodiments, Ring B is a 5-6 membered monocyclic heteroaryl ring having 1-4 heteroatoms independently selected from nitrogen, oxygen, or sulfur optionally substituted with 1-5 $R^3$ groups. In some embodiments, Ring B is a 5 membered monocyclic heteroaryl ring having 1-3 heteroatoms independently selected from nitrogen, oxygen, or sulfur optionally substituted with 1-2 $R^3$ groups. In wrier embodiments, Ring B is a 6 membered monocyclic heteroaryl ring having 1-2 heteroatoms independently selected from nitrogen, oxygen, or sulfur optionally substituted with 1-2 $R^3$ groups.

In certain embodiments, Ring B is an 8-10 membered bicyclic ring having 0-4 heteroatoms independently selected from nitrogen, oxygen, or sulfur, and optionally substituted with 1-5 $R^3$ groups. In some embodiments, Ring B is an 8 membered bicyclic ring having 1-3 heteroatoms independently selected from nitrogen, oxygen, or sulfur, and optionally substituted with 1-3 $R^3$ groups. In some embodiments, Ring B is a 9 membered bicyclic ring having 1-3 heteroatoms independently selected from nitrogen, oxygen, or sulfur, and optionally substituted with 1-3 $R^3$ groups. In some embodiments, Ring B is a 10 membered bicyclic ring having 1-3 heteroatoms independently selected from nitrogen, oxygen, or sulfur, and optionally substituted with 1-3 $R^3$ groups.

Exemplary Ring B heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one, wherein each ring is optionally substituted with 1-2 $R^3$ groups.

In certain embodiments, Ring B is selected from the group consisting of thienyl, pyrimidinyl, naphthyl, quinolyl, chromanyl, or 1,2,3,4-tetrahydronaphthyl, wherein each ring is optionally substituted with 1-2 $R^3$ groups.

In certain embodiments, Ring B is:

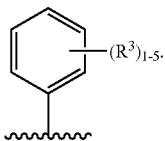

In certain embodiments, Ring B is:

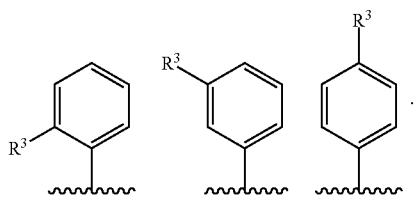

In certain embodiments, Ring B is:

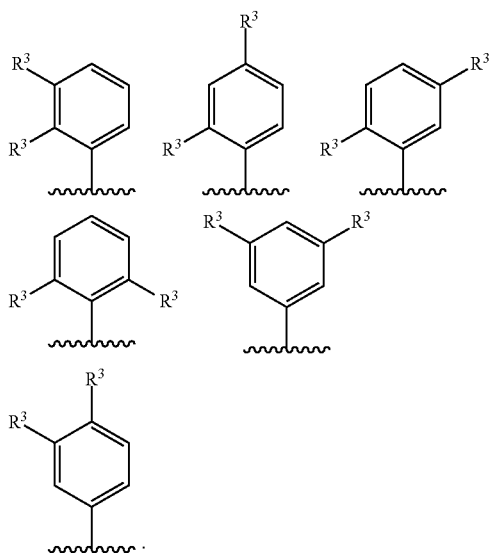

In certain embodiments, Ring B is:

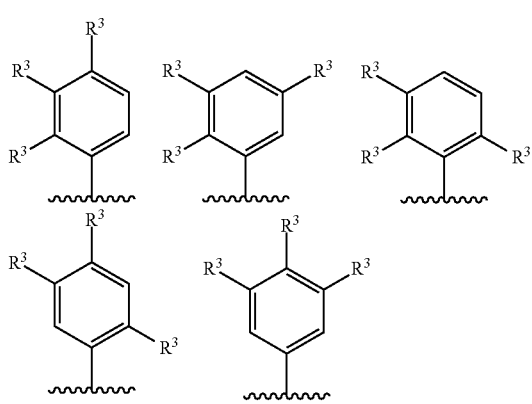

In certain embodiments, Ring B is:

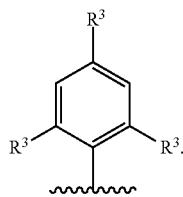

In certain embodiments, Ring B is:

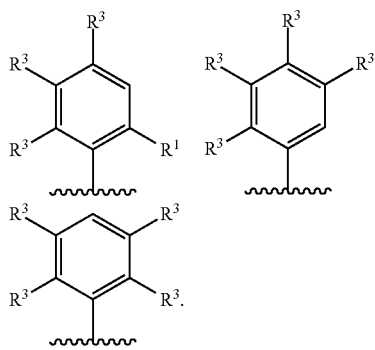

In certain embodiments, Ring B is:

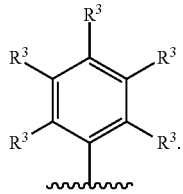

In certain embodiments, Ring B is:

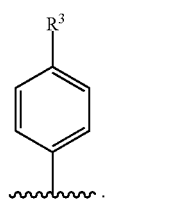

As defined above, each $R^3$ is independently selected from —R, halogen, —OR, —CN, —NO$_2$, —SR, —S(O)R, —SO$_2$R, —SO$_2$N(R)$_2$, —C(O)R, —CO$_2$R, —OC(O)R, —C(O)N(R)$_2$, —OC(O)N(R)$_2$, —NRC(O)R, —NRC(O)N (R)$_2$, —NRSO$_2$R, —N(R)$_2$, —C(R)$_3$, —Si(CH$_3$)$_3$, or an optionally substituted group selected from phenyl, a 5-6 membered monocyclic heteroaryl ring having 1-4 heteroatoms independently selected from nitrogen, oxygen, or sulfur, or an 8-10 membered bicyclic ring having 0-4 heteroatoms independently selected from nitrogen, oxygen, or sulfur. In some embodiments, $R^3$ is independently R, halogen, —OR, —CN, or —N(R)$_2$. In some embodiments, each $R^3$ is independently R, halogen, —OR, or —CN. In some embodiments, each $R^3$ is independently selected from hydrogen, deuterium, methyl, ethyl, propyl, butyl, pentyl, hexyl, —CF$_3$, —CF$_2$H, —CFH$_2$, —CF$_2$CF$_3$, —CFHCF$_3$, —CH$_2$CF$_3$, —CF₂CF₂H, —CF₂CFH₂, —CF₂CH₃, —CFHCF₂H, —CFHCFH₂; or —CFHCH₃. In some embodiments, R³ is selected from the group consisting of —CF₃, —CF₂H, —CFH₂, —CF₂CF₃, —CFHCF₃, —CH₂CF₃, —CF₂CF₂H, —CFCFH₂, —CF₂CH₃, —CFHCF₂H, —CFHCFH₂, and —CFHCH₃.

In some embodiments, each R³ is independently —OR, wherein R is independently selected from hydrogen, methyl, ethyl, propyl, —CF₃, —CF₂H, —CFH₂, —CF₂CF₃, —CFHCF₃, —CH₂CF₃, —CF₂CF₂H, —CF₂CFH₂, —CF₂CH₃, —CFHCF₂H, —CFHCFH₂, or —CFHCH₃. In some embodiments, at least one R³ is —OR, wherein R is independently selected from hydrogen, methyl, ethyl, propyl, —CF₃, —CF₂H, and —CF₂CF₃.

In certain embodiments, R³ is substituted phenyl. In certain embodiments, R³ is unsubstituted phenyl.

In certain embodiments, R³ is substituted naphthyl. In certain embodiments, R³ is unsubstituted naphthyl.

In some embodiments, R³ is an optionally substituted 5-6 membered monocyclic heteroaryl ring having 1-4 heteroatoms independently selected from nitrogen, oxygen, or sulfur. In some embodiments, R³ is an optionally substituted 5 membered monocyclic heteroaryl ring having 1-3 heteroatoms independently selected from nitrogen, oxygen, or sulfur. In other embodiments, R³ is an optionally substituted 6 membered monocyclic heteroaryl ring having 1-2 nitrogens independently selected from nitrogen, oxygen, or sulfur.

In certain embodiments, R³ is an optionally substituted 8-10 membered bicyclic ring having 0-4 heteroatoms independently selected from nitrogen, oxygen, or sulfur. In some embodiments, R³ is an optionally substituted 8 membered bicyclic ring having 1-3 heteroatoms independently selected from nitrogen, oxygen, or sulfur. In some embodiments, R³ is an optionally substituted 9 membered bicyclic ring having 1-3 heteroatoms independently selected from nitrogen, oxygen, or sulfur. In some embodiments, R³ is an optionally substituted 10 membered bicyclic ring having 1-3 heteroatoms independently selected from nitrogen, oxygen, or sulfur. In some embodiments, R³ is an optionally substituted 8-10 membered bicyclic ring comprised of 0-2 aromatic rings.

Exemplary optionally substituted R³ heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, or chromanyl.

In some embodiments, each R³ is independently —N(R)₂, wherein each R is independently methyl or ethyl. In some embodiments, two R on the same nitrogen are taken together to form a 5-6 membered saturated or partially saturated, or aromatic ring having 1-3 heteroatoms independently selected from nitrogen, oxygen, and sulfur. In some embodiments, two R on the same nitrogen are taken together to form a 5 membered saturated, partially saturated, or aromatic ring having 1-3 heteroatoms independently selected from nitrogen, oxygen, and sulfur. In some embodiments, two R on the same nitrogen are taken together to form a 6 membered saturated, partially saturated, or aromatic ring having 1-3 heteroatoms independently selected from nitrogen, oxygen, and sulfur.

In some embodiments, each R³ is independently —SR, —S(O)R, or —SO₂R wherein R is hydrogen, methyl, ethyl, or propyl.

In some embodiments, each R³ is independently —C(O)R or —CO₂R, wherein R is hydrogen, methyl, ethyl, propyl, or trifluoromethyl.

In some embodiments, each R³ is —C(O)N(R)₂, —NRC(O)R, —NRC(O)N(R)₂, or —NRSO₂R, wherein R is hydrogen, methyl, ethyl, or propyl. In certain embodiments, R¹ is —NHSO₂R. In certain embodiments, R³ is —CN.

In certain embodiments, R³ is fluorine.

In certain embodiment, at least one R³ is selected from the group consisting of hydrogen, methyl, ethyl, propyl, or butyl.

In some embodiments, the present invention provides a compound of formula I-a:

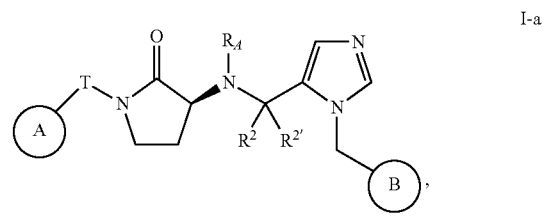

or a pharmaceutically acceptable salt thereof, wherein each of Ring A, Ring B, R², R²', R_A and T are as defined and described herein.

In some embodiments, the present invention provides a compound of formula I-b:

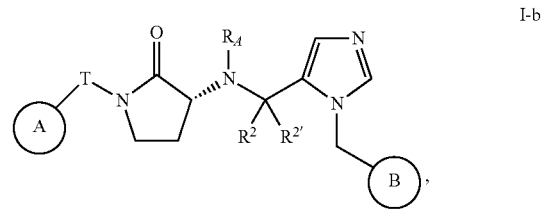

or a pharmaceutically acceptable salt thereof, wherein each of Ring A, Ring B, R², R²', R_A, and T are as defined and described herein.

In certain embodiments, a provided compound is of formula I-a1:

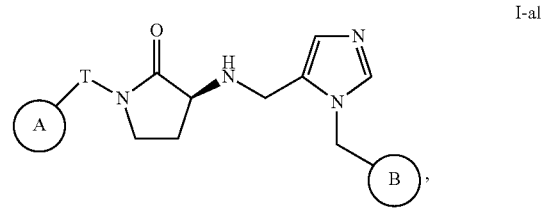

or a pharmaceutically acceptable salt thereof, wherein each of Ring A, Ring B, R², R²', and T are as defined and described herein.

In certain embodiments, a provided compound is of formula I-b1:

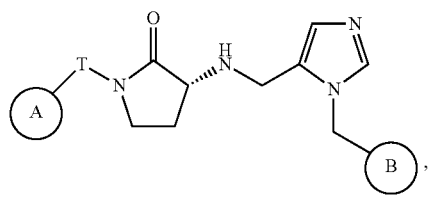

I-b1 or a pharmaceutically acceptable salt thereof, wherein each of Ring A, Ring B, $R^2$, $R^{2'}$, and T are as defined and described herein.

In certain embodiments, a provided compound is of formula I-a2 or I-b2:

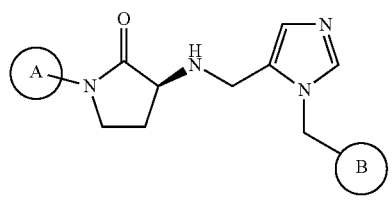

I-a2

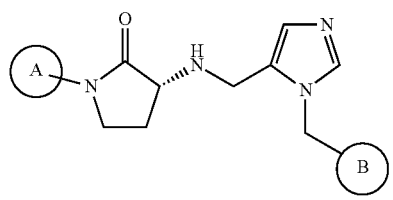

I-b2 or a pharmaceutically acceptable salt thereof, wherein each of Ring A and Ring B are as defined and described herein.

In certain embodiments, a provided compound is of formula I-a3 or I-b3:

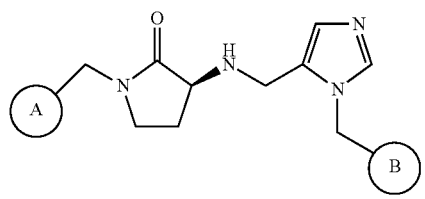

I-a3

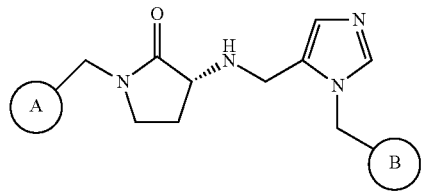

I-b3 or a pharmaceutically acceptable salt thereof, wherein each of Ring A and Ring B are as defined and described herein.

In certain embodiments, a provided compound is of formula I-a4 or I-b4:

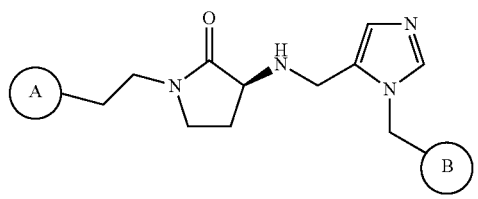

I-a4

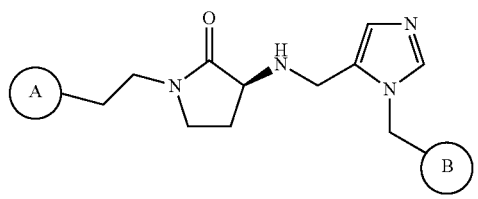

I-b4 or a pharmaceutically acceptable salt thereof, wherein each of Ring A and Ring B are as defined and described herein.

In certain embodiments, a provided compound is of any one of formulae:

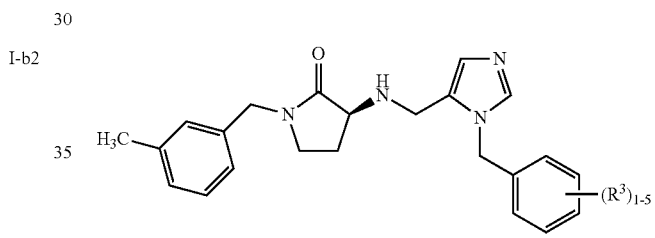

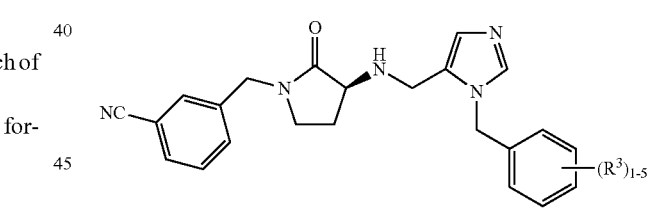

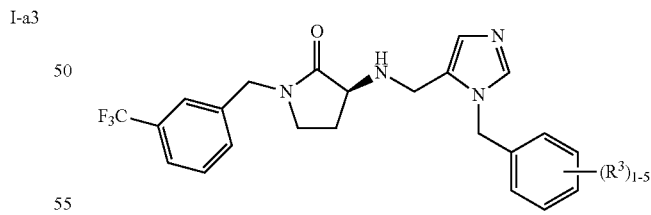

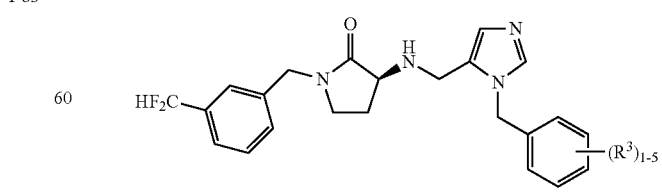

or a pharmaceutically acceptable salt thereof, wherein $R^3$ is as defined and described herein.

In certain embodiments, a provided compound is of any one of formulae:

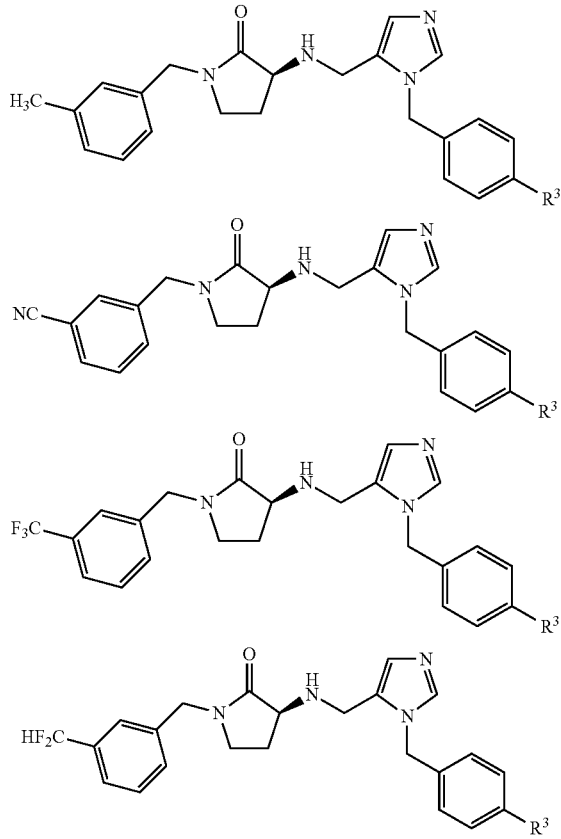

or a pharmaceutically acceptable salt thereof, wherein $R^3$ is as defined and described herein.

In certain embodiments, a provided compound is of any one of formulae:

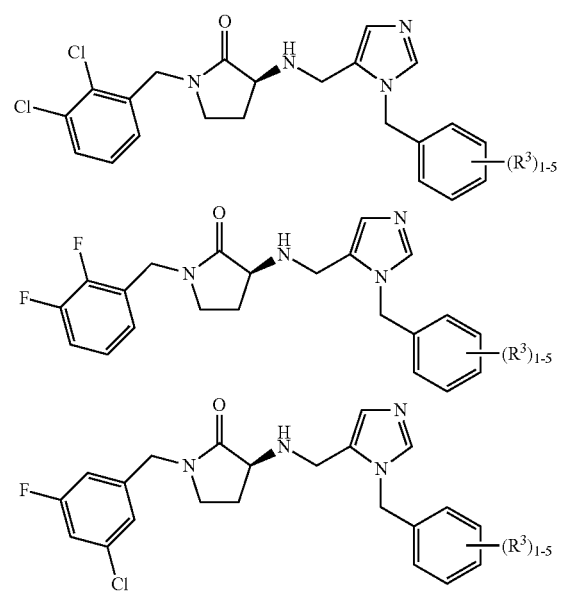

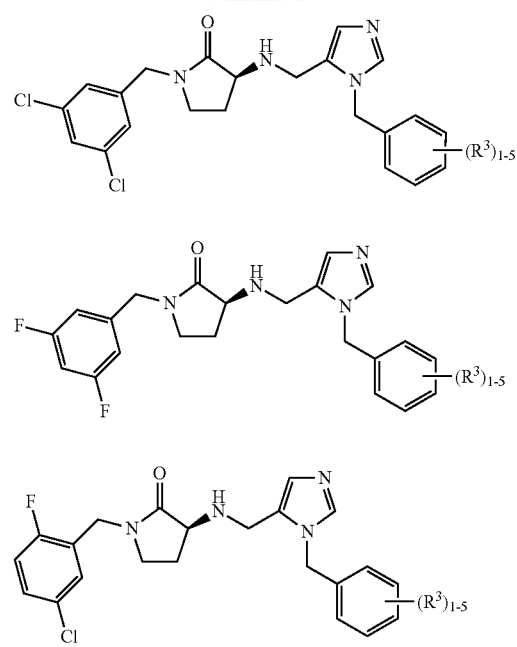

or a pharmaceutically acceptable salt thereof, wherein $R^3$ is as defined and described herein.

In certain embodiments, a provided compound is of any one of formulae:

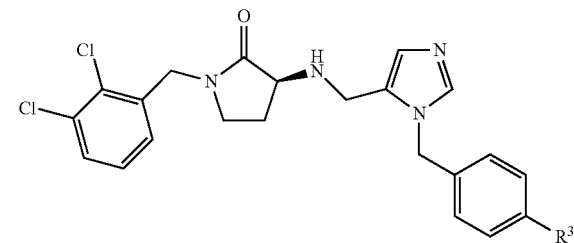

-continued

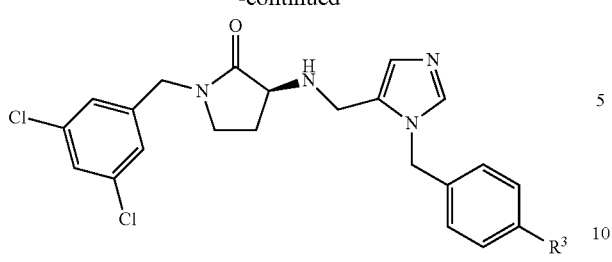

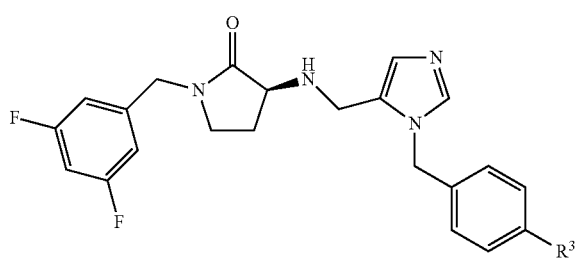

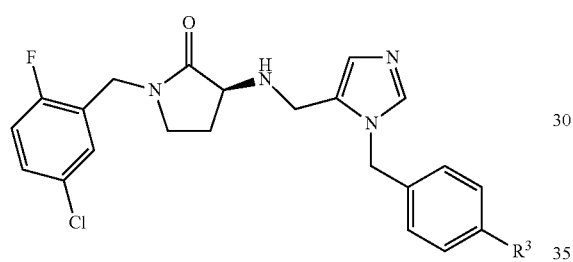

or a pharmaceutically acceptable salt thereof, wherein R³ is as defined and described herein.

In certain embodiments, a provided compound is of any of formulae:

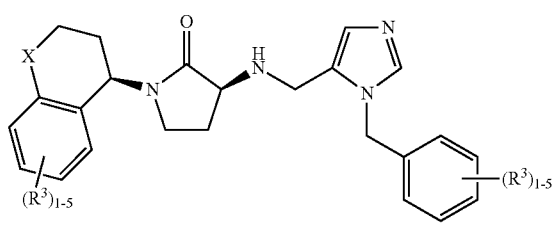

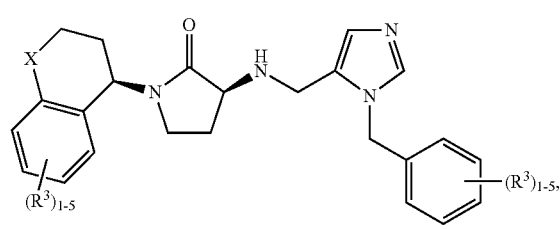

wherein R³ is as described herein and X is selected from CH₂ or O.

In certain embodiments, a provided compound is of any of formulae:

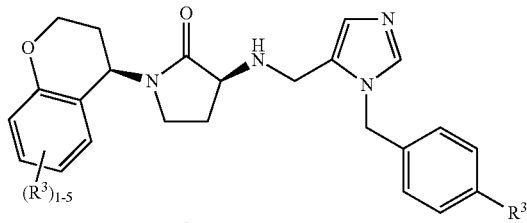

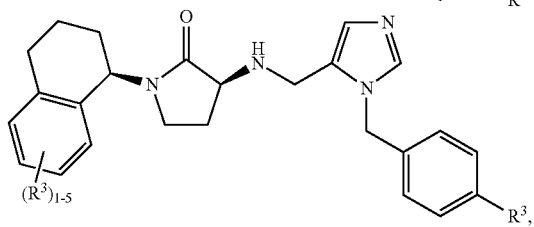

wherein R³ is as described herein.

In certain embodiments, a provided compound is of any of formulae:

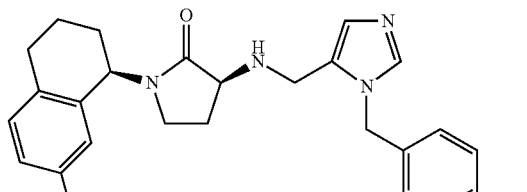

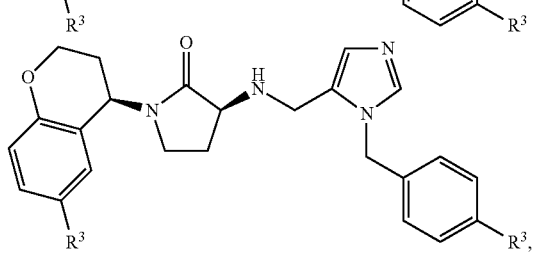

wherein R³ is as described herein.

In certain embodiments, a provided compound is of any of formulae:

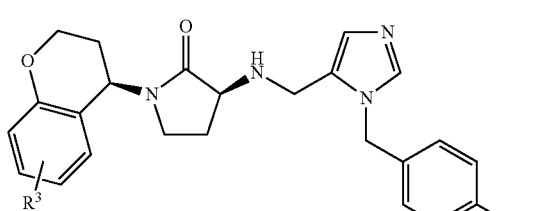

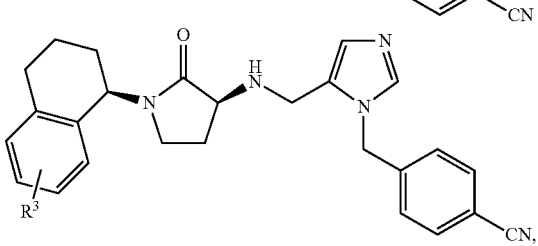

wherein R³ is as described herein.

In certain embodiments, a provided compound is of any of formulae:

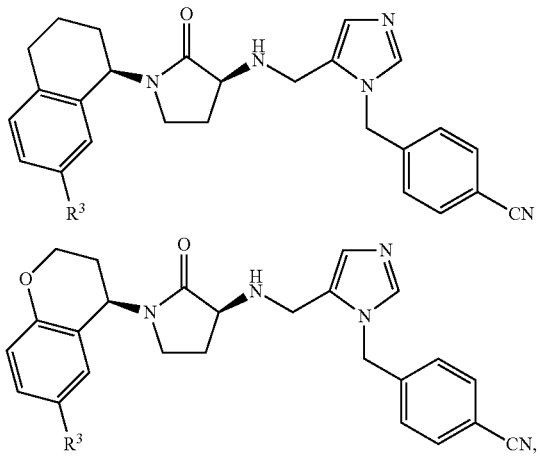

wherein R³ is as described herein.

In certain embodiments, a provided ompound is of any of formulae:

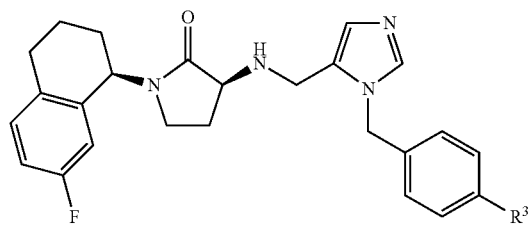

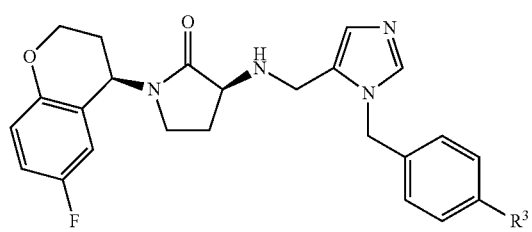

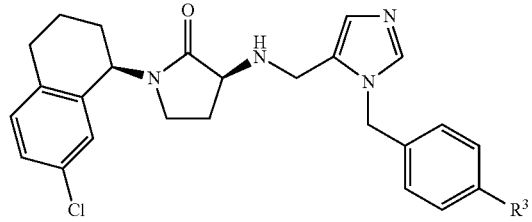

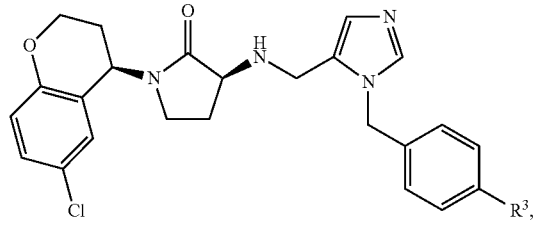

wherein R³ is as described herein.

In certain embodiments, a provided compound is of formula III:

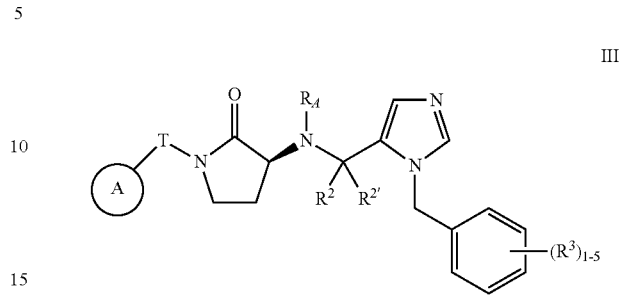

or a pharmaceutically acceptable salt thereof, wherein A, T, $R^2$, $R^{2'}$, $R_A$, and $R^3$ are as described herein.

In certain embodiments, a provided compound is of formula III-a:

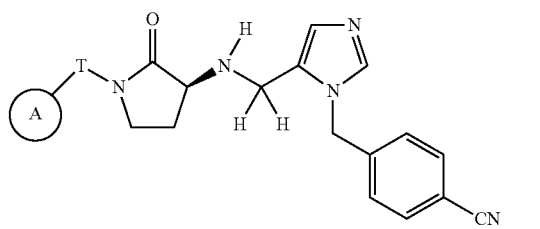

or a pharmaceutically acceptable salt thereof, wherein A and T are as described herein.

Exemplary compounds of the present invention are set forth below:

(31)

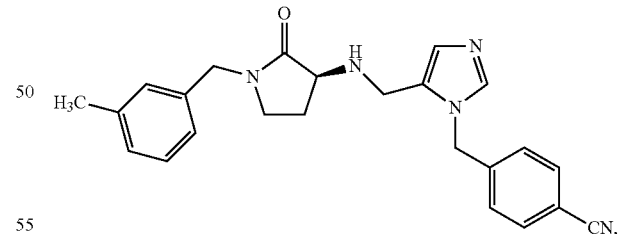

(32)

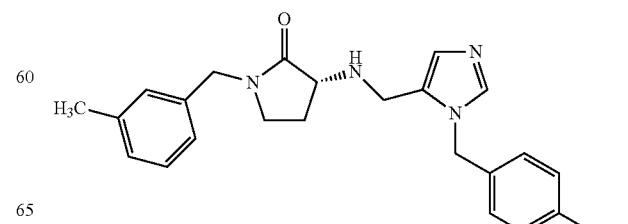

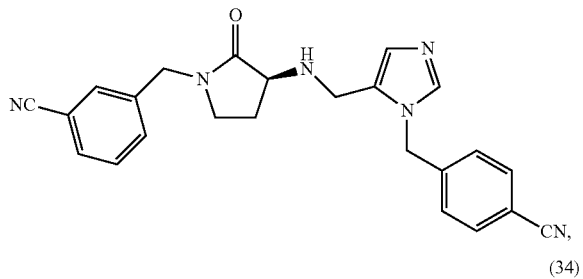
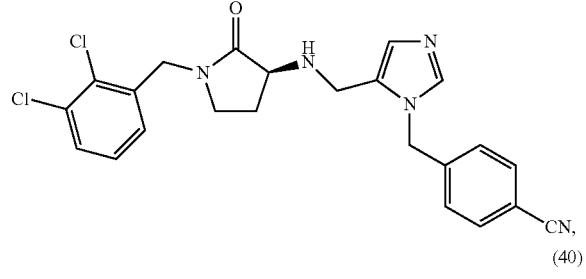
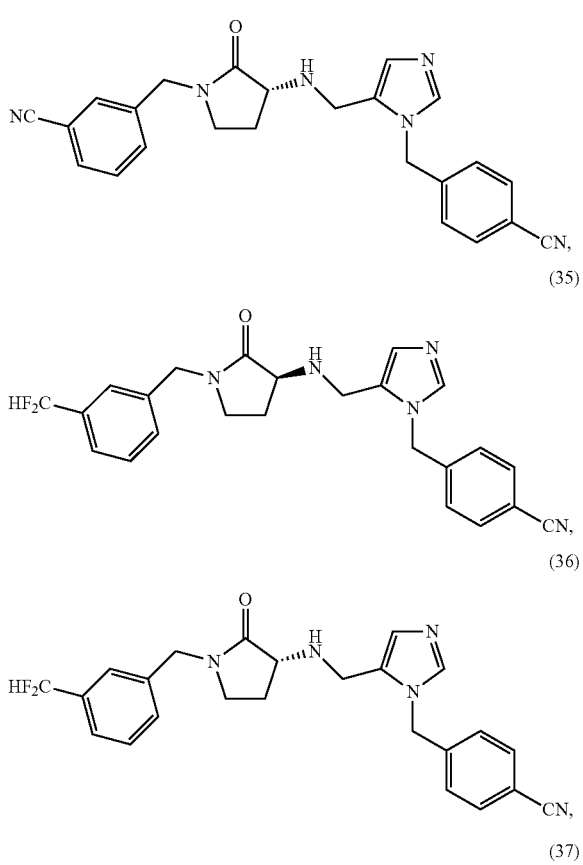
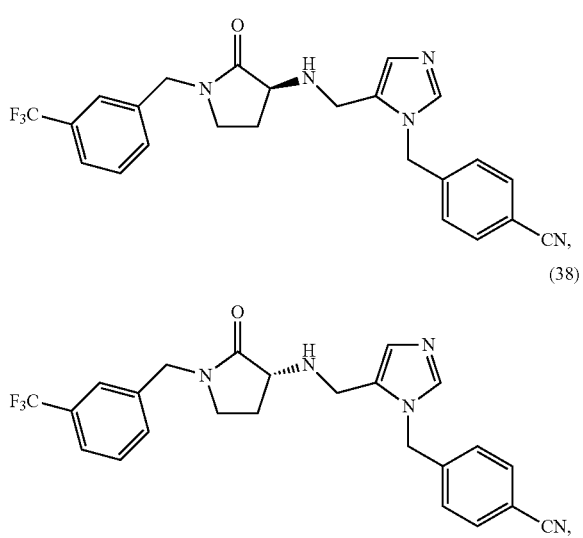

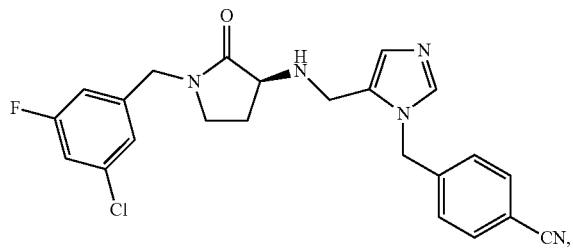
(46)
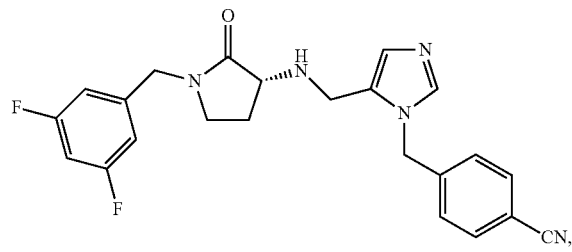
(51)
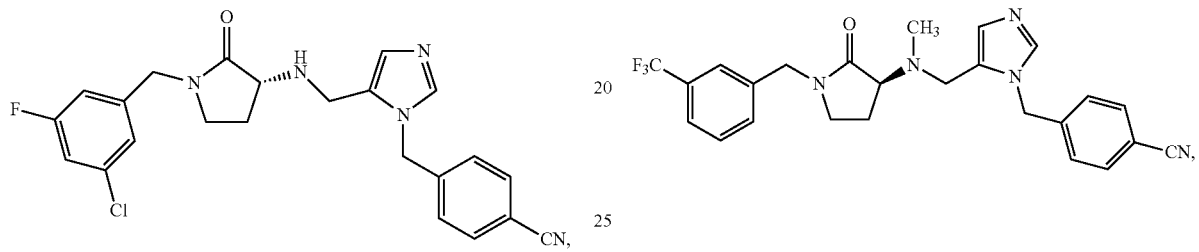
(47)
(52)
(53)
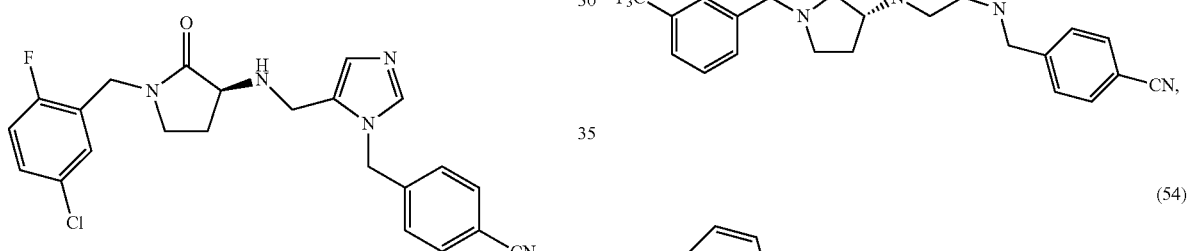
(48)
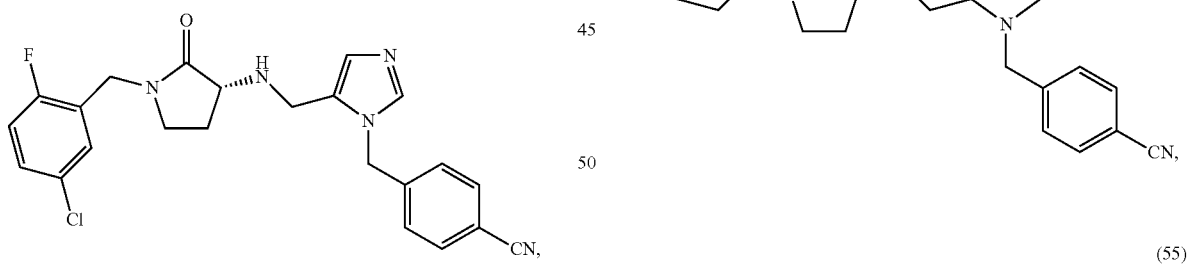
(49)
(54)
(50)
(55)
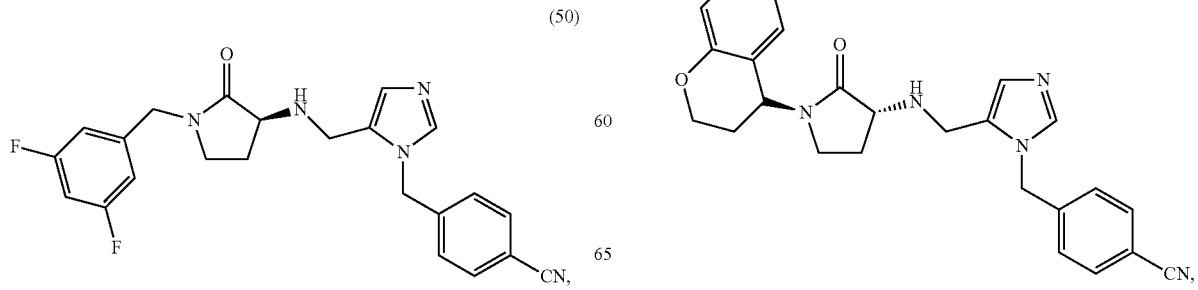

(56)
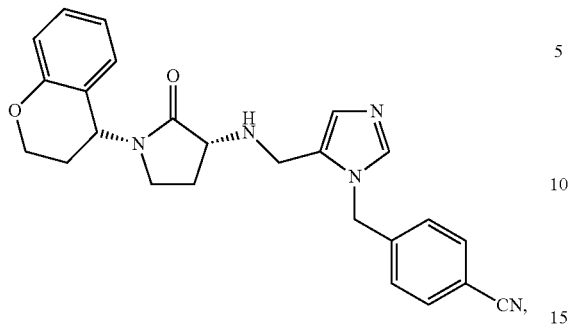
(57)
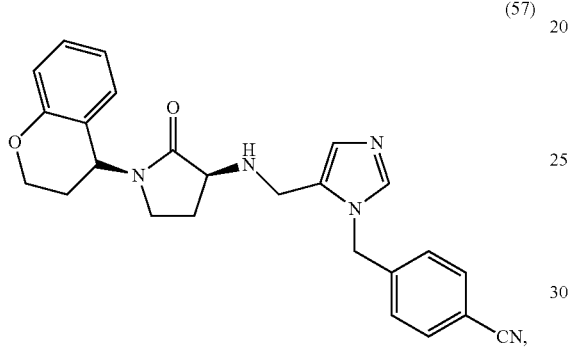
(58)
(59)
(60)
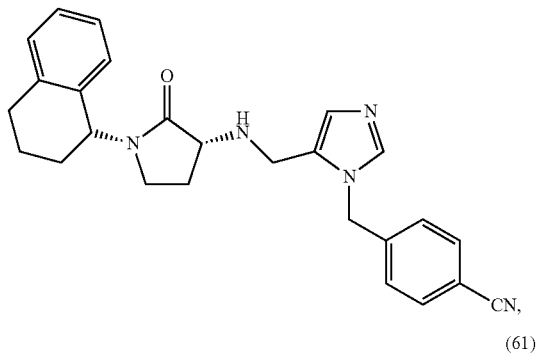
(61)
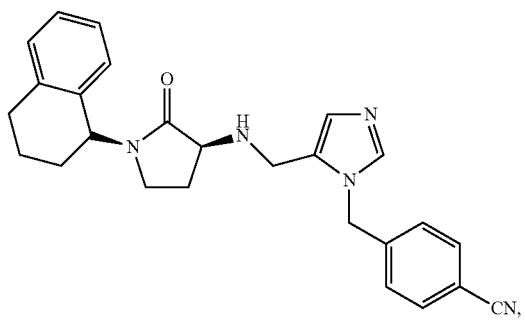
(62)
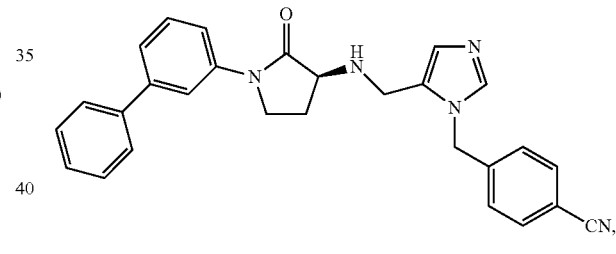
(63)
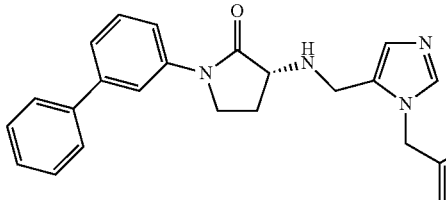
(64)
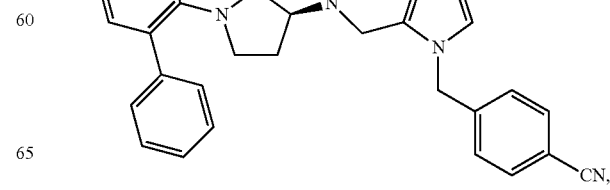

(65)
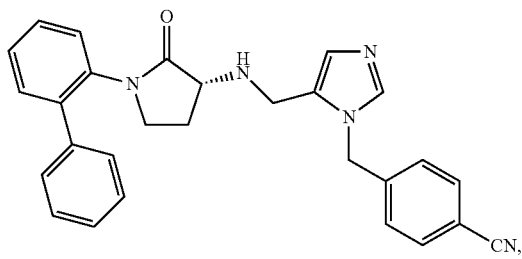

(28)
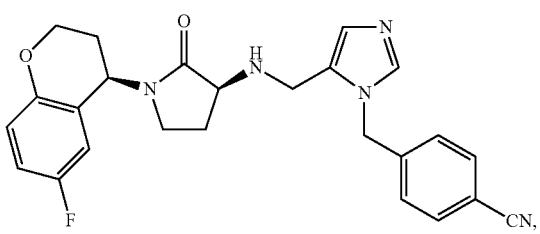

(29)
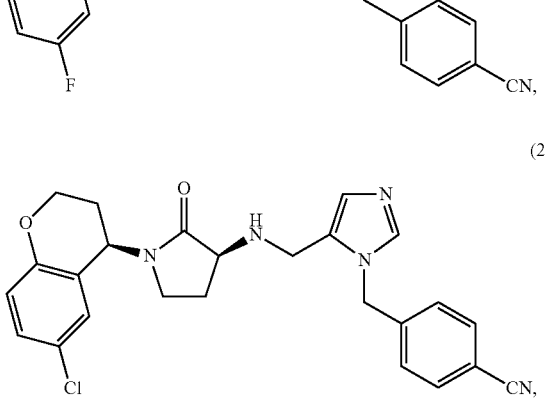

(30)
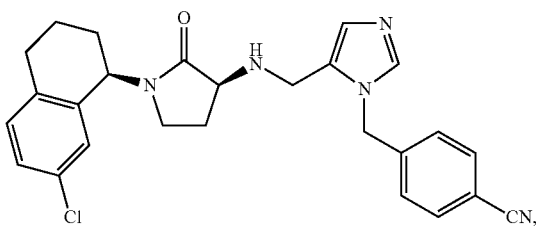

(66)
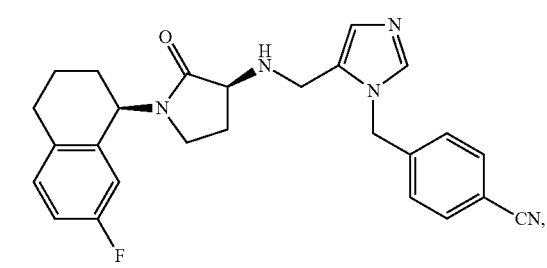

(68)
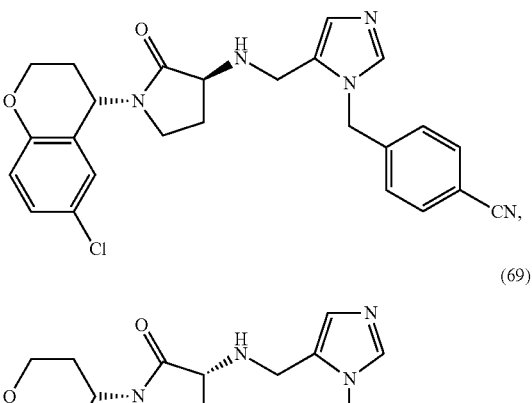

(69)
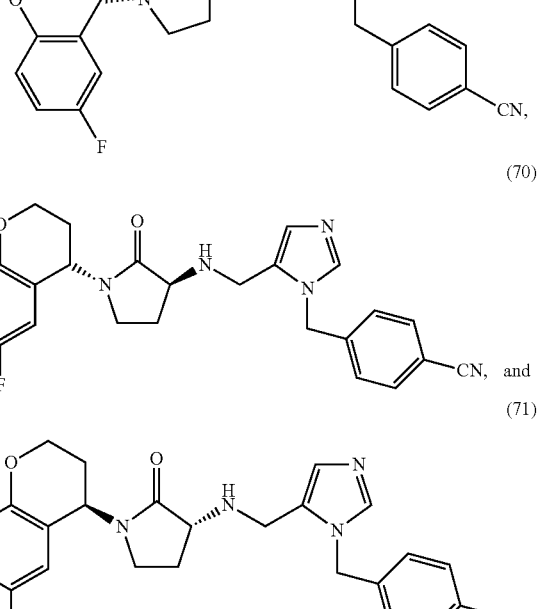

(70)
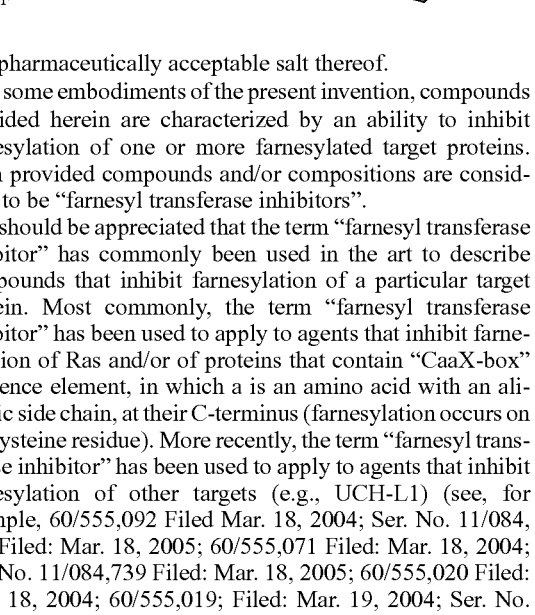

and (71)

or a pharmaceutically acceptable salt thereof.

In some embodiments of the present invention, compounds provided herein are characterized by an ability to inhibit farnesylation of one or more farnesylated target proteins. Such provided compounds and/or compositions are considered to be "farnesyl transferase inhibitors".

It should be appreciated that the term "farnesyl transferase inhibitor" has commonly been used in the art to describe compounds that inhibit farnesylation of a particular target protein. Most commonly, the term "farnesyl transferase inhibitor" has been used to apply to agents that inhibit farnesylation of Ras and/or of proteins that contain "CaaX-box" sequence element, in which a is an amino acid with an aliphatic side chain, at their C-terminus (farnesylation occurs on the cysteine residue). More recently, the term "farnesyl transferase inhibitor" has been used to apply to agents that inhibit farnesylation of other targets (e.g., UCH-L1) (see, for example, 60/555,092 Filed Mar. 18, 2004; Ser. No. 11/084,715 Filed: Mar. 18, 2005; 60/555,071 Filed: Mar. 18, 2004; Ser. No. 11/084,739 Filed: Mar. 18, 2005; 60/555,020 Filed: Mar. 18, 2004; 60/555,019; Filed: Mar. 19, 2004; Ser. No. 11/084,740; Filed: Mar. 18, 2005; 60/555,070; Filed: Mar. 18, 2004; Ser. No. 11/084,695; Filed: Mar. 18, 2005 60/753,809; Filed: Dec. 23, 2005; Ser. No. 11/615,088; Filed: Dec. 22, 2006; 60/764,678; Filed: Feb. 2, 2006; U.S. Ser. No. 12/161, 650; Filed: Feb. 2, 2007; 60/813,181; Filed: Jun. 13, 2006; 60/554,634; Filed: Mar. 18, 2004; Ser. No. 11/084,716; Filed: Mar. 18, 2005; 60/653,983; Filed: Feb. 18, 2005; Ser. No. 11/354,896; Filed: Feb. 16, 2006; 60/894,086 Filed: Mar. 9, 2007; PCT/US08/56162; Filed: Mar. 7, 2008; 60/915,828; Filed: May 3, 2007; PCT/US08/62437 Filed: May 2, 2008; 61/121,373; Filed: Dec. 10, 2008). Typically, a compound is considered to be a "farnesyl transferase inhibitor" whether it directly targets (e.g., binds to) the farnesyl transferase enzyme, or whether it otherwise achieves a reduction in farnesylation of one or more targets of interest.

The modification of a protein by a farnesyl group can have an important effect on function for a number of proteins. Farnesylated proteins typically undergo further C-terminal modification events that include a proteolytic removal of three C-terminal amino acids and carboxymethylation of C-terminal cystines. These C-terminal modifications facilitate protein-membrane association as well as protein-protein interactions. Farnesylation is catalyzed by a protein farnesyltransferase (FTase), a heterodimeric enzyme that recognizes the a cysteine-containing motif present at the C-terminus of the substrate protein. FTase transfers a farnesyl group from farnesyl pyrophosphate and forms a thioether linkage between the farnesyl and the relevant cystine residue.

In certain embodiments, inhibitory activity of a provided compound with respect to farnesylation of a particular target may be assayed by in vivo and/or in vitro assays. In certain embodiments, the $IC_{50}$ as measured in an in vitro assay using recombinant farnesyl transferase is less than about 100 nM. In certain embodiments, the $IC_{50}$ is less than about 50 nM. In certain embodiments, the $IC_{50}$ is less than about 10 nM. In certain embodiments, the $IC_{50}$ is less than about 5 nM. In certain embodiments, the $IC_{50}$ is less than about 1 nM.

In some embodiments of the present invention, provided compounds that act as farnesyl transferase inhibitors characterized by and/or are administered under conditions and/or according to a regimen that achieves differential effects on farnesylation of different target proteins (i.e., at least one favored target and at least one disfavored target). In many embodiments, the disfavored target is Ras. In some embodiments, the disfavored target contains a CaaX sequence element; in some such embodiments, X is any amino acid; in some such embodiments, X is serine, methionine, gutamine, alanin, or threonine. In some embodiments, the favored target is a non-Ras target. In some embodiments, the favored target does not contain a CaaX-COOH sequence element (as described herein). In some embodiments, the favored target contains a CKaa-COOH sequence element (where K is lysine). In some embodiments, the favored target contains a CKAA-COOH sequence element (where A is alanine). In some embodiments, the favored target is UCH-L1. It has recently been discovered that UCH-L1 is farnesylated in vivo. UCH-L1 is associated with the membrane and this membrane association is mediated by farnesylation. Farnesylated UCH-L1 also stabilizes the accumulation of α-synuclein. The invention relates to the prevention or inhibition of UCH-L1 farnesylation which would result in UCH-L1 membrane disassociation and acceleration of the degradation of α-synuclein. Since α-synuclein accumulation is pathogenic in PD, DLBD, and MSA, an increased degradation of α-synuclein and/or inhibition of α-synuclein accumulation ameliorates the toxicity associated with a pathogenic accumulation of α-synuclein.

In some embodiments, where compounds provided herein are characterized by and/or are administered under conditions and/or according to a regimen that achieves differential effects on farnesylation of different target proteins (i.e., at least one favored target and at least one disfavored target), the effect on the favored target is at least 2, 3, 4, 5, 6, 7, 8, 9, 10, 15, 20, 25, 30, 35, 40, 45, 50, 100, 500, or 1000 times, or more greater than the effect on the disfavored target.

In some embodiments, farnesyl transferase inhibitors utilized in accordance with the present invention are characterized by and/or are administered under conditions and/or according to a regimen that achieves a less than 50% reduction in Ras farnesylation. In some embodiments, Ras farnesylation is reduced less than 45%, 40%, 35%, 30%, 25%, 20%, 15%, 10%, 5% or less. It will be appreciated by those of ordinary skill in the art that studies have illustrated that Ras farnesylation must be reduced by more than 50%, and often much more than 50%, in order to achieve beneficial effects in the treatment of cancer. In some embodiments of the present invention, farnesyl transferase inhibitors are utilized at doses that are at least 2, 3, 4, 5, 6, 7, 8, 9, 10, 15, 20, 25, 30, 35, 40, 45, 50, 100, 500, 1000 fold or more lower than doses required for effects in the treatment of cancer.

In some embodiments, compounds utilized in accordance with the present invention are characterized by and/or are administered under conditions and/or according to a regimen that achieves a reduction in levels of aggregates of one or more proteins of interest. In some embodiments, rates of aggregation and/or of disaggregation and/or protein destruction are altered. In some such embodiments, administration of a compound provided herein to an organism reduces levels of aggregates in one or more particular tissues of interest. In some embodiments, the aggregates are aggregates of a protein selected from the group consisting of α-synuclein (synucleinopathies), tau (tauopathies), amyloid (amyloidopathies), SOD1 (SOD1 proteinopathies), TDP-43 (TDP-43 proteinopathies), huntingtin, and combinations thereof. In some embodiments, the target tissues are or include brain. In some embodiments, aggregate levels are reduced at least 90%, 85%, 80%, 75%, 70%, 65%, 60%, 55%, 50%, 45%, 40%, 35%, 30%, 25%, 20%, 15%, 10%, 5% or more.

In some embodiments of the present invention, compounds provided herein are characterized by and/or are administered under conditions and/or according to a regimen that achieves no significant inhibition of cell cycle progression. For example, in some embodiments, compounds provided herein are characterized by and/or are administered under conditions and/or according to a regimen that achieves less than 100%, 95%, 90%, 85%, 80%, 75%, 70%, 65%, 60%, 55%, 50%, 45%, 40%, 35%, 30%, 25%, 20%, 15%, 10% inhibition of cell cycle progression. In some embodiments, compounds provided herein show a Ki within the range of 0.001-, 0.010 nM, 0.01-0.10 nM, 0.10-1 nM, or 1-10 nM, when tested for effects on proliferation of cancer cells in vitro.

In some embodiments, compounds provided herein are characterized by and/or are administered under conditions and/or according to a regimen that achieves stimulation of a protein clearance pathway (e.g., through inhibition of farnesylation). In some embodiments, compounds provided herein are characterized by and/or are administered under conditions and/or according to a regimen that achieves stimulation of autophagy. In some embodiments, compounds provided herein are characterized by and/or are administered under conditions and/or according to a regimen that achieves stimulation of neural autophagy, macroautophagy, and/or microautophagy.

In some embodiments, compounds provided herein are characterized by and/or are administered under conditions and/or according to a regimen that achieves one or more of alteration of protein folding pathways, reduction of protein aggregation, alteration of protein degradation pathways, etc. In some embodiments, such alterations stimulate the relevant pathways. In some embodiments, such alterations inhibit the relevant pathways.

In some embodiments, compounds provided herein are characterized by and/or are administered under conditions and/or according to a regimen that achieves no significant inhibition of geranylgeranyltransferase "GGTase" activity. In some embodiments, GGTase activity is inhibited no more than 1%, 2%, 3%, 4%, 5%, 6%, 7%, 8%, 9%, 10%, 12%, 15%, 20%, 25%, 30%, 35%, 40%, 45%, 50%, 55%, 60%, 65%, 70%, or 75%.

In some embodiments, compounds provided herein are characterized by and/or are administered under conditions and/or according to a regimen that achieves differential inhibition of farnesyl transferase activity (with respect to a favored target) as compared with GGTase activity. In some embodiments, compounds provided herein are characterized by and/or are administered under conditions and/or according to a regimen that achieve a level of farnesyl transferase inhibition (with respect to a favored target) that is at least 2, 3, 4, 5, 6, 7, 8, 9, 10, 15, 20, 25, 30, 35, 40, 45, 50, 100, 500, or 1000 times greater, or more, than the achieved level of GGTase inhibition.

4. General Methods of Providing the Present Compounds:

Provided compounds are prepared by methods known to one of ordinary skill in the art and including methods illustrated in Schemes 1-4, below. Unless otherwise noted, all variables are as defined above and in classes and subclasses herein.

In the Schemes below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in *March's Advanced Organic Chemistry Reactions, Mechanisms, and Structure*, M. B. Smith and J. March, 5th Edition, John Wiley & Sons, 2001, *Comprehensive Organic Transformations*, R. C. Larock, 2nd Edition, John Wiley & Sons, 1999, and *Protecting Groups in Organic Synthesis*, T. W. Greene and P. G. M. Wuts, 3rd edition, John Wiley & Sons, 1999, the entirety of each of which is hereby incorporated herein by reference.

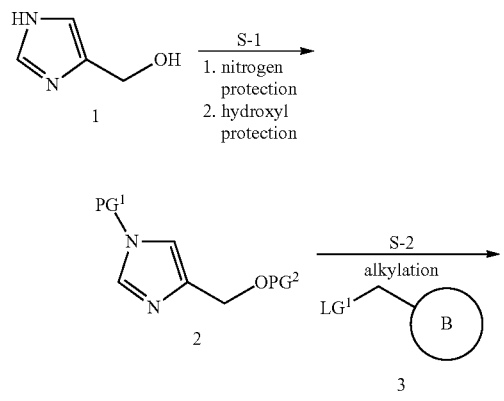

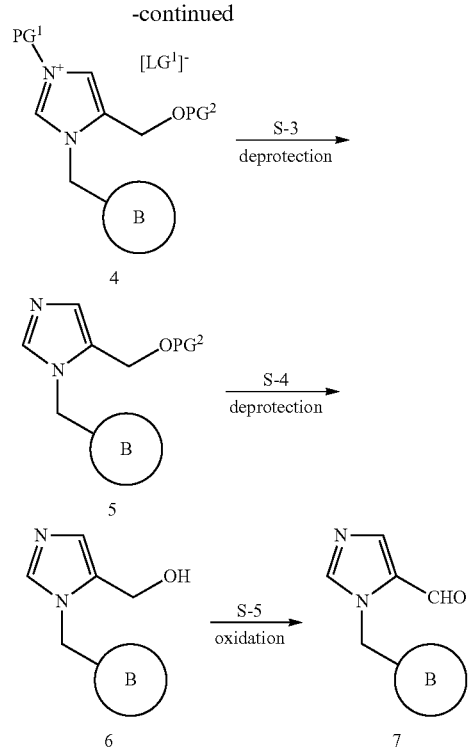

Coupling partner 7 for use in Scheme 3, below, is synthesized from (1H-imidazol-4-yl)methanol 1. In some embodiments, aldehyde 7 is prepared in a manner substantially similar to that described by Bell et al., *J. Med. Chem.* 2001, 44, 2933-2949; Williams et al., *J. Med. Chem.* 1999, 42, 3779.

As depicted in Scheme 1 above, S-1 illustrates the protection of (1H-imidazol-4-yl)methanol 1 to afford compound 2. In some embodiments, selective protection of the nitrogen moiety occurs with an appropriate protecting group (e.g., trityl chloride) under basic conditions (e.g., triethylamine) in a suitable solvent (e.g., dimethylformamide (DMF)). In some embodiments, subsequent protection of the hydroxyl moiety comprises acylation. In certain embodiments, the hydroxyl moiety is acylated under basic conditions (e.g., in the presence of pyridine) with a suitable acylating agent (e.g., acetic anhydride) to provide compound 2.

In step S-2 above, alkylation of the remaining nitrogen of the imidazole ring under standard conditions using alkylating agent 3 furnishes alkylated imidazolium 4. In some embodiments, alkylating agent 3 is prepared so as to contain a suitably reactive leaving group capable of being displaced upon exposure to compound 2 under suitable conditions. In certain embodiments, the suitably reactive leaving group is a halide (e.g., a bromide) and suitable conditions comprise a suitable solvent (e.g., acetonitrile), reaction time (e.g., 3 h), and reaction temperature (e.g., 80° C.) to facilitate conversion to alkylated imidazolium 4.

In step S-3 above, imidazolium 4 is selectively deprotected at nitrogen to afford compound 5. In some embodiments, deprotection occurs using a protic solvent at elevated temperatures. In certain embodiments, the protecting group is trityl and deprotection occurs using refluxing methanol.

As shown in step S-4 above, deprotection of compound 5 provides free alcohol 6. In some embodiments, deprotection of compound 5 occurs under basic conditions. In certain embodiments, the protecting group is an acyl group and deprotection occurs using an alkoxide salt in the corresponding alcoholic solvent (e.g., sodium methoxide in methanol).

As shown in step S-5 above, the free alcohol moiety is then oxidized using a suitable oxidant to furnish aldehyde 7. In some embodiments, oxidation occurs under basic conditions. In certain embodiments, the oxidant is a sulfur oxide-amine complex (e.g., $SO_3$-pyridine) in dimethylsulfoxide (DMSO) and oxidation occurs in the presence of an additional amine base (e.g., triethylamine).

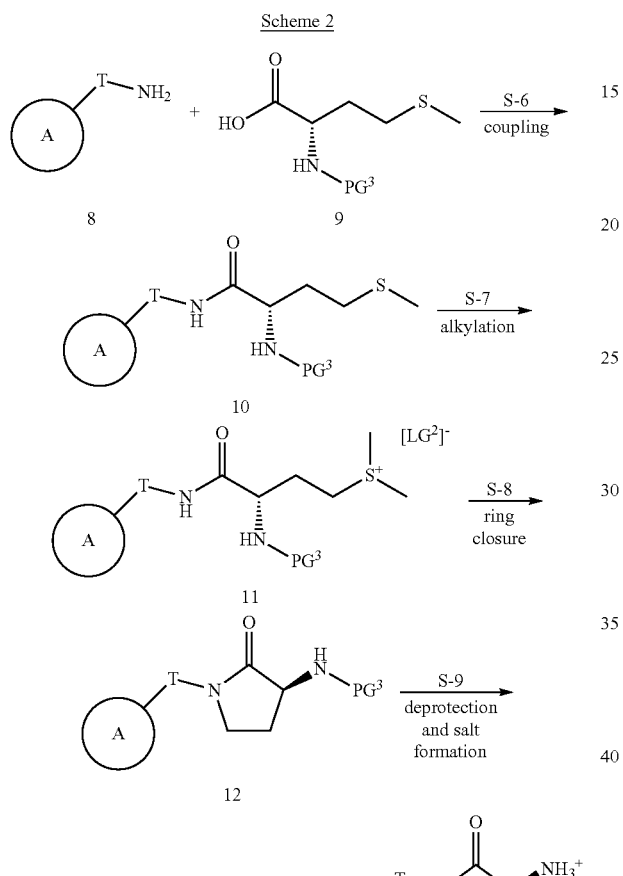

Coupling partner 13 for use in Scheme 3, below, is synthesized from primary amine 8.

In step S-6 shown above, amine 8 is coupled to N-protected (S)-2-amino-4-(methylthio)butanoic acid 9 using standard coupling reagents to form amide 10. In some embodiments, coupling of the amine to the carboxylic acid moiety of the amino acid occurs in the presence of one or more coupling reagents under basic conditions to provide the corresponding amide. In certain embodiments, the coupling reagent is a peptide coupling reagent (e.g., 2-(1H-7-azabenzotriazol-1-yl)-1,1,3,3-tetramethyl uronium hexafluorophosphate methanaminium (HATU)), the base is an amine base (e.g., diisopropylethylamine) and the reaction takes place in a chlorinated solvent (e.g., methylene chloride).

In step S-7 shown above, alkylation of the sulfide moiety of 10 furnishes sulfonium salt 11. In some embodiments, alkylation occurs using an alkylating agent containing a suitably reactive leaving group. In some embodiments, the alkylating agent is an alkyl halide. In certain embodiments, the alkylating agent is a methylating agent (e.g., methyl iodide).

As illustrated in step S-8, subsequent cyclization of sulfonium salt 11 provides substituted lactam 12. In some embodiments, cyclization occurs in an anhydrous solvent under basic conditions. In certain embodiments, the anhydrous solvent is an ethereal solvent (e.g., tetrahydrofuran (THF)) and the base is a lithium amide salt (e.g., lithium hexamethyldisilazide (LiHMDS)).

In step S-9 shown above, the protected amino moiety of lactam 12 is deprotected and the free amine is reacted with an appropriate acid to form the corresponding amine salt coupling partner 13. In some embodiments, the reagent used to deprotect the amine of compound 12 is also the same reagent used to form the corresponding amine salt 13. In certain embodiments, the protecting group is an acid labile protecting group (e.g., a BOC group) such that deprotection and salt formation are completed in one step in the presence of a strong acid (e.g., TFA).

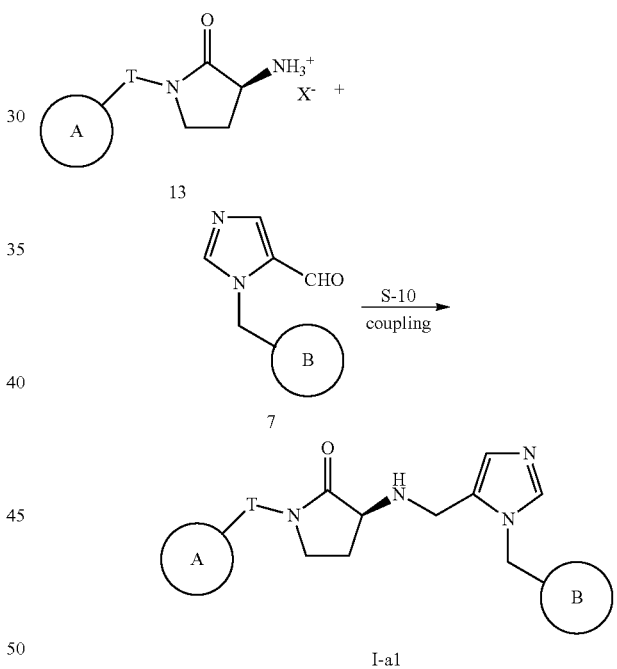

As depicted in Scheme 3, coupling partner 13 is coupled to aldehyde 7 using any of the appropriate techniques known in the chemical arts to afford product I-a1. In some embodiments, coupling occurs via reductive amination. In certain embodiments, the reductive amination is performed using a suitable reducing agent such as, for instance, a hydride reducing agent (e.g., $NaCNBH_3$).

For each of the aforementioned Schemes, it will be readily apparent to one of ordinary skill in the art that a variety of suitable reagents and reaction conditions may be employed to carry out the described syntheses.

Although preparation of formula I-a1 is depicted above, one of ordinary skill in the art would appreciate that 1-b1 can be prepared by the same methods using the appropriate chiral amino acid.

5. Compositions and Formulations:

According to certain embodiments, the present invention provides a composition comprising a provided compound, or a pharmaceutically acceptable salt thereof; and a pharmaceutically acceptable carrier, adjuvant, or vehicle. The amount of compound in provided compositions typically is such that is effective to measurably inhibit farnesylation of a target, in a biological sample or in a patient, for example when administered as part of a dosing regimen. In certain embodiments, a composition of this invention is formulated for administration to a patient in need of such composition. In some embodiments, a composition of this invention is formulated for oral administration to a patient.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a provided compound. In certain embodiments, an aforementioned formulation renders orally bioavailable a provided compound.

Methods of preparing a provided formulation or composition can include a step of bringing into association a provided compound with the carrier and, optionally, one or more accessory ingredients. In general, the formulations are prepared by uniformly and intimately bringing into association a provided compound with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a provided compound, or composition thereof, as an active ingredient. A provided compound may also be administered as a bolus, electuary or paste.

In solid dosage forms of the invention for oral administration (capsules, tablets, pills, dragees, powders, granules and the like), a provided compound, or composition thereof, is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

Tablets, and other solid dosage forms of pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of a provided compound, or composition thereof, include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral formulations can also include adjuvants such as wetting agents, emulsifying and suspending agents, sweetening, flavoring, coloring, perfuming and preservative agents.

Suspensions, in addition to a provided compound, or composition thereof, may contain one or more suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound, or composition thereof, of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a provided compound, or composition thereof, to the body. Dissolving or dispersing a compound, or composition thereof, in the proper medium can make such dosage forms. Absorption enhancers can also be used to increase the flux of compound, or composition thereof, across the skin. Either providing a rate controlling membrane or dispersing compound, or composition thereof, in a polymer matrix or gel can control the rate of such flux.

Ophthalmic formulations, eye ointments, powders, solutions and the like, are also contemplated as being within the scope of this invention.

Pharmaceutical formulations of this invention suitable for parenteral administration comprise one or more compounds, or composition thereof, of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof; vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These formulations may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissue.

In certain embodiments, a compound or pharmaceutical preparation is administered orally. In other embodiments, the compound or pharmaceutical preparation is administered intravenously. Alternative routs of administration include sublingual, intramuscular, and transdermal administrations.

When the provided compounds are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, provided compounds, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular provided compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. Preferred chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above.

Generally, doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, an effective amount comprises about 10 ng/kg of body weight to about 1000 mg/kg of body weight. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms.

While it is possible for a provided compound to be administered alone, it is preferable to administer the compound as a pharmaceutical formulation (composition) as described above.

The compounds according to the invention may be formulated for administration in any convenient way for use in human or veterinary medicine, by analogy with other pharmaceuticals.

According to the invention, compounds for treating neurodegenerative diseases, disorders, and/or conditions can be formulated or administered using methods that help the compounds cross the blood brain barrier (BBB). The vertebrate brain (and CNS) has a unique capillary system unlike that in any other organ in the body. The unique capillary system has morphologic characteristics which make up the blood-brain barrier (BBB). The blood-brain barrier acts as a system-wide cellular membrane that separates the brain interstitial space from the blood.

The unique morphologic characteristics of the brain capillaries that make up the BBB are: (a) epithelial-like high resistance tight junctions which literally cement all endothelia of brain capillaries together, and (b) scanty pinocytosis or transendothelial channels, which are abundant in endothelia of peripheral organs. Due to the unique characteristics of the blood-brain barrier, hydrophilic drugs and peptides that readily gain access to other tissues in the body are barred from entry into the brain or their rates of entry and/or accumulation in the brain are very low.

Various strategies have been developed for introducing those drugs into the brain which otherwise would not cross the blood-brain barrier. Widely used strategies involve invasive procedures where the drug is delivered directly into the brain. One such procedure is the implantation of a catheter into the ventricular system to bypass the blood-brain barrier and deliver the drug directly to the brain. These procedures have been used in the treatment of brain diseases which have a predilection for the meninges, e.g., leukemic involvement of the brain (U.S. Pat. No. 4,902,505, incorporated herein in its entirety by reference).

Although invasive procedures for the direct delivery of drugs to the brain ventricles have experienced some success, they are limited in that they may only distribute the drug to superficial areas of the brain tissues, and not to the structures deep within the brain. Further, the invasive procedures are potentially harmful to the patient.

Other approaches to circumventing the blood-brain barrier utilize pharmacologic-based procedures involving drug latentiation or the conversion of hydrophilic drugs into lipid-soluble drugs. The majority of the latentiation approaches involve blocking the hydroxyl, carboxyl and primary amine groups on the drug to make it more lipid-soluble and therefore more easily able to cross the blood-brain barrier.

Another approach to increasing the permeability of the BBB to drugs involves the intra-arterial infusion of hypertonic substances which transiently open the blood-brain barrier to allow passage of hydrophilic drugs. However, hypertonic substances are potentially toxic and may damage the blood-brain barrier.

Peptide compositions of the invention may be administered using chimeric peptides wherein the hydrophilic peptide drug is conjugated to a transportable peptide, capable of crossing the blood-brain barrier by transcytosis at a much higher rate than the hydrophilic peptides alone. Suitable transportable peptides include, but are not limited to, histone, insulin, transferrin, insulin-like growth factor I (IGF-I), insulin-like growth factor II (IGF-II), basic albumin and prolactin.

Antibodies are another method for delivery of compositions of the invention. For example, an antibody that is reactive with a transferrin receptor present on a brain capillary endothelial cell, can be conjugated to a neuropharmaceutical agent to produce an antibody-neuropharmaceutical agent conjugate (U.S. Pat. No. 5,004,697, incorporated herein in its entirety by reference). The method is conducted under conditions whereby the antibody binds to the transferrin receptor on the brain capillary endothelial cell and the neuropharmaceutical agent is transferred across the blood brain barrier in a pharmaceutically active form. The uptake or transport of antibodies into the brain can also be greatly increased by cationizing the antibodies to form cationized antibodies having an isoelectric point of between about 8.0 to 11.0 (U.S. Pat. No. 5,527,527, incorporated herein in its entirety by reference).

A ligand-neuropharmaceutical agent fusion protein is another method useful for delivery of compositions to a host (U.S. Pat. No. 5,977,307, incorporated herein in its entirety by reference). The ligand is reactive with a brain capillary endothelial cell receptor. The method is conducted under conditions whereby the ligand binds to the receptor on a brain capillary endothelial cell and the neuropharmaceutical agent is transferred across the blood brain barrier in a pharmaceutically active form. In some embodiments, a ligand-neuropharmaceutical agent fusion protein, which has both ligand binding and neuropharmaceutical characteristics, can be produced as a contiguous protein by using genetic engineering techniques. Gene constructs can be prepared comprising DNA encoding the ligand fused to DNA encoding the protein, polypeptide or peptide to be delivered across the blood brain barrier. The ligand coding sequence and the agent coding sequence are inserted in the expression vectors in a suitable manner for proper expression of the desired fusion protein. The gene fusion is expressed as a contiguous protein molecule containing both a ligand portion and a neuropharmaceutical agent portion.

Permeability of the blood brain barrier can often be increased by administering a blood brain barrier agonist, for example bradykinin (U.S. Pat. No. 5,112,596, incorporated herein in its entirety by reference), or polypeptides called receptor mediated permeabilizers (RMP) (U.S. Pat. No. 5,268,164, incorporated herein in its entirety by reference). Exogenous molecules can be administered to the host's bloodstream parenterally by subcutaneous, intravenous or intramuscular injection or by absorption through a bodily tissue, such as the digestive tract, the respiratory system or the skin. The form in which the molecule is administered (e.g., capsule, tablet, solution, emulsion) depends, at least in part, on the route by which it is administered. Administration of the exogenous molecule to the host's bloodstream and the intravenous injection of the agonist of blood-brain barrier permeability can occur simultaneously or sequentially in time.

For example, a therapeutic drug can be administered orally in tablet form while the intravenous administration of an agonist of blood-brain barrier permeability is given later (e.g., between 30 minutes later and several hours later). This allows time for the drug to be absorbed in the gastrointestinal tract and taken up by the bloodstream before the agonist is given to increase the permeability of the blood-brain barrier to the drug. On the other hand, an agonist of blood-brain barrier permeability (e.g., bradykinin) can be administered before or at the same time as an intravenous injection of a drug. Thus, the term "co-administration" is used herein to mean that the agonist of blood-brain barrier and the exogenous molecule will be administered at times that will achieve significant concentrations in the blood for producing the simultaneous effects of increasing the permeability of the blood-brain barrier and allowing the maximum passage of the exogenous molecule from the blood to the cells of the central nervous system.

In other embodiments, compounds of the invention can be formulated as a prodrug with a fatty acid carrier (and optionally with another neuroactive drug). The prodrug is stable in the environment of both the stomach and the bloodstream and may be delivered by ingestion. The prodrug passes readily through the blood brain barrier. The prodrug preferably has a brain penetration index of at least two times the brain penetration index of the drug alone. Once in the central nervous system, the prodrug, which preferably is inactive, is hydrolyzed into the fatty acid carrier and the farnesyl transferase inhibitor (and optionally another drug). The carrier preferably is a normal component of the central nervous system and is inactive and harmless. The compound and/or drug, once released from the fatty acid carrier, is active. Preferably, the fatty acid carrier is a partially-saturated straight chain molecule having between about 16 and 26 carbon atoms, and more preferably 20 and 24 carbon atoms. Examples of fatty acid carriers are provided in U.S. Pat. Nos. 4,939,174; 4,933,324; 5,994,932; 6,107,499; 6,258,836; and 6,407,137.

6. Combination Therapy

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated".

In certain embodiments of the present invention, compounds provided herein may be administered in combination with one or more additional therapeutic agents. Such additional therapeutic agents may be administered separately from an inventive compound-containing composition, as part of a multiple dosage regimen. Alternatively or additionally, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination", "combined", and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a provided compound, an additional therapeutic agent, and a pharmaceutically acceptable carrier, adjuvant, or vehicle. Two or more agents are typically considered to be administered "in combination" when a patient or individual is simultaneously exposed to both agents. In many embodiments, two or more agents are considered to be administered "in combination" when a patient or individual simultaneously shows therapeutically relevant levels of the agents in a particular target tissue or sample (e.g., in brain, in serum, etc).

The amount of both a provided compound and additional therapeutic agent (in those compositions which comprise an additional therapeutic agent as described above)) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In some embodiments of the invention, agents that are utilized in combination may act synergistically. Therefore, the amount of either agent utilized in such situations may be less than that typically utilized or required in a monotherapy involving only that therapeutic agent. Commonly, a dosage of between 0.01-1,000 µg/kg body weight/day of the additional therapeutic agent can be administered.

The amount of additional therapeutic agent present utilized in combination therapy according to the present invention typically will be no more than the amount that would normally be administered in a composition comprising that therapeutic agent as the only active agent. Preferably the amount of additional therapeutic agent utilized will range from about 50% to 100% of the amount normally utilized in therapies involving that agent as the only therapeutically active agent. Established dosing regimens for known therapeutic agents are known in the art and incorporated herein by reference.

For example, compounds of the present invention, or pharmaceutically acceptable compositions thereof, can be administered in combination with treatments for Alzheimer's disease such as ARICEPT® and EXCELON®. In some embodiments, provided compositions and formulations may be administered in combination with one or more treatments for Parkinson's Disease such as ABT-126 (Abbott Laboratories), pozanicline (Abbott Laboratories), MABT-5102A (AC Immune), Affitope AD-01 (AFFiRiS GmbH), Affitope AD-02 (AFFiRiS GmbH), davunetide (Allon Therapeutics Inc), nilvadipine derivative (Archer Pharmaceuticals), Anapsos (ASAC Pharmaceutical International AIE), ASP-2535 (Astellas Pharma Inc), ASP-2905 (Astellas Pharma Inc), 11C-AZD-2184 (AstraZeneca plc), 11C-AZD-2995 (AstraZeneca plc), 18F-AZD-4694 (AstraZeneca plc), AV-965 (Avera Pharmaceuticals Inc), AVN-101 (Avineuro Pharmaceuticals Inc), immune globulin intravenous (Baxter International Inc), EVP-6124 (Bayer AG), nimodipine (Bayer AG), BMS-708163 (Bristol-Myers Squibb Co), CERE-110 (Ceregene Inc), CLL-502 (CLL Pharma), CAD-106 (Cytos Biotechnology AG), mimopezil ((Debiopharm SA), DCB-ADI (Development Centre for Biotechnology), EGb-761 ((Dr Willmar Schwabe GmbH & Co), E-2012 (Eisai Co Ltd), ACC-001 (Elan Corp plc), bapineuzumab (Elan Corp plc), ELND-006 (Elan Pharmaceuticals Inc), atomoxetine (Eli Lilly & Co), LY-2811376 (Eli Lilly & Co), LY-451395 (Eli Lilly & Co), m266 (Eli Lilly & Co), semagacestat (Eli Lilly & Co), solanezumab (Eli Lilly & Co), AZD-103 (Ellipsis Neurotherapeutics Inc), FULL (ENKAM Pharmaceuticals A/S), EHT-0202 (ExonHit Therapeutics SA), celecoxib (GD Searle & Co), GSK-933776A (GlaxoSmithKline plc), rosiglitazone XR (GlaxoSmithKline plc), SB-742457 (GlaxoSmithKline plc), R-1578 (Hoffmann-La Roche AG), HF-0220 (Hunter-Fleming Ltd), oxiracetam (ISF Societa Per Azioni), KD-501 (Kwang Dong Pharmaceutical Co Ltd), NGX-267 (Life Science Research Israel), huperzine A (Mayo Foundation), Dimebon (Medivation Inc), MEM-1414 (Memory Pharmaceuticals Corp), MEM-3454 (Memory Pharmaceuticals Corp), MEM-63908 (Memory Pharmaceuticals Corp), MK-0249 (Merck & Co Inc), MK-0752 (Merck & Co Inc), simvastatin (Merck & Co Inc), V-950 (Merck & Co Inc), memantine (Merz & Co GmbH), neramexane (Merz & Co GmbH), Epadel (Mochida Pharmaceutical Co Ltd), 123I-MNI-330 (Molecular Neuroimaging Llc), gantenerumab (MorphoSys AG), NIC5-15 (Mount Sinai School of Medicine), huperzine A (Neuro-Hitech Inc), OXIGON (New York University), NP-12 (Noscira SA), NP-61 (Noscira SA), rivastigmine (Novartis AG), ECT-AD (NsGene A/S), arundic acid (Ono Pharmaceutical Co Ltd), PF-3084014 (Pfizer Inc), PF-3654746 (Pfizer Inc), RQ-00000009 (Pfizer Inc), PYM-50028 (Phytopharm plc), Gero-46 (PN Gerolymatos SA), PBT-2 (Prana Biotechnology Ltd), PRX-03140 (Predix Pharmaceuticals Inc), Exebryl-1 (ProteoTech Inc), PF-4360365 (Rinat Neuroscience Corp), HuCAL anti-beta amyloid monoclonal antibodies (Roche AG), EVT-302 (Roche Holding AG), nilvadipine (Roskamp Institute), galantamine (Sanochemia Pharmazeutika AG), SAR-110894 (sanon-aventis), INM-176 (Scigenic & Scigen Harvest), mimopezil (Shanghai Institute of Materia Medica of the Chinese Academy of Sciences), NEBO-178 (Stegram Pharmaceuticals), SUVN-502 (Suven Life Sciences), TAK-065 (Takeda Pharmaceutical), ispronicline (Targacept Inc), rasagiline (Teva Pharmaceutical Industries), T-817MA (Toyama Chemical), PF-4494700 (TransTech Pharma Inc), CX-717 (University of California), 18F-FDDNP (University of California Los Angeles), GTS-21 (University of Florida), 18F-AV-133 (University of Michigan), 18F-AV-45 (University of Michigan), tetrathiomolybdate (University of Michigan), 123I-IMPY (University of Pennsylvania), 18F-AV-1/ZK (University of Pennsylvania), 11C-6-Me-BTA-1 (University of Pittsburgh), 18F-6-OH-BTA-1 (University of Pittsburgh), MCD-386 (University of Toledo), leuprolide acetate implant (Voyager Pharmaceutical Corp), aleplasinin (Wyeth), begacestat (Wyeth), GSI-136 (Wyeth), NSA-789 (Wyeth), SAM-531 (Wyeth), CTS-21166 (Zapaq), and ZSET-1446 (Zenyaku Kogyo).

Alternatively or additionally, in some embodiments, provided compositions and formulations may be administered in combination with one or more treatments for Parkinson's Disease such as L-DOPA/carbidopa, entacapone, ropinrole, pramipexole, bromocriptine, pergolide, trihexephendyl, and amantadine; For example, methods of the present invention can be used in combination with medications for treating PD. Such therapeutic agents include levodopa, carbodopa, levodopa (Sinemet and Sinemet CR), Stalevo (carbodopa, levodopa, and entacapone), anticholinergics (trihexyphenidyl, benztropine mesylate, procyclidine, artane, cogentin), bromocriptidine (Parlodel), pergolide (Permax), ropinirol (Requip), pramipexole (Mirapex), cabergoline (Dostinex), apomorphine (Apokyn), rotigotine (Neupro), Ergolide, Mirapex or Requip.

In some embodiments, provided compositions and formulations may be administered in combination with one or more treatments for Parkinson's Disease such as ACR-343, rotigotine(Schwarz), rotigotine patch (UCB), apomorphine (Amarin), apomorphine (Archimedes), AZD-3241 (Astra Zeneca), creatine (Avicena), AV-201 (Avigen), lisuride (Axxonis/Biovail), nebicapone (BIAL Group), apomorphine (Mylan), CERE-120 (Ceregene), melevodopa+carbidopa (Cita Neuropharmaceuticals), piclozotan (Daiichi), GM1 Ganglioside (Fidia Farmaceutici), Altropane (Harvard University), Fluoratec (Harvard University), fipamezole (Juvantia Pharma), istradefylline (Kyowa Hakko Kogyo), GPI-1485 (MGI GP), Neu-120 (Neurim Pharmaceuticals), NGN-9076 (NeuroGeneration Inc), NLX-P101 (Neurologix), AFQ-056 (Novartis), arundic acid (Ono/Merck & Co), COMT inhibitor (Orion), ProSavin (Oxford Biomedica), safinamide (Pharmacia & Upjohn), PYM-50028 (Phytopharm), PTX-200 (Phytix), 123I-iometopane (Research Triangle Institute), SYN-115 (Roche Holding), preladenant (Schering Plough), ST-1535 (Sigma-Tau Ind. Farm), ropinirole (SmithKline Beecham), pardoprunox (Solvay), SPN-803 (Supernus Pharmaceuticals), nitisinone (Syngenta), TAK-065 (Takeda), cell therapy (Titan Pharmaceuticals), PD gene therapy (University of Auckland/Weill Medical College), 18F-AV-133 (University of Michigan), in itoquinone/mitoquinol redox mixture (Antipodean Pharmaceuticals), 99m-Tc-tropantiol (University of Pennsylvania), apomorphine (Vectura), BIIB-014 (Vernalis Group), aplindore (Wyeth), and XP-21279 (XenoPort Inc).

Alternatively or additionally, in some embodiments, provided compositions and formulations may be administered in combination with one or more treatments for Huntington's disease such as ACR-16 (A Carlsson Research AB), creatine (Avicena Group, Inc.), dimebon (Medivation, Inc.), AMR-101 (Scotia Holdings, Inc.), or glatiramer acetate (Teva Pharmaceuticals).

Alternatively or additionally, in some embodiments, provided provided compositions and formulations may be administered in combination with one or more treatments for motor neuronal disorders, such as AEOL-10150 (Aeolus Pharmaceuticals Inc), riluzole (Aventis Pharma AG), ALS-08 (Avicena Group Inc), creatine (Avicena Group Inc), arimoclomol (Biorex Research and Development Co), mecobalamin (Eisai Co Ltd), talampanel (Eli Lilly & Co), R-7010 (F Hoffmann-La Roche Ltd), edaravone (Mitsubishi-Tokyo Pharmaceuticals Inc), arundic acid (Ono Pharmaceutical Co Ltd), PYM-50018 (Phytopharm plc), RPI-MN (ReceptoPharm Inc), SB-509 (Sangamo BioSciences Inc), olesoxime (Trophos SA), sodium phenylbutyrate (Ucyclyd Pharma Inc), and R-pramipexole (University of Virginia).

Alternatively or additionally, in some embodiments, provided and formulations may be administered in combination with one or more treatments for Multiple Sclerosis such as laquinimod (Active Biotech AB), Alfaferone (Alfa Wassermann SpA), ATX-MS-1467 (Apitope Technology (Bristol) Ltd), Anapsos (ASAC Pharmaceutical International AIE), AZD-5904 (AstraZeneca), teriflunomide (Aventis Pharma AG), BaroFeron (BaroFold Inc), BHT-3009 (Bayhill Therapeutics Inc), Tovaxin (Baylor College of Medicine), PEGylated IFN beta 1-a (Biogen Idec Inc), abatacept (Bristol-Myers Squibb Co), BGC-20-0134 (BTG plc), alemtuzumab (Cambridge University), CCX-140 (ChemoCentryx Inc), Betaseron (Chiron Corp), DWP-419 (Daewoong Pharmaceutical), Biferonex (Dr Rentschler Biotechnologie GmbH), Oral E3 (Effective Pharmaceuticals Inc), perampanel (Eisai Co Ltd), ELND-002 (Elan Corp), fampridine (Elan Corp), natalizumab (Elan Corp plc anti IL-23 (Eli Lilly & Co), LY-2127399 (Eli Lilly & Co), FAR-404 (Farmacija doo), BG-12 (Fumapharm AG), GEM-SP (Gemac Bio), ocrelizumab (Genentech Inc), ofatumumab (Genmab A/S), GRC-4039 (Glenmark Pharmaceuticals Ltd), nabiximols (GW Pharmaceuticals), nerispirdine (Hoechst AG), rituximab (IDEC Pharmaceuticals Corp mitoxantrone (Immunex Corp), INCB-8696 (Incyte Corp), TV-1102 (Isis Pharmaceuticals Inc), BOW-304 (Kingston Scientific Partnership), ibudilast (Kyorin Pharmaceutical), KRP-203 (Kyorin Pharmaceutical), erythropoietin (Max-Planck Institute for Experimental Medicine), Rebif (Merck Serono SA), MLN-1202 (Millennium Pharmaceuticals Inc), BAF-312 (Novartis AG), ONO-4641 (Ono Pharmaceutical), VG-1000 (Oregon Health & Science University), daclizumab (PDL BioPharma Inc), Tauferon (Pepgen Corp), PI-2301 (Peptimmune), RPI-78M (ReceptoPharm Inc), CTLA4-Ig, (RepliGen Corp), CS-0777 (Sankyo), cladribine (Scripps Research Institute), firategrast (Tanabe Seiyaku), GBR-500 (Targeted Molecules Corp), glatiramer acetate (Teva Pharmaceutical Industries), CDP-323 (UCB Celltech), dirucotide (University of Alberta), recombinant chaperonin 10 (University of Queensland), fingolimod (Welfide Corp), atacicept (ZymoGenetics Inc), etc. In some embodiments, agents for treating Multiple Sclerosis (MS) include but are not limited to beta interferon (e.g., AVONEX® and REBIF®), COPAXONE®, and/or mitoxantrone, and combinations thereof.

Alternatively or additionally, provided compositions and formulations may be administered in combination with one or more treatments for lysosomal storage diseases, such as bone marrow transplant, stem cell replacement therapy, enzyme replacement therapy (e.g., with enzyme replacement with α-1-iduronidase for MPS Type I/Hurler's disease; glucocerebrosidase for Gaucher's type I or III; α-galactosidase A for Fabry's; etc), splenectomy, and/or treatment with certain therapeutic agents (e.g., a glucosylceramide synthase inhibitor such as miglustat for Gaucher's; statins and/or cholestyramine for Fabry's; etc). Particular known therapies for lysosomal storage diseases are included in the Table below:

| Lysosomal Storage Disease Therapy Table | | | |
|---|---|---|---|
| Name | Company | Action | Indication(s) |
| AGT-181 | ArmaGen Technologies Inc | Alpha-L-iduronidase stimulator | Mucopolysaccharidosis type I |
| | | Insulin receptor modulator | Lysosome storage disease |
| BMN-110 | BioMarin Pharmaceutical Inc | Sulfatase stimulator | Morquio syndrome |
| laronidase | BioMarin Pharmaceutical Inc | Alpha-L-iduronidase stimulator | Mucopolysaccharidosis type I; Lysosome storage disease |
| NZ-1002 | Novazyme Pharmaceuticals Inc | Unspecified enzyme modulator | Lysosome storage disease |
| recombinant human N-acetylgalactosamine-6-sulfatase (mucopolysaccharidosis IVA), Vivendy | Vivendy Therapeutics Ltd | Sulfatase stimulator | Morquio syndrome |
| glycan inhibitor (mucopolysaccharidosis), Zacharon | Zacharon Pharmaceuticals Inc | Glycosaminoglycan antagonist | Mucopolysaccharidosis |
| lysosomal acid lipase, LSBC | Childrens Hospital Medical Center (Cincinnati) | Lipase modulator | Hypercholesterolemia |
| | | Lipid metabolism modulator | Atherosclerosis |
| gene therapy (lysosomal storage disorders), Genzyme/Targeted Genetics | Genovo Inc | Unspecified virus based gene therapy | Lysosome storage disease |
| Genz-112638 | Genzyme General | Glycolipid inhibitor | Gaucher disease |
| | | Glucosylceramide synthase inhibitor | Lysosome storage disease |
| HTI-501 | Halozyme Therapeutics Inc | Protease stimulator | Dermatological disease |
| | | Dermatological agent | |
| lysosomal arylsulfatase A replacement therapy (FGE, metachromatic leukodystrophy), Shire | Shire Human Genetic Therapies Inc | Arylsulfatase A stimulator | Metachromatic leukodystrophy |

Lysosomal Storage Disease Therapy Table

| Name | Company | Action | Indication(s) |
| --- | --- | --- | --- |
| HGT-1111 | Zymenex A/S | Arylsulfatase A stimulator | Metachromatic leukodystrophy |
| arylsulfatase B gene therapy (MPS-VI), | Freiburg University | Albert-Ludwigs-Universitaet Freiburg | Arylsulfatase B stimulator |
| AAV-GUS | Avigen Inc | Gene therapy | Storage disease |
| BMN-110 | BioMarin Pharmaceutical Inc | Sulfatase stimulator | Morquio syndrome |
| galsulfase | BioMarin Pharmaceutical Inc | Arylsulfatase B stimulator | Maroteaux-Lamy syndrome |
| | | Glycosaminoglycan antagonist | Lysosome storage disease |
| migalastat | Amicus Therapeutics Inc | Alpha-galactosidase stimulator | Fabry disease |
| AAV-alpha galactosidase A gene therapy (Fabry disease), Genzyme | Genzyme Corp | Adenovirus based gene therapy | Fabry disease |
| alpha-galactosidase A, LSBC | Large Scale Biology Corp | Alpha-galactosidase modulator | Fabry disease |
| PRX-102 | Protalix BioTherapeutics Inc | Alpha-galactosidase stimulator | Fabry disease |
| alpha-galactosidase A, Orphan | Research Corporation Technologies | Alpha-galactosidase stimulator | Fabry disease |
| agalsidase alfa | Shire Human Genetic Therapies Inc | Alpha-galactosidase stimulator | Fabry disease |
| afegostat tartrate | Amicus Therapeutics Inc | Glucosylceramidase stimulator | Gaucher disease |
| AAV gene therapy (Gaucher), Avigen | Avigen Inc | Adeno-associated virus based gene therapy | Gaucher disease |
| Gaucher's disease therapy, Neuraltus | Neuraltus Pharmaceuticals Inc | Glucosylceramidase stimulator | Gaucher disease |

Other examples of agents the inhibitors of this invention may also be combined with include, without limitation: chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, camptothecin, cisplatin, metronidazole, and Gleevec™, among others. In other embodiments, a compound of the present invention is administered in combination with a biologic agent, such as Avastin or Vectibix.

In certain embodiments, compounds of the present invention, or a pharmaceutically acceptable composition thereof, are administered in combination with an antiproliferative or chemotherapeutic agent selected from any one or more of Abarelix, aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, Irinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, and/or Zoledronic acid.

In certain embodiments, compounds of the present invention, or a pharmaceutically acceptable composition thereof, are administered in combination with anti-inflammatory agents such as corticosteroids, TNF blockers, IL-1 RA, azathioprine, cyclophosphamide, sulfasalazine, methotrexate hydroxychlorogine, gold, penicillamine, azathioprine, sulfasalazine, and/or biologic drugs.

In certain embodiments, compounds of the present invention, or a pharmaceutically acceptable composition thereof, are administered in combination within aspirin and/or other nonsteroidal anti-inflammatory drugs (NSAIDs), such as ibuprofen (Motrin, and others), naproxen (Naprosyn, and others) and/or dicolfenac (Voltaren). Nonacetylated salicylates, such as sodium salicylate, salsalate (Disalcid, and others), and/or choline magnesium salicylate (Trilisate, and others), do not interfere with platelet function and may be safer than acetylated salicylates for aspirin-sensitive patients.

In certain embodiments, compounds of the present invention, or a pharmaceutically acceptable composition thereof, are administered in combination with agents for treating cardiovascular disease such as beta-blockers, ACE inhibitors, diuretics, nitrates, calcium channel blockers, and/or statins;

Additional therapeutic agents for administration in combination with a provided composition of formulation thereof, include: treatments for asthma such as albuterol and Singulair®; agents for treating schizophrenia such as zyprexa, risperdal, seroquel, and haloperidol; immunomodulatory and immunosuppressive agents such as cyclosporin, tacrolimus, rapamycin, mycophenolate mofetil, interferons, corticosteroids, cyclophophamide, azathioprine, and sulfasalazine; agents for treating liver disease such as corticosteroids, cholestyramine, interferons, and anti-viral agents; agents for treating blood disorders such as corticosteroids, anti-leukemic agents, and growth factors; and/or agents for treating immunodeficiency disorders such as gamma globulin.

Compounds or compositions of the present invention can also be used in combination with surgical therapies for the treatment of PD. Surgical treatment is presently recommended for those who have failed medical management of PD. Unilateral thallamotomy can be used to reduce tremor. It is occasionally considered for patients with unilateral tremor not responding to medication. Bilateral procedures are not advised. Unilateral deep brain stimulation of the thalamus for tremor may also be a benefit for tremor. Unilateral pallidotomy is an effective technique for reducing contralateral drug-induced dyskinesias. Gamma knife surgery—thalamotomy or pallidotomy—can be performed as a radiological alternative to conventional surgery. The currently preferred neurosurgical intervention is, however, bilateral subthalamic nucleus stimulation. Neurotransplantation strategies remain experimental. In addition to surgery and medication, physical therapy in Parkinsonism maintains muscle tone, flexibility, and improves posture and gait. In some embodiments, the method of the invention further comprises administering to the subject an amount of one or more non-farnesyl transferase inhibitor compounds effective to treat the proteinopathy.

In some embodiments, the method of the invention further comprises administering to the subject an amount of one or more non-farnesyl transferase inhibitor compounds effective to treat the neurodegenerative disease.

In some embodiments, the method of the invention, further comprises administering to the subject an amount of one or more non-farnesyl transferase inhibitor compounds effective to treat the synucleinopathy.

In some embodiments, the method of the invention further comprises administering to the subject an amount of one or more non-farnesyl transferase inihibtor compounds, wherein each non-farnesyl transferase inhibitor compound is selected from the group consisting of dopamine agonist, DOPA decarboxylase inhibitor, dopamine precursor, monoamine oxidase blocker, cathechol O-methyl transferase inhibitor, anticholinergic, and NMDA antagonist.

In some embodiments, the method of the invention further comprises administering to the subject an amount of one or more dopamine agonists, wherein said dopamine agonist is selected from the group consisting of apomorphine hydrochloride (APO-GO®), bromocriptine mesylate (PARLODEL®), cabergoline (CABASER®, DOSTINEX®), pergolide mesilate (CELANCE®), pramipexole dihydrochloride (MIRAPEXIN®), ropinirole hydrochloride (REQUIP®), rotigotine (NEUPRO®), and combinations thereof.

In some embodiments, the method of the invention further comprises administering to the subject an amount of one or more agents selected from the group consisting of one or more treatments for Parkinson's Disease such as L-DOPA/carbidopa, entacapone, ropinrole, pramipexole, bromocriptine, pergolide, trihexephendyl, and amantadine; For example, methods of the present invention can be used in combination with medications for treating PD. Such therapeutic agents include levodopa, carbodopa, levodopa (Sinemet and Sinemet CR), Stalevo (carbodopa, levodopa, and entacapone), anticholinergics (trihyxphenidyl, benztropine mesylate, procyclidine, artane, cogentin), bromocriptidine (Parlodel), pergolide (Permax), ropinirol (Requip), pramipexole (Mirapex), cabergoline (Dostinex), apomorphine (Apokyn), rotigotine (Neupro), Ergolide, Mirapex or Requip.

In some embodiments, the method of the invention further comprises administering to the subject an amount of one or more non-farnesyl transferase compounds effective to treat the amyloidopathy.

In some embodiments, the method of the invention further comprises administering to the subject an amount of one or more non-farnesyl transferase inhibitor compounds effective to treat the taupathy.

In some embodiments, the method of the invention further comprises administering to the subject an amount of one or more non-farnesyl transferase inhibitor compounds, wherein the non-farnesyl transferase inhibitor is Memantine.

In some embodiments, the method of the invention further comprises administering to the subject an amount of one or more non-farnesyl transferase inhibitor compounds, wherein each non-farnesyl trasferase inhibitor compound is selected from the group consisting of Aricept and other acetylcholinesterase inhibitors.

7. Uses of Provided Compounds and Pharmaceutical Compositions Thereof

Provided compounds and/or compositions may be utilized in any of a variety of therapeutic or other contexts. In some embodiments, for example, provided compounds and/or compositions are utilized in the treatment of one or more neurodegenerative disorders. In some embodiments, provided compounds and/or compositions are utilized in the treatment of one or more inflammatory disorders. In certain embodiments, provided compounds and/or compositions are utilized in the treatment of one or more cardiovascular disorders. In certain embodiments, provided compounds and/or compositions are utilized in the treatment of one or more proliferative disorders. In some embodiments, provided compounds and/or compositions are utilized in the treatment of one or more proteinopathies (e.g., synucleinopathies, tauopathies, amyloidopathies, TDP-42 proteinopathies, etc.). In some embodiments, provided compounds and/or compositions are utilized in the treatment of one or more diseases, disorders, or conditions resulting from disruptions of cellular autophagy. In some embodiments, provided compounds and/or compositions are utilized in the treatment of diabetes or obesity. In some embodiments, provided compounds and/or compositions are utilized in the treatment of myopathies.

Compounds and/or compositions provided herein may be administered prophylactically or therapeutically. When provided prophylactically, compounds and/or compositions are provided in advance of symptoms. Prophylactic administration may, for example, delay onset of and/or reduce rate of onset of one or more symptoms the agent serves to prevent or reduce the rate of onset of symptoms of a neurodegenerative disease. When provided therapeutically, compounds and/or compositions are provided at (or after) the onset of the appearance of one or more symptoms. In some embodiments, the therapeutic administration may, for example, reduce severity, incidence, and/or duration of one or more symptoms.

Without wishing to be bound by any particular theory, it is proposed that beneficial (e.g., therapeutic) effects of compounds described herein may be at least partly attributable to activity of the compounds as inhibitors of farnesylation. As discussed herein, in some embodiments, provided compounds are characterized by (and/or administered under conditions and/or according to a regimen that achieves) inhibition of farnesylation of at least one favored target protein.

Alternatively or additionally, and also without wishing to be bound by any particular theory, it is proposed that beneficial (e.g., therapeutic) effects of compounds provided herein may be at least partly attributable to activity of the compounds as stimulators of protein degradation, particularly with respect to misfolded and/or aggregated proteins.

It is specifically proposed that compounds provided herein are useful in the treatment of disorders, diseases, or conditions associated with abnormal protein folding and/or accumulation of protein aggregates. It will be appreciated that in some embodiments, misfolded proteins, and/or protein aggregates may be considered to cause one or more symptoms or attributes of a particular disease, disorder or condition. So long as presence of misfolded proteins and/or protein aggregates correlates with presence of symptoms, the disease, disorder, or condition is considered to be associated with misfolded proteins and/or protein aggregates. Diseases, disorders or conditions associated with misfolded and/or aggregated proteins are referred to as "proteinopathies" herein. Proteinopathies of particular relevance include those associated with protein aggregates, and particularly with aggregataes of one or more proteins selected from the group consisting of α-synuclein (synucleinopathies), tau (tauopathies), amyloid (amyloidopathies), SOD1 (SOD1 proteinopathies), TDP-43 (TDP-43 proteinopathies), huntingtin, subunit c of ATP synthase, etc. It will be appreciated by those of ordinary skill in the art that certain diseases, disorders and conditions may be associated with misfolding and/or aggregation of more than one different protein and therefore may fall into more than one disease category as described herein.

Synucleins are small proteins (123 to 143 amino acids) characterized by repetitive imperfect repeats KTKEGV (SEQ ID NO: 1) distributed throughout most of the amino terminal half of the polypeptide in the acidic carboxy-terminal region. There are three human synuclein proteins termed α, β, and γ, and they are encoded by separate genes mapped to chromosomes 4221.3-q22, 5q23, and 10q23.2-q23.3, respectively. The most recently cloned synuclein protein synoretin, has a close homology to γ-synuclein and is predominantly expressed within the retina. α-Synuclein, also referred to as non-amyloid component of senile plaques precursor protein (NACP), SYN1 or synelfin, is a heat-stable, "natively unfolded" protein of poorly defined function. It is predominantly expressed in the central nervous system (CNS) neurons where it is localized to presynaptic terminals. Electron microscopy studies have localized α-synuclein in close proximity to synaptic vesicles at axonal termini, suggesting a role for α-synuclein in neurotransmission or synaptic organization, and biochemical analysis has revealed that a small fraction of α-synuclein may be associated with vesicular membranes but most α-synuclein is cytosolic.

Genetic and histopathological evidence supports the idea that α-synuclein is the major component of several proteinaceous inclusions characteristic of specific neurodegenerative diseases. Pathological synuclein aggregations are restricted to the α-synuclein isoforms, as β- and γ-synucieins have not been detected in these inclusions. The presence of α-synuclein positive aggregates is disease specific. Lewy bodies, neuronal fibrous cytoplasmic inclusions that are histopathological hallmarks of Parkinson's disease (PD) and diffuse Lewy body disease (DLBD) are strongly labeled with antibodies to α-synuclein. Dystrophic ubiquitin-positive neurites associated with PD pathology, termed Lewy neurites (LN) and CA2/CA3 ubiquitin neurites are also α-synuclein positive. Furthermore, pale bodies, putative precursors of LBs, thread-like structures in the perikarya of slightly swollen neurons and glial silver positive inclusions in the midbrains of patients with LB diseases are also immunoreactive for α-synuclein. α-Synuclein is likely the major component of glial cell inclusions (GCIs) and neuronal cytoplasmic inclusions in MSA and brain iron accumulation type 1 (PANK1). α-Synuclein immunoreactivity is present in some dystrophic neurites in senile plaques in Alzheimer's Disease (AD) and in the cord and cortex in amyotrophic lateral sclerosis (ALS). α-Synuclein immunoreactivity is prominent in transgenic and toxin-induced mouse models of PD, AD, ALS, and HD.

Further evidence supports the notion that α-synuclein is the actual building block of the fibrillary components of LBs, LNs, and GCIs. Immunoelectron microscopic studies have demonstrated that these fibrils are intensely labeled with α-synuclein antibodies in situ. Sarcosyl-insoluble α-synuclein filaments with straight and twisted morphologies can also be observed in extracts of DLBD and MSA brains. Moreover, α-synuclein can assemble in vitro into elongated homopolymers with similar widths as sarcosyl-insoluble fibrils or filaments visualized in situ. Polymerization is associated with a concomitant change in secondary structure from random coil to anti-parallel β-sheet structure consistent with the Thioflavine-S reactivity of these filaments. Furthermore, the PD-association with α-synuclein mutation, A53T, may accelerate this process, as recombinant A53T α-synuclein has a greater propensity to polymerize than wild-type α-synuclein. This mutation also affects the ultrastructure of the polymers; the filaments are slightly wider and are more twisted in appearance, as if assembled from two protofilaments. The A30P mutation may also modestly increase the propensity of α-synuclein to polymerize, but the pathological effects of this mutation also may be related to its reduced binding to vesicles. Interestingly, carboxyl-terminally truncated α-synuclein may be more prone to form filaments than the full-length protein.

Synucleinopathies are a diverse set of disorders that share a common association with lesions containing abnormal aggregates of insolution α-synuclein protein. Typically such lesions are found in selectively vulnerable populations of neurons and glia. Certain evidence links the formation of abnormal filamentous aggregates to the onset and progression of clinical symptoms and the degeneration of affected brain regions in neurodegenerative disorders including Parkinson's disease (PD), diffuse Lewy body disease (DLBD), multiple system atrophy (MSA), and disorders of brain iron concentration including pantothenate kinase-associated neurodegeneration (e.g., PANK1). The current treatment options for these diseases include symptomatic medications such as carbidopa-levodopa, anticholinergics, and monoamine oxidase inhibitors, with widely variable benefit. Even for the best responders, i.e., patients with idiopathic Parkinson's disease, an initial good response to levodopa is typically overshadowed by drug-induced complications such as motor fluctuations and debilitating dyskinesia, following the first five to seven years of therapy. For the rest of the disorders, the current medications offer marginal symptomatic benefit. Given the severe debilitating nature of these disorders and their prevalence, there is a clear need in the art for novel approaches towards treating and managing synucleinopathies.

The present invention provides methods relevant to synucleinopathies. For example, in some embodiments, the present invention provides a method of reducing α-synuclein toxicity in a cell, the method comprising administering to a cell a therapeutically effective amount of a provided compound. In some embodiments, the present invention provides a method of reducing the accumulation of α-synuclein in a cell, the method comprising administering to a cell a therapeutically effective amount of a provided compound. In some embodiments, the cell is a neuronal cell. In some embodiments, the cell expresses α-synuclein. In certain embodiments, the synucleinopathy is Parkinson's disease, diffuse Lewy body disease, and/or multiple system atrophy disorder.

The present invention provides methods relevant to amyloidopathies. For example, in some embodiments, the present invention provides a method of reducing amyloid beta toxicity in a cell, the method comprising administering to a cell a therapeutically effective amount of a provided compound. In some embodiments, the present invention provides a method of reducing the accumulation of amyloid beta proteins in a cell, the method comprising administering to a cell a therapeutically effective amount of a provided compound. In some embodiments, the cell is a neuronal cell. In some embodiments, the cell expresses amyloid beta proteins. In certain embodiments, the amyloidopathy is Alzheimer's disease, vascular dementia, and/or cognitive impairment.

Taupathies are neurodegenerative disorders characterized by the presence of filamentous deposits, consisting of hyperphosphorylated tau protein, in neurons and glia. Abnormal tau phosphorylation and deposition in neurons and glial cells is one of the major features in taupathies. The term tauopathy, was first used to describe a family with frontotemporal dementia (FTD) and abundant tau deposits. This term is now used to identify a group of diseases with widespread tau pathology in which tau accumulation appears to be directly associated with pathogenesis. Major neurodegenerative taupathies includes sporadic and hereditary diseases characterized by filamentous tau deposits in brain and spinal cord.

In the majority of taupathies, glial and neuronal tau inclusions are the sole or predominant CNS lesions. Exemplary such taupathies include amytrophic lateral sclerosis (ALS), parkinsonism, argyrophilic grain dementia, diffuse neurofibrillary tangles with calcification, frontotemporal dementia linked to chromosome 17, corticobasal degeneration, Pick's disease, progressive supranuclear palsy, progressive subcortical gliosis, and tangle only dementia.

Additionally, taupathies characterize a large group of diseases, disorders and conditions in which significant filaments and aggregates of tau protein are found. Exemplary such diseases, disorders, and conditions include sporadic and/or familial Alzheimer's Disease (AD), amyotrophic lateral sclerosis/parkinsonism-dementia complex (ALS-FTDP), argyrophilic grain dementia, dementia pugilistica, diffuse neurofibrillary tangles with calcification, Down syndrome, frontotemporal dementia, parkinsonism linked to chromosome 17 (FTDP-17), Gerstmann-Straussler-Scheinker disease, Hallervorden-Spatz disease, inclusion body myositis, Creutzfeld-Jakob disease (CJD), multiple system atrophy, Niemann-Pick disease (NPC), Pick's disease, prion protein cerebral amyloid angiopathy, progressive supranuclear palsy (PSP), subacute sclerosing panencephalitis, tangle-predominant Alzheimer's disease, corticobasal degeneration, (CBD), myotonic dystrophy, non-guanamian motor neuron disease with neurofibrillary tangles, postencephalitic parkinsonism, prion protein cerebral amyloid angiopathy, progressive subcortical gliosis, subacute sclerosing panencephalitis, and tangle-only dementia.

Neurodegenerative diseases where tau pathology is found in conjunction with other abnormal protein lesions may be considered secondary taupathies. Examples include Alzheimer's Disease (AD) and certain diseases where prion protein, Bri, or α-synuclein are aggregated. Although tau is probably not the initial pathological factor, tau aggregates contribute to the final degeneration.

Tau deposits can also be found in several other neurodegenerative diseases in which tau pathology is evident in conjunction with other abnormal protein lesions protein. Abundant cytoplasmic inclusions consisting of aggregated hyperphosphorylated protein tau are a characteristic pathological observation in several neurodegenerative disorders such as Alzheimer's disease, Pick's disease, frontotemporal dementia, cortico-basal degeneration, and progressive supranuclear palsy.

The present invention provides methods relevant to tauopathies. For example, in some embodiments, the present invention provides a method of reducing tau toxicity in a cell, the method comprising administering to a cell a therapeutically effective amount of a provided compound. In some embodiments, the present invention provides a method of reducing the accumulation of tau proteins in a cell, the method comprising administering to a cell a therapeutically effective amount of a provided compound. In some embodiments, the cell is a neuronal cell. In some embodiments, the cell expresses tau proteins. In certain embodiments, the taupathy is Alzheimer's disease.

Certain particular diseases, disorders and conditions of interest are highlighted below.

Neurodegenerative Disease, Cognitive Impairment, and Dementia

The invention provides methods of treating neurodegenerative disease, cognitive impairment and dementia, wherein the methods comprise administering a compound of the invention or a pharmaceutically acceptable salt thereof to a subject. Many neurodegenerative diseases are linked to intracellular and/or extracellular accumulation of specific protein aggregates. In many cases, it is thought that these aggregates exert toxic effects on the brain, and contribute to disease pathology.

In one aspect, the present invention provides methods for treating a subject with a neurodegenerative diseases by administering a therapeutically effective amount of a provided compound or a composition thereof. In certain embodiments, the subject has a synucleinopathy, amyloidopathy, taupathy or other proteinopathy. In some embodiments the neurodegenerative disease is selected from the group consisting of Parkinson's disease, diffuse Lewy body disease, and multiple system atrophy disorder. In some embodiments, the subject suffers from one or more disorders of brain iron concentration including pantothenate kinase-associated neurodegeneration (e.g., PANK1). In some embodiments, other neurodegenerative diseases such as amyotrophic lateral sclerosis (ALS), Huntington's Disease (HD), Mild Cognitive Impairment, and Alzheimer's Disease (AD) may be treated with provided compounds.

Alzheimer's Disease

The invention provides methods of treating Alzheimer's disease, wherein the methods comprise administering a compound of the invention or a pharmaceutically acceptable salt thereof to a subject. Alzheimer's is the leading cause of dementia and cognitive impairment in the elderly and a leading cause of death in developing nations after cardiovascular disease, cancer, and stroke. Up to 70% of cases of dementia are due to Alzheimer's disease, with vascular disease being the second most common cause. The frequency of AD among 60-year-olds is approximately 1%. The incidence of AD doubles approximately every 5 years. Forsyth, *Phys. Ther.* 78:1325-1331, 1998; Evans et al., *JAMA* 262:2551-2556, 1989. AD afflicts an estimated four million people in the U.S. alone at a cost of $100 billion per year. Schumock, *J. Health Syst. Pharm.* 55(52):17-21, 1998; Hay & Ernst, *Am. J. Public Health* 77:1169-1175, 1987.

Alzheimer's Disease is characterized by the deterioration of mental faculties (e.g., memory loss, confusion, loss of visual/spatial comprehension) and associated with both amyloidopathies and taupathies. The central role of the long form of amyloid beta-peptide, in particular Aβ(1-42), in Alzheimer's disease has been established through a variety of histopathological, genetic and biochemical studies. Specifically, it has been found that deposition in the brain of Aβ(1-42) is an early and invariant feature of all forms of Alzheimer's disease. This occurs before a diagnosis of Alzheimer's disease is possible and before the deposition of the shorter primary form of A-beta, Aβ(1-40). Further implication of Aβ(1-42) in disease etiology comes from the observation that mutations in presenilin (gamma secretase) genes associated with early onset familial forms of Alzheimer's disease uniformly result in increased levels of Aβ(1-42). Additional mutations in the amyloid precursor protein APP raise total Aβ and in some cases raise Aβ(1-42) alone. Although the various APP mutations may influence the type, quantity, and location of Aβ deposited, it has been found that the predominant and initial species deposited in the brain parenchyma is long Aβ. In early deposits of Aβ, when most deposited protein is in the form of amorphous or diffuse plaques, virtually all of the Aβ is of the long form. These initial deposits of Aβ(1-42) then are able to seed the further deposition of both long and short forms of A. In transgenic animals expressing Aβ, deposits were associated with elevated levels of Aβ(1-42), and the pattern of deposition is similar to that seen in human disease with Aβ(1-42) being deposited early followed by deposition of Aβ(1-40). Similar patterns and timing of deposition are seen in Down's Syndrome patients in which Aβ expression is elevated and deposition is accelerated. The association of Alzheimer's Diseases with amyloid plaques means that Alzheimer's Disease is considered to be an amyloidopathy. Alzheimer's Disease is also associated with accumulation of tau aggregates and therefore is a tauopathy.

Parkinson's Disease

The invention provides methods of treating Parkinson's disease, wherein the methods comprise administering a compound of the invention or pharmaceutically acceptable salt thereof to a subject. Parkinson's disease (PD) is a neurodegenerative disorder characterized by bradykinesia, rigidity, tremor, and postural instability. The pathologic hallmark of PD is loss of neurons in the substantia nigra pars compacta (SNpc) and the appearance of Lewy bodies in remaining neurons. It appears that more than about 50% of the cells in the SNpc need to be lost before motor symptoms appear. Associated symptoms often include small handwriting (micrographia), seborrhea, orthostatic hypotension, urinary difficulties, constipation and other gastrointestinal dysfunction, sleep disorders, depression and other neuropsychiatric phenomena, dementia, and smelling disturbances (occurs early). Patients with Parkinsonism have greater mortality, about two times compared to general population without PD. This is attributed to greater frailty or reduced mobility.

Diagnosis of PD is mainly clinical and is based on the clinical findings listed above. Parkinsonism, refers to any combination of two of bradykinesia, rigidity, and/or tremor. PD is the most common cause of parkinsonism. Other causes of parkinsonism are side effects of drugs, mainly the major tranquilizers, such as Haldol, strokes involving the basal ganglia, and other neurodegenerative disorders, such as Diffuse Lewy Body Disease (DLBD), progressive supranuclear palsy (PSP), frontotemporal dementia (FTD), MSA, and Huntington's disease. The pathological hallmark of PD is the Lewy body, an intracytoplasmatic inclusion body typically seen in affected neurons of the substantia nigra and to a variable extent, in the cortex. Recently, α-synuclein has been identified as the main component of Lewy bodies in sporadic Parkinsonism.

Although parkinsonism can be clearly traced to viruses, stroke, or toxins in a few individuals, for the most part, the etiology of Parkinson's disease in any particular case is unknown. Environmental influences which may contribute to PD may include drinking well water, farming and industrial exposure to heavy metals (e.g., iron, zinc, copper, mercury, magnesium and manganese), alkylated phosphates, and orthonal chlorines. Paraquat (a herbicide) has also been associated with increased prevalence of Parkinsonism including PD. Cigarette smoking is associated with a decreased incidence of PD. The current consensus is that PD may either be caused by an uncommon toxin combined with high genetic susceptibility or a common toxin combined with relatively low genetic susceptibility.

A small percentage of subjects that are at risk of developing PD can be identified for example by genetic analysis. There is good evidence for certain genetic factors being associated with PD. Large pedigrees of autosomal dominantly inherited PDs have been reported. For example, a mutation in α-synuclein is responsible for one pedigree and triplication of the SNCA gene (the gene coding for α-synuclein) is associated with PD in others.

Multiple System Atrophy

The invention provides methods of treating multiple system atrophy, wherein the methods comprise administering a compound of the invention or a pharmaceutically acceptable salt thereof to a subject. Multiple System Atrophy (MSA) is a neurodegenerative disease marked by a combination of symptoms; affecting movement, cognition, autonomic and other body functions, hence the label "multiple system atrophy". The cause of MSA is unknown. Symptoms of MSA vary in distribution of onset and severity from person to person. Because of this, the nomenclature initially included three distinct terms: Shy-Drager syndrome, striatonigral degeneration (SD), and olivopontocerebellar atrophy (OPCA).

In Shy-Drager syndrome, the most prominent symptoms are those involving the autonomic system; blood pressure, urinary function, and other functions not involving conscious control. Striatonigral degeneration causes Parkinsonism symptoms, such as slowed movements and rigidity, while OPCA principally affects balance, coordination and speech. The symptoms for MSA can also include orthostatic hypertension, male impotence, urinary difficulties, constipation, speech and swallowing difficulties, and blurred vision.

The initial diagnosis of MSA is usually made by carefully interviewing the patient and performing a physical examination. Several types of brain imaging, including computer tomography, scans, magnetic resonance imaging (MRI), and positron emission tomography (PET), can be used as corroborative studies. An incomplete and relatively poor response to dopamine replacement therapy, such as Sinemet, may be a clue that the presentation of bradykinesia and rigidity (parkinsonism) is not due to PD. A characteristic involvement of multiple brain systems with prominent autonomic dysfunction is a defining feature of MSA and one that at autopsy confirms the diagnosis. Patients with MSA can have the presence of glial cytoplasmic inclusions in certain types of brain cells, as well. Prototypic Lewy bodies are not present in MSA. However, α-synuclein staining by immunohistochemistry is prominent. In comparison to Parkinson's, in addition to the poor response to Sinemet, there are a few other observations that are strongly suggested for MSA, such as postural instability, low blood pressure on standing (orthostatic hypotension) and high blood pressure when lying down, urinary difficulties, impotence, constipation, speech and swallowing difficulties out of proportion to slowness and rigidity.

Methods of the present invention can be used in combination with one or more alternative medications for treating MSA. Typically, the drugs that can be used to treat various symptoms of MSA become less effective as the disease progresses. Levodopa and dopamine agonists used to treat PD are sometimes effective for the slowness and rigidity of MSA. Orthostatic hypertension can be improved with cortisone, midodrine, or other drugs that raise blood pressure. Male impotence may be treated with penile implants or drugs. Incontinence may be treated with medication or catheterization. Constipation may improve with increased dietary fiber or laxatives.

Cognitive Impairment, Dementia, etc.

The invention includes methods of treating cognitive impairment and dementia, wherein the methods comprise administering a compound of the invention or pharmaceutically acceptable salt thereof to a subject. Cognitive impairment and dementia are highly prevalent neurological conditions associated with any of a variety of diseases, disorders, and conditions. Dementia is commonly defined as a progressive decline in cognitive function due to damage or disease in the body beyond what is expected from normal aging.

Without wishing to be bound by any particular theory, it is proposed that one toxic effect of accumulated protein aggregates in the brain may be the development of cognitive impairment and/or dementia.

In one aspect, the present invention provides a method of treating a cognitive impairment in a subject suffering therefrom, the method comprising administering to a subject a provided compound in a therapeutically effective amount. The cognitive impairment may be due to any of a variety of etiologies, including, but not limited to, atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia.

In certain embodiments, the cognitive impairment being treated is associated with DLBD. DLBD is the second most common cause of neurodegenerative dementia in older people, it effects 7% of the general population older than 65 years and 30% of those aged over 80 years. It is part of a range of clinical presentations that share a neurotic pathology based on normal aggregation of the synaptic protein α-synuclein. DLBD has many of the clinical and pathological characteristics of the dementia that occurs during the course of Parkinson's disease. A "one year rule" can been used to separate DLBD from PD. According to this rule, onset of dementia within 12 months of Parkinsonism qualifies as DLBD, whereas more than 12 months of Parkinsonism before onset of dementia qualifies as PD. The central features of DLBD include progressive cognitive decline of sufficient magnitude to interfere with normal social and occupational function. Prominent or persistent memory impairment does not necessarily occur in the early stages, but it is evident with progression in most cases. Deficits on tests of attention and of frontal cortical skills and visual spatial ability can be especially prominent. According to the present invention, the term "synucleinopathic subject" also encompasses a subject that is affected by, or is at risk of developing DLBD. These subjects can be readily identified by persons of ordinary skill in the art by symptomatic diagnosis or by genetic screening, brain scans, SPECT, PET imaging etc.

Core diagnostic features, two of which are essential for diagnosis of probable and one for possible DLBD are fluctuating cognition with pronounced variations in attention and alertness, recurrent visual hallucinations that are typically well-formed and detailed, and spontaneous features of Parkinsonism. In addition, there can be some supportive features, such as repeated falls, syncope, transient loss of consciousness, neuroleptic sensitivity, systematized delusions, hallucinations and other modalities, REM sleep behavior disorder, and depression. Patients with DLBD do better than those with Alzheimer's Disease in tests of verbal memory, but worse on visual performance tests. This profile can be maintained across the range of severity of the disease, but can be harder to recognize in the later stages owing to global difficulties. DLBD typically presents with recurring episodes of confusion on a background of progressive deterioration. Patients with DLBD show a combination of cortical and subcortical neuropsychological impairments with substantial attention deficits and prominent frontal subcortical and visual spatial dysfunction. These help differentiate this disorder from Alzheimer's disease.

Rapid eye movement (REM), sleep behavior disorder is a parasomnia manifested by vivid and frightening dreams associated with simple or complex motor behavior during REM sleep. This disorder is frequently associated with the synucleinopathies, DLBD, PD, and MSA, but it rarely occurs in amyloidopathies and taupathies. The neuropsychological pattern of impairment in REM sleep behavior disorder/dementia is similar to that reported in DLBD and qualitatively different from that reported in Alzheimer's disease. Neuropathological studies of REM sleep behavior disorder associated with neurodegenerative disorder have shown Lewy body disease or multiple system atrophy. REM sleep wakefulness disassociations (REM sleep behavior disorder, daytime hypersomnolence, hallucinations, cataplexy) characteristic of narcolepsy can explain several features of DLBD, as well as PD. Sleep disorders could contribute to the fluctuations typical of DLBD, and their treatment can improve fluctuations and quality of life. Subjects at risk of developing DLBD can be identified. Repeated falls, syncope, transient loss of consciousness, and depression are common in older people with cognitive impairment and can serve as (a red flag) to a possible diagnosis of DLBD. By contrast, narcoleptic sensitivity in REM sleep behavior disorder can be highly predictive of DLBD. Their detection depends on the clinicians having a high index of suspicion and asking appropriate screening questions.

Clinical diagnosis of synucleinopathic subjects that are affected by or at risk of developing LBD can be supported by neuroimaging investigations. Changes associated with DLBD include preservation of hippocampal, and medialtemporal lobe volume on MRI and occipital hypoperfusion on SPECT. Other features, such as generalized atrophy, white matter changes, and rates of progression of whole brain atrophy are not helpful in differential diagnosis. Dopamine transporter loss in the caudate and putamen, a marker of nigrostriatal degeneration, can be detected by dopamenergic SPECT and can prove helpful in clinical differential diagnosis. A sensitivity of 83% and specificity of 100% has been reported for an abnormal scan with an autopsy diagnosis of DLBD.

Consensus criteria for diagnosing DLBD include ubiquitin immunohistochemistry for Lewy body identification and staging into three categories; brain stem predominant, limbic, or neocortical, depending on the numbers and distribution of Lewy bodies. The recently-developed α-synuclein immunohistochemistry can visualize more Lewy bodies and is also better at indicating previously under recognized neurotic pathology, termed Lewy neurites. Use of antibodies to α-synuclein moves the diagnostic rating for many DLBD cases from brain stem and limbic groups into the neocortical group.

In most patients with DLBD, there are no genetic mutations in the α-synuclein or other Parkinson's disease-associated genes. Pathological up-regulation of normal, wild-type α-synuclein due to increased mRNA expression is a possible mechanism, or Lewy bodies may form because α-synuclein becomes insoluble or more able to aggregate. Another possibility is that α-synuclein is abnormally processed, for example, by a dysfunctional proteasome system and that toxic "proto fibrils" are therefore produced. Sequestering of these toxic fibrils into Lewy bodies could reflect an effort by the neurons to combat biological stress inside the cell, rather than their simply being neurodegenerative debris.

Target symptoms for the accurate diagnosis of DLBD can include extrapyramidal motor features, cognitive impairment, neuropsychiatric features (including hallucinations, depression, sleep disorder, and associated behavioral disturbances), or autonomic dysfunction.

Methods of the invention can be used in combination with one or more other medications for treating DLBD. For example, the lowest acceptable doses of levodopa can be used to treat DLBD. D2-receptor antagonists, particularly traditional neuroleptic agents, can provoke severe sensitivity reactions in DLBD subjects with an increase in mortality of two to three times. Cholinsterase inhibitors discussed above are also used in the treatment of DLBD.

In certain embodiments, the cognitive impairment being treated is associated with Alzheimer's disease.

In certain embodiments, the cognitive impairment is associated with a psychiatric disorder (e.g., schizophrenia).

In certain embodiments, the cognitive impairment being treated is associated with a genetic disease.

In certain embodiments, the cognitive impairment being treated is associated with an infectious disease (e.g., HIV, syphillis). In certain embodiments, the cognitive impairment is due to a proteinopathy. In certain embodiments, the proteinopathy is a neurodegenerative, proliferative, inflammatory, or cardiovascular disease, condition, or disorder. Exemplary proteinopathies include, for instance, α-synucleinopathy, amyloidopathy, and/or taupathies.

The present invention provides methods for treating a subject with cognitive impairment, including a step of administering to the subject a therapeutically effective amount of a provided compound or composition thereof. In certain embodiments, the subject is a mammal. In certain specific embodiments, the subject is a human. The human may be male or female, and the human may be at any stage of development.

The present invention further provides methods for treating a cognitive impairment in a subject suffering therefrom, the method comprising administering to a subject a provided compound in a therapeutically effective amount.

The present invention further provides methods for treating depression in a subject suffering therefrom, the method comprising administering to a subject a provided compound in a therapeutically effective amount.

The present invention further provides methods for treating anxiety in a subject suffering therefrom, the method comprising administering to a subject a provided compound in a therapeutically effective amount.

The present invention provides methods for treating cognitive impairment, depression, and anxiety using a provided compound. In some embodiments, said compound is an inhibitor of farnesyl transferase.

Dementia is commonly defined as a progressive decline in cognitive function due to damage or disease in the body beyond what is expected from normal aging. Dementia is described as a loss of mental function, involving problems with memory, reasoning, attention, language, and problem solving. Higher level functions are typically affected first. Dementia interferes with a person's ability to function in normal daily life. The present invention includes a method of treating vascular dementia.

Depression

The present invention provides methods of treating depression, wherein the methods comprises administering a compound of the invention or a pharmaceutically acceptable salt thereof to a subject. Depression refers to a subject that is diagnosed with, affected by, or at risk of developing depression. Based on the treatment of a transgenic mouse overexpressing Tau with a farnesyl transferase inhibitor, reduced Tau transgene-induced depression was seen in the treated mice indicated by an increase in struggling and decreased floating in the forced swim test as compared to control animals. In addition, FTI-treated mice overexpressing TAU displayed behavior similar to non-transgenic animals. The treated mice also showed reduced phosphorylated TAU in the amygdala.

Anxiety

The present invention provides methods of treating anxiety, wherein the method comprises administering a compound of the invention or a pharmaceutically acceptable salt thereof to a subject. Anxiety refers to a subject that is diagnosed with, affected by, or at risk of developing a state of apprehension and psychic tension occurring in some forms of mental disorder/s. The anxiety state may stem from a variety of causes. Based on mouse studies, farnesyl transferase inhibitors may be used as anxiolytics.

Inflammatory Disease

The invention provides methods of treating inflammatory disease, wherein the method comprises administering a compound of the invention or a pharmaceutically acceptable salt thereof. The mammalian immune system provides a means for the recognition and elimination of foreign pathogens. While the immune system normally provides a line of defense against foreign pathogens, there are many instances where the immune response itself is involved in the progression of disease. Exemplary of diseases caused or worsened by the host's own immune response are autoimmune diseases such as multiple sclerosis, lupus erythematosus, psoriasis, pulmonary fibrosis, and rheumatoid arthritis and diseases in which the immune response contributes to pathogenesis such as atherosclerosis, inflammatory diseases, osteomyelitis, ulcerative colitis, Crohn's disease, and graft versus host disease (GVHD) often resulting in organ transplant rejection. Additional exemplary inflammatory disease states include fibromyalgia, osteoarthritis, sarcoidosis, systemic sclerosis, Sjogren's syndrome, inflammations of the skin (e.g., psoriasis), glomerulonephritis, proliferative retinopathy, restenosis, and chronic inflammations.

In certain embodiments, inflammatory diseases, disorders, and conditions may include one or more of inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, irrtiable bowel syndrome (IBD), ulcerative colitis, glomerulonephritis, dermatomyositis, scleroderma, vasculitis, allergic disorders including asthma such as bronchial, allergic, intrinsic, extrinsic and dust asthma, particularly chronic or inveterate asthma (e.g. late asthma airways hyper-responsiveness) and bronchitis, chronic obstructive pulmonary disease (COPD), multiple sclerosis, rheumatoid arthritis, disorders of the gastrointestinal tract, including, without limitation, Coeliac disease, proctitis, eosinophilic gastro-enteritis, mastocytosis, pancreatitis, Crohn's disease, ulcerative colitis, food-related allergies which have effects remote from the gut, e.g. migraine, rhinitis and eczema. Conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia, acute pancreatitis, chronic pancreatitis, and adult respiratory distress syndrome, and/or acute inflammatory responses (such as acute respiratory distress syndrome and ischemia/reperfusion injury).

Cardiovascular Disease

The invention provides methods of treating cardiovascular disease, wherein the methods comprise administering a compound of the invention or a pharmaceutically acceptable salt thereof to a subject. Cardiovascular disease is the leading killer in America today. Over 50 million Americans have heart and cardiovascular related problems. By the time that cardiovascular heart problems are usually detected, the disease is usually quite advanced, having progressed for decades, and often too advanced to allow successful prevention of major permanent disability.

In some embodiments, cardiovascular disease may be a disease which involves the heart and/or blood vessels, arteries, and occasionally veins. In some embodiments, the disease is a vascular disease. These problems are most commonly due to consequences of arterial disease, atherosclerosis, atheroma, but also can be related to infection, valvular and clotting problems.

Exemplary particular cardiovascular diseases, disorders and conditions may include one or more of myocardial ischemia, myocardial infarction, vascular hyperplasia, cardiac hypertrophy, congestive heart failure, cardiomegaly, restenosis, atherosclerosis, hypertension, and/or angina pectoris.

In certain embodiments, the cardiovascular disease, disorder or condition is atherosclerosis, a coronary heart disease, an acute coronary symptom, unstable angina pectoris or acute myocardial infarction, stable angina pectoris, stroke, ischemic stroke, inflammation or autoimmune disease associated artheriosclerosis or restenosis.

Traumatic Brain Injury

The present invention provides methods of treating traumatic brain injury, wherein the methods comprise administering a compound or pharmaceutically acceptable salt thereof. Traumatic brain injury (TBI, also called intracranial injury) occurs when an external force traumatically injures the brain. TBI can be classified based on severity, mechanism (closed or penetrating head injury), or other features (e.g. occurring in a specific location or over a widespread area). Head injury usually refers to TBI, but is a broader category because it can involve damage to structures other than the brain, such as the scalp and skull.

TBI is a major cause of death and disability worldwide, especially in children and young adults. Causes include falls, vehicle accidents, and violence. Brain trauma can be caused by a direct impact or by acceleration alone. In addition to the damage caused at the moment of injury, brain trauma causes secondary injury, a variety of events that take place in the minutes and days following the injury. These processes, which include alterations in cerebral blood flow and the pressure within the skull, contribute substantially to the damage from the initial injury.

The physical forces resulting in a TBI may cause their effects by inducing three types of injury: skull fracture, parenchymal injury, and vascular injury. Parenchymal injuries include concussion, direct parenchymal injury and diffuse axonal injury. Concussions are characterized as a clinical syndrome of alteration of consciousness secondary to head injury typically resulting from a change in the momentum of the head (movement of the head arrested against a ridged surface). The pathogenesis of sudden disruption of nervous activity is unknown, but the biochemical and physiological abnormalities that occur include, for example, depolarization due to excitatory amino acid-mediated ionic fluxes across cell membranes, depletion of mitochondria (adenosine triphosphate, and alteration in vascular permeability. Postconcussive syndrome may show evidence of direct parenchymal injury, but in some cases there is no evidence of damage.

Contusion and lacerations are conditions in which direct parenchymal injury of the brain has occurred, either through transmission of kinetic energy to the brain and bruising analogous to what is seen in soft tissue (contusion) or by penetration of an object and tearing of tissue (laceration). A blow to the surface of the brain leads to rapid tissue displacement, disruption of vascular channels, and subsequent hemorrhage, tissue injury and edema. Morphological evidence of injury in the neuronal cell body includes pyknosis of nucleus, eosinophilia of the cytoplasm, and disintegration of the cell. Furthermore, axonal swelling can develop in the vicinity of damage neurons and also at great distances away from the site of impact. The inflammatory response to the injured tissue follows its usual course with neutrophiles preceding the appearance of macrophages.

As described herein, autophagy is a homeostatic process for recycling of proteins and organelles that increases during times of nutrient deprivation and is regulated by reactive oxygen species. Autophagy has been shown to be induced after traumatic brain injury in mice (Clark, R S, Autophagy, 2008 Jan. 1; 4(1):88-90). Zhang et al. has shown that autophagy was still increased in surviving cells at the injury site one month after traumatic brain injury (Zhang Y B, Neurosci Bull 2008, 24:143-149). Without wishing to be bound by theory, one hypothesis is that autophagy is activated upon injury to the brain and might protect neurons from degeneration after traumatic brain injury while cells undergoing necrotic or apoptotic death (and possibly involving autophagy in its detrimental role) would likely have disappeared. The timing of inhibition of autophagy—early or late after a traumatic brain injury may have different outcomes. In one aspect of the invention, autophagy is inhibited early after a traumatic brain injury e.g., within 1, 2, 3, 4, 5, 6, 7, 8, 12, 24, 36, 48 hours after traumatic brain injury. In another aspect of the invention, autophagy is inhibited late after a traumatic brain injury e.g., after a month; after several days; after 1, 2, 3, 4, 5, 7, 14, 21, 30 days.

Administration of compound for the treatment of traumatic brain injury may be performed by many methods known in the art. The present invention comprises all forms of dose administration including, but not limited to, systemic injection, parenteral administration, intravenous, intraperitoneal, intramuscular, transdermal, buccal, subcutaneous and intracerebroventricular administration. Alternatively, a compound of the invention may be administered directly into the brain or cerebrospinal fluid by any intracerebroventricular technique including, for example, lateral cerebro ventricular injection, lumbar puncture or a surgically inserted shunt into the cerebro ventricle of a patient. Methods of administering may be by dose or by control release vehicles.

The treatment of a traumatic brain injury can be monitored by employing a variety of neurological measurements. For example, a partial therapeutic responses can be monitored by determining if, for example, there is an improvement in the subjects a) maximum daily Glasgow Coma Score; b) duration of coma; 3) daily intracranial pressure—therapeutic intensity levels; 4) extent of cerebral edema/mass effect measured on serial CT scans; and, 5) duration of ventilator support.

The invention includes a method of treating a traumatic brain injury, wherein the method comprises administering a compound of the invention or a pharmaceutically acceptable salt thereof, to a subject. In one aspect, the compound is administered in amount sufficient to improve mitochondrial health in said subject.

Proliferative Disease

The invention provides methods of treating proliferative disease, wherein the proliferative disease comprises administering a compound of the invention or a pharmaceutically acceptable salt thereof to a subject. In general, cell proliferative disorders, diseases or conditions encompass a variety of conditions characterized by aberrant cell growth, preferably abnormally increased cellular proliferation. For example, cell proliferative disorders, diseases, or conditions include, but are not limited to, cancer, immune-mediated responses and diseases (e.g., transplant rejection, graft vs host disease, immune reaction to gene therapy, autoimmune diseases, pathogen-induced immune dysregulation, etc.), certain circulatory diseases, and certain neurodegenerative diseases.

In certain embodiments, the invention relates to methods of treating cancer. In general, cancer is a group of diseases which are characterized by uncontrolled growth and spread of abnormal cells. Examples of such diseases are carcinomas, sarcomas, leukemias, lymphomas and the like.

For example, cancers include, but are not limited to leukemias and lymphomas such as cutaneous T-cell lymphomas (CTCL), peripheral T-cell lymphomas, lymphomas associated with human T-cell lymphotropic virus (HTLV) such as adult T-cell leukemia/lymphoma (ATLL), B-cell lymphoma, acute lymphocytic leukemia, acute nonlymphocytic leukemias, chronic lymphocytic leukemia, chronic myelogenous leukemia, acute myelogenous leukemia, Hodgkin's disease, non-Hodgkin's lymphomas, multiple myeloma, myelodysplastic syndrome, mesothelioma, common solid tumors of adults such as head and neck cancers (e.g., oral, laryngeal and esophageal), genitourinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer, and/or childhood solid tumors such as brain tumors, neuroblastoma, retinoblastoma, Wilms' tumor, bone tumors, and soft-tissue sarcomas.

In some embodiments, the invention relates to treatment of leukemias. For example, in some embodiments, the invention relates to treatment of chronic lymphocytic leukemia, chronic myelogenous leukemia, acute lymphocytic leukemia, acute myelogenous leukemia, and/or adult T cell leukemia/lymphoma. In certain embodiments, the invention relates to the treatment of AML. In certain embodiments, the invention relates to the treatment of ALL. In certain embodiments, the invention relates to the treatment of CML. In certain embodiments, the invention relates to the treatment of CLL.

In some embodiments, the invention relates to treatment of lymphomas. For example, in some embodiments, the invention relates to treatment of Hodgkin's or non-Hodgkin's (e.g., T-cell lymphomas such as peripheral T-cell lymphomas, cutaneous T-cell lymphomas, etc.) lymphoma.

In some embodiments, the invention relates to the treatment of myelomas and/or myelodysplastic syndromes. In some embodiments, the invention relates to treatment of solid tumors. In some such embodiments the invention relates to treatment of solid tumors such as lung, breast, colon, liver, pancreas, renal, prostate, ovarian, and/or brain. In some embodiments, the invention relates to treatment of pancreatic cancer. In some embodiments, the invention relates to treatment of renal cancer. In some embodiments, the invention relates to treatment of prostate cancer. In some embodiments, the invention relates to treatment of sarcomas. In some embodiments, the invention relates to treatment of soft tissue sarcomas. In some embodiments, the invention relates to methods of treating one or more immune-mediated responses and diseases.

For example, in some embodiments, the invention relates to treatment of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; treatment of graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves' disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treatment of infectious diseases causing aberrant immune response and/or activation, such as traumatic or pathogen induced immune dysregulation, including for example, that which are caused by hepatitis B and C infections, HIV, *Staphylococcus aureus* infection, viral encephalitis, sepsis, parasitic diseases wherein damage is induced by an inflammatory response (e.g., leprosy). In some embodiments, the invention relates to treatment of graft vs host disease (especially with allogenic cells), rheumatoid arthritis, systemic lupus erythematosus, psoriasis, atopic dermatitis, Crohn's disease, ulcerative colitis and/or multiple sclerosis.

Alternatively or additionally, in some embodiments, the invention relates to treatment of an immune response associated with a gene therapy treatment, such as the introduction of foreign genes into autologous cells and expression of the encoded product. In some embodiments, the invention relates to treatment of circulatory diseases, such as arteriosclerosis, atherosclerosis, vasculitis, polyarteritis nodosa and/or myocarditis.

Lysosomal Storage Disease

The invention provides methods of treating lysosomal storage disease, wherein the methods comprise administering a compound of the invention or a pharmaceutically acceptable salt thereof to subject. Lysosomal Storage diseases are a group of disorders which are characterized by a defect in any aspect of lysosomal biology, which in turn prevents the degradation of lipids, proteins or organelles by the lysosome, or which prevents the proper trafficking of molecules into or out of the lysosome, or which prevents lysosome-mediated signalling. These diseases typically include neurological involvement which can be (though not always) progressive and degenerative; symptoms may include developmental delay, ataxia, visual problems, seizures etc. The lysosome, when healthy, processes unwanted material into substances that can be utilized by cells. Lysosomal storage diseases typically result when one or more of the enzymes involved in this processing is or becomes defective or absent. Defect or absence of such an enzyme results in accumulation of unwanted material in cells, eventually damaging the cells. Most lysosomal storage diseases are genetic diseases that show autosomal recessive inheritance; some (e.g., Fabry disease and Hunter syndrome) are X-linked.

Representative lysosomal storage diseases include, for example, Activator Deficiency/GM2 Gangliosidosis, Alpha-mannosidosis, Aspartylglucosaminuria, Cholesteryl ester storage disease, Chronic Hexosarnimidase A Deficiency, Cystinosis, Danon disease, Fabry disease, Farber disease, Fucosidosis, Galactosialidosis, Gaucher Disease (e.g., Type I, Type II, Type III), GM1 gangliosidosis (e.g., Infantile, Late infantile/Juvenile, Adult/Chronic), I-Cell disease/Mucolipidosis II, Infantile Free Sialic Acid Storage Disease/ISSD, Juvenile Hexosaminidase A Deficiency, Krabbe disease (e.g., Infantile Onset, Late Onset), Metachromatic Leukodystrophy, Mucopolysaccharidoses disorders, Pseudo-Hurler polydystrophy/Mucolipidosis IIIA (e.g., MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease (e.g., Type A, Type B, Type C), Neuronal Ceroid Lipofuscinoses (e.g., CLN6 disease—Atypical Late Infantile, Late Onset variant, Early Juvenile, Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis), Pompe disease/Glycogen storage disease type II, Pycnodysostosis, Sandhoff disease/GM2 Gangliosidosis (e.g., Adult Onset, Infantile, Juvenile), Schindler disease, Salla disease/Sialic Acid Storage Disease, Tay-Sachs/GM2 gangliosidosis, Wolman disease, etc.

Lysosomal Storage diseases can result from a number of defects, including a primary defect in a lysosomal enzyme's activity, eg as in Gaucher disease or Fabry disease, or a defect the post-translational processing of a lysosomal enzyme eg as in Mucosuphatidosis, or a defect in the trafficking of a lysosomal enzyme eg as in Mucolipidosis type IIIA, or a defect in a lysosomal protein that is not an enzyme eg as in Danon disease, or a defect in a non-lysosomal protein eg as in a variant of Late Infantile Neuronal Ceroid Lipofuscinosis. In Lysosomal Storage disorders, there is often an accumulation of certain lipids e.g. glucosylceramide or cholesterol, or of certain proteins eg subunit c of ATP synthase, or of certain damaged organelles or organelle fragments eg fragmented mitochondria. Drug-induced stimulation of a cellular phagic response may be of therapeutic benefit in Lysosomal Storage disorders; such phagic responses may include microautophagy, macroautophagy, chaperone-mediated autophagy, mitophagy, and pexophagy.

Representative lysosomal storage diseases include, for example, Activator Deficiency/GM2 Gangliosidosis, Alpha-mannosidosis, Aspartylglucosaminuria, beta-mannosidosis, carbohydrate-deficient glycoprotein syndrome, Cholesteryl ester storage disease, Chronic Hexosaminidase A Deficiency, cobalamin definiciency type F, Cystinosis, Danon disease, Fabry disease, Farber disease, Fucosidosis, Galactosialidosis, Gaucher Disease (e.g., Type I, Type II, Type III), GM1 gangliosidosis (e.g., Infantile, Late infantile/Juvenile, Adult/Chronic), $GM_1$ gangliosidosis, $GM_2$ gangliosidosis, $GM_3$ gangliosidosis, glycogen storage disease type II, I-Cell disease/Mucolipidosis II, Infantile Free Sialic Acid Storage Disease/ISSD, Juvenile Hexosaminidase A Deficiency, Kanzaki disease, Krabbe disease (e.g., Infantile Onset, Late Onset), lactosylceramidosis, Metachromatic Leukodystrophy, Mucopolysaccharidoses disorders, Pseudo-Hurler polydystrophy/Mucolipidosis IIIA (e.g., MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease (e.g., Type A, Type B, Type C), Neuronal Ceroid Lipofuscinoses (e.g., CLN6 disease—Atypical Late Infantile, Late Onset variant, Early Juvenile, Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis), Pompe disease/Glycogen storage disease type II, Pompe disease, Pycnodysostosis, Sandhoff disease/GM2 Gangliosidosis (e.g., Adult Onset, Infantile, Juvenile), Schindler disease, Salla disease/Sialic Acid Storage Disease, sialic acid storage disease, sialidosis, Tay-Sachs/GM2 gangliosidosis, or Wolman disease.

Myopathy

The invention provides methods of treating myopathy, wherein the methods comprise administering a compound or the invention or a pharmaceutically acceptable salt thereof to a subject. The term autophagy is derived from the Greek words "autos" and "phago" meaning "self eating". Autophagy takes place in the lysosomes and it refers to a process of metabolic degradation of cellular components and expulsion of the by-products to the cytoplasm. Autophagy takes place at basal levels in all eukaryotic cells turning over long-lived macromolecules and large supramolecular structures including whole organelles to rejuvenate their function. In addition, autophagy can be upregulated during metabolic, genotoxic or hypoxic stress conditions and acts as an adaptive mechanism essential for cell survival. Regulation and modulation of autophagy has recently attracted attention as this process has been implicated in diseases and disorders that may be considered a proteinopathy including: aging, cancer, infection, cardiovascular disease, neurodegenerative disease, muscular disorders (myopathies), diabetes mellitus, obesity, and others.

The three muscle types found in mammals, skeletal muscle, cardiac muscle and smooth muscle, together make up the major sites of metabolic activity. Skeletal muscle is the most abundant tissue in the human body and the major reservoir of protein as a source of amino acids to be utilized as energy by various other organs during catabolic periods. Protein degradation in muscle tissue is controlled by two major proteolytic systems: the ubiquitin proteosome and the autophagy lysosome. Both of these degradation pathways are activated during catabolic disease states, for example cancer, AIDS, diabetes, and organ failure and may contribute to muscular atrophy, both muscle loss and weakness. The role of autophagy in regulating muscle mass is clear, but the exact mechanism/s is/are yet to be revealed.

Dysfunctional autophagy has been linked to several different muscle disorders, or generally described as myopathies. For example, it is believed that the pathology observed in muscle disorders such as Danons disease and Pompes disease is at least partly a result of impaired autophagosome fusion with lysosomes thereby inhibiting lysosome dependent degradation. Another example is inclusion body myopathy Paget's frontotemporal lobe dementia (IBMPFD), which is characterized by mutations in p97/VCP gene. Patients with IBMPFD have degenerating muscle fibres, rimmed vacuoles, and sarcoplasmic inclusions containing ubiquitin and TDP-43. In addition, IBMPFD muscle accumulates autophagosome-associated proteins such as LC3 and p62.90% of these patients win develop disabling weakness by the fourth to fifth decade. Autophagy has also been recently shown to be required to maintain muscle mass. Genetic deletion of autophagic genes in muscle of mice resulted in profound muscle atrophy and age-dependent decrease in force. As used herein, the term "myopathy" refers to a disease, disorder, and/or condition of skeletal muscle that is not caused by nerve disorders. Myopathies cause the skeletal or voluntary muscles to become weak or shrunken (atrophied).

Autophagic vacuolar myopathies can be considered a group of diseases that could be classified in either lysosomal storage disease or neuromuscular disorders. Autophagic vacuolar myopathies are characterized by the abnormal accumulation of lysosomes in muscle fibers resulting in clinical signs and symptoms of myopathy.

Autophagic mediated myopathy includes myopathies associated with rimmed vacuoles. Rimmed vacuoles are aggregates of autophagosomes found predominantly in atrophic muscle fibers. The aggregates may contain amyloid and cathepsins as well as other proteins. Rimmed vacuole myopathy includes: Nonake myopathy or distal myopathy with rimmed vacuoles (DRMV), inclusion body myopathy 2 (IBM2).

Skeletal Muscle Myopathy

Myopathies, generally, refer to a class of degenerative skeletal muscle disease that is not caused by nerve dysfunction. Myopathies cause progressive weakness and wasting away of skeletal muscles. The causes, symptoms and severity of myopathies vary. Etiologically, myopathy includes neurogenic muscular disease, hereditary forms, an inflammatory response, the result of an endocrine or metabolic disorder, drug or toxin induced, and infection induced. The different types of myopathies are classified according to their causes. Symptoms common among myopathies include weakness of the voluntary muscles of the arms, legs, and trunk, drooping upper eyelids, foot drop, facial weakness and lack of reflexes in the affected muscles. Some symptoms may be transitory. There is no effective cure or treatment for myopathies.

Due to the varying forms and causes of myopathies, determining the form of myopathy the individual patient has is crucial in providing the proper treatment. Diagnosis includes a thorough physical examination, measurement of potassium in the blood, muscle biopsies and an electromyogram (EMG). In genetically based Myopathies, the affected families are strongly advised to consult a genetic counselor.

Genetic myopathies include central core disease, centronuclear (myotubular) myopathy, myotonia congenita, nemaline myopathy, paramyotonia congenita, periodic paralysis and mitochondrial myopathies. Danon disease is a rare genetic condition causing muscle weakness (muscular dystrophy), heart disease (cardiomyopathy), and mental retardation (or learning problems). Infantile onset autophagic vacuolar myopathy (MAVIO) has been reported in infants abnormal muscle glycogen storage and severe cardiomyopathy. Genetic myopathies vary by symptoms, severity and genetic mutation. Both dominant and recessive modes of inheritance are also present. Certain forms of centronuclear myopathy, also known as myotubular myopathy, have been found to be X-linked and primarily affects males.

Neurogenic muscle disease includes neurogenic atrophy due to peripheral nerve pathology and spinal muscular atrophies.

Myopathy includes disorders of neuromuscular transmission and include non-paraneoplastic neuromuscular disease including myasthenia gravis and paraneoplastic neuromuscular disease including stiff-man syndrome, other paraneoplastic neuromuscular disorders and some forms of myasthenia gravis.

Myopathies include channelopathies and defects in ion transportation. For example, channelopathies and defects on ion transportation include inherited conditions including: hyperkalemic periodic paralysis (sodium channel), hypokalemic periodic paralysis (uncommon) (calcium channel, dihydropyridine receptor), paramyotonica congenita (sodium channel)-pure type, potassium sensitive type, myotonia congenita (including potassium sensitive type (autosomal dominant, sodium channel), Becker's generalized type (autosomal recessive, chloride channel), Thomsen's type (autosomal dominant, chloride channel), Schwartz-Jampel syndrome), malignant hyperthermia (ryanodine receptor), and myotonic dystrophy (protein kinase of sodium channel). Sporadic channelopathies and defects in ion transportation include Lambert-Eaton myasthenic syndrome.

Dystrophies (or muscular dystrophies) are a subgroup of myopathies characterized by muscle degeneration and regeneration. Clinically, muscular dystrophies are typically progressive, because the muscles' ability to regenerate is eventually lost, leading to progressive weakness, often leading to use of a wheelchair, and eventually death, usually related to respiratory weakness. Examples of dystrophies include: myotonia and neuromyotonia.

The congenital myopathies do not show evidence for either a progressive dystrophic process (i.e., muscle death) or inflammation, but instead characteristic microscopic changes are seen in association with reduced contractile ability of the muscles Other examples of specific myopathies include: myotonic dystrophy (congenital type), minimal change myopathy (non-specific congenital myopathies), central core disease, multicore (minicore) myopathy, nemaline myopathy, congenital fiber type disproportion myopathy, myotubular myopathy (centronuclear myopathy), integrin-alpha-7/beta-1 deficiency muscular dystrophy, zebra-body myopathy, hyaline body myopathy, fingerprint body myopathy, reducing body myopathy, cytoplasmic body (spheroid body) myopathy, sarcotubular myopathy, trilaminar myopathy, specific type 1 hypertrophy, cylindrical spiral myopathy, uniform type 1 fibers myopathy, vacuolar myopathy with excessive autophagic vacuoles myopathy, X-linked vacuolar myopathy with cardiomyopathy and mental retardation, mixed myopathy, and familial periodic paralysis.

Muscular dystrophies (dystrophic myopathy) can be categorized as congenital (neonatal onset) and non-congenital (non-neonatal onset). Congenital (neonatal onset) muscular dystrophy includes congenital muscular dystrophy-merosin deficient type, congenital muscular dystrophy-merosin-positive type, congenital muscular dystrophy-non-specific, facioscapulohumeral dystrophy (Landouzy-Déjerine Dystrophy), Walker-Warburg syndrome, muscle-eye-brain disease of Santavuori, Marinesco-Sjogren syndrome, Bethlehem dystrophy, Ullrich congenital muscular dystrophy. Non-congenital (non-neonatal onset) muscular dystrophies include: Duchene muscular dystrophy, Becker's muscular dystrophy, Emery-Dreifuss muscular dystrophy, facioscapulohumeral dystrophy (Landouzy-Dejerine) and facio-scapulo-humeral syndromes, limb-girdle muscular dystrophy, distal muscular dystrophies, late adult type 1 (Welander)-Autosomal dominant, late adult type 2 (Marksberry)-Autosomal dominant, early adult type 1 (Nonaka)-Autosomal recessive, early adult type 2 (Miyoshi)-Autosomal recessive, and ocular muscular dystrophy.

Rhabdomyolysis and myoglobinurias may result in myopathy. Rhabdomyolysis/necrotizing myopathy includes idiopathic recurrent myoglobinuria and hyperthermic conditions such as malignant hyperthermia and exertional heat strokes.

Myopathy may be non-drug/toxin induced, drug induced, or the result of intoxication or poisoning. For example, non-drug or toxin induced myopathy includes crush injury and torture, ischemia, physical exhaustion and overexertion, subacute riecrotizing carcinomatous myopathy. Drug induced myopathy includes high-dose corticosteroids, clofibrate, gemfibrozil, epsilon-aminocaproic acid, statin therapy, lovastatin, pravastatin, simvastatin, mevacor, and/or zidovudine (AZT). Intoxication and poisoning may induce myopathy and includes: acute alcoholic rhabdomyolysis (acute alcoholic myopathy), chronic alcoholic myopathy, colchicines associated vacuolar myopathy, cocaine, mushroom poisoning (amanita phalloides), snake venoms, vitamin E intoxication, and organophosphates.

Metabolic myopathies result from defects in biochemical metabolism that primarily affect muscle. Metabolic myopathy includes for example, hypokalemia, diabetic ketoacidosis, nonketotic hyperglycemic/hyperosmolar states, hypo-/hypernatremia, hypophosphatemia, hythyroidism, near drowning, renal tubular acidosis, pancreatitis, and Crohn's disease with elemental diet.

Myopathy may be the result of an infection for example: *legionella*, streptococci, influenza A and B, HIV among others.

Predisposing conditions that may lead to a myopathy include Duchenne's muscular distrophy, mitochondrial myopathy, and McArdle's disease.

Inflammatory myopathies are caused by problems with the immune system attacking components of the muscle, leading to signs of inflammation in the muscle. Inflammatory myopathy includes primary inflammatory myopathies (the inflammation is primarily against fibers) and includes polymyositis, dermatomyositis, inclusion body myositis, localized nodular myositis (focal myositis), myositis ossificans (familial cardioneuromyopathy with hyaline masses and nemaline masses and congenital myopathy with excess of thin myofilaments), myositis associated with connective tissue diseases, scleroderma, systemic lupus erythematosus (SLE), rheumatoid arthritis, mixed connective tissue disease, eosinophilic polymyositis, benign acute childhood myositis (BACM), (myalgia cruris epidemica). Secondary inflammatory myopathy (the inflammation is primarily not against fibers) includes non-granulomatous infection, granulomatous infection, vasculitis, and polymyositis.

Infection of the muscle may lead to myopathy and includes virus infection, bacterial infection, fungal infection, and parasitic infections including: trichinosis, cysticerosis, toxoplasmosis, sarcosporidiosis, and microsporidiosis.

Disorders of lipid metabolism may lead to myopathy and includes: carnitine deficiency, primary muscle carnitine deficiency, and deficits in carnitine-palmitoyl transferase activity.

Lysosomal storage disease may lead to myopathy and includes acid maltase deficiency myopathies (glycogen storage disease type II), Batten's disease, Fabry's disease, fucosidosis, mannosidosis, and Samdhoff's disease. Non-glycogen non-lysosomal storage disease may lead to myopathy and includes Lafora's disease. Glycogen storage disease (GSD) may lead to myopathy and includes acid maltase deficiency (Pompe's disease or GSD type II), debranching enzyme deficiency (Cori's disease, Forbe's disease or GSD type III), branching enzyme deficiency (GSD type IV), myophosphorylase deficiency (McArdle's disease or GSD type V), phosphofructokinase deficiency (Tarui's disease or GSD type VII), phosphorylase b kinase deficiency (GSD type VIII), phosphoglycerate kinase deficiency (GSD type IX), phosphogylcerate mutase deficiency (GSD type X), lactate dehydrogenase deficiency (GSD type XI), and myoadenylate (AMPD) deaminase deficiency.

Myopathy due to systemic disorders includes polymyalgia rheumatic, and carcinoma associated muscle disease (cachetic atrophy, chronic carcinomatosis myopathy, subacute necrotizing carcinomatous myopathy, and dermatomyositis associated with carcinoma).

Myopathy due to endocrine disorders includes hyper- and hypothryodism, parathyroid diseases, pituitaty disorders, Cushing's syndrome, and carcinoid myopathy.

Mitochondrial myopathies are due to defects in mitochondria, which provide a critical source of energy for muscle.

Skeletal muscle atrophy can also be categorized as a myopathy. Muscle atrophy is the decrease in the mass of muscle. The loss of muscle mass can be partial or complete and includes: disuse atrophy (a cast placed on a finger, toe or limb; or extended bed rest); sarcopenia; frailty syndrome; cachexia; Dejerine Sottas syndrome, and age-associated weakness. Muscular atrophy can also be a co-morbidity with a primary disease, for example cancer, HIV-AIDS, congestive heart failure, chronic obstructive pulmonary disease, renal failure, severe burns, cachexia, and liver failure. Others include: amyotrophic lateral sclerosis, injury, long-term corticosteroid therapy, motor neuropathy, diabetic neuropathy, muscular dystrophy, osteoarthritis, polio, rheumatoid arthritis, spinal cord injury, starvation, and cerebrovascular incident (e.g. stroke).

Cardiomyopathy

Cardiomyopathy, heart muscle disease, is the deterioration of the function of the myocardium. Indiuduals diagnosed with cardiomyopathy are often at risk for arrhythmia or sudden cardiac death or both. Broadly, cardiomyopathy can be categorized into extrinsic and ischemic disease.

Extrinsic cardiomyopathy are cardiomyopathies where the primary pathology is outside the myocardium itself. Extrinsic cardiomyopathy includes: congenital heart disease, nutritional diseases, ischemic (or non-ischaemic) cardiomyopathy, hypertensive cardiomyopathy, valvular cardiomyopathy, inflammatory cardiomyopathy, cardiomyopathy secondary to a systemic metabolic disease, alcoholic cardiomyopathy, diabetic cardiomyopathy, and restrictive cardiomyopathy. In some parts of the world, endemic disease can be an extrinsic cause of cardiomyopathy, for example, Chagas disease, which is a prevalent cause of cardiomyopathy in Central and South America.

Ischemic cardiomyopathy, generally refers to myocardial ischemia and infarction. Ischemic cardiomyopathy is a weakness in the muscle of the heart due to inadequate oxygen delivery to the myocardium with coronary artery disease being the most common cause. Anemia and sleep apnea are relatively common conditions that can contribute to ischemic myocardium and hyperthyroidism can cause a 'relative' ischemia secondary to high output heart failure. Individuals with ischemic cardiomyopathy typically have a history of myocardial infarction, although longstanding ischemia can cause enough damage to the myocardium to precipitate a clinically significant cardiomyopathy even in the absence of myocardial infarction. In a typical presentation, the area of the heart affected by a myocardial infarction will initially become necrotic as it dies, and will then be replaced by myocardial scarring (fibrosis). This fibrotic tissue is akinetic and cannot contribute to the heart's function as a pump. If the akinetic region of the heart is substantial enough, the affected side of the heart will go into failure, and this failure is the functional result of an ischemic cardiomyopathy.

An intrinsic cardiomyopathy is weakness in the muscle of the heart that is not due to an identifiable external cause. To make a diagnosis of an intrinsic cardiomyopathy, significant coronary artery disease should be ruled out. The term intrinsic cardiomyopathy does not describe the specific etiology of weakened heart muscle. The intrinsic cardiomyopathies consist of a variety of disease states, each with their own causes.

Intrinsic cardiomyopathy has a number of causes including drug and alcohol toxicity, certain infections (including Hepatitis C), and various genetic and idiopathic (i.e., unknown) causes.

Intrinsic cardiomyopathies include dilated cardiomyopathy (DCM), perpartum cardiomyopathy, hypertrophic cardiomyopathy (HCM), arrhythmogenic right ventricular cardiomyopathy (ARVC), restrictive cardiomyopathy (RCM), obliterative card iomyopathy (hypereosinophilic syndrome), and noncompaction cardiomyopathy. Many diseases can result in cardiomyopathy. These include diseases such as hemochromatosis, amyloidosis, diabetes, hyperthyroidism, lysosomal storage diseases and the muscular dystrophies.

Smooth Muscle Myopathy

Smooth muscle is an involuntary non-striated muscle, found within the tunica media layer of large and small arteries and veins, the bladder, uterus, male and female reproductive tracts, gastrointestinal tract, respiratory tract, arrector pili of skin, the ciliary muscle, and iris of the eye. The glomeruli of the kidneys contain a smooth muscle-like cell called the mesangial cell. Smooth muscle is fundamentally different from skeletal muscle and cardiac muscle in terms of structure, function, excitation-contraction coupling, and mechanism of contraction.

Anti-smooth muscle antibodies (ASMA) can be a symptom of an auto-immune disorder, such as hepatitis, cirrhosis, or lupus and may lead to smooth muscle myopathy. Vascular smooth muscle tumors include intravascular leiomyomatosis, angioleiomyoma, vascular leiomyosarcomas.

Smooth muscle myopathy includes mitochondrial-neurogastro-intestinal encephalomyopathy (MNGIE) (or pseudo-obstruction-leukoencephalopathy-intestinal-pseudoobstruction syndrome (POLIP), lipofuscinosis of the gastrointestinal tract (brown bowel syndrome).

Diabetes/Obesity

The invention provides methods of treating diabetetes or obesity, wherein the methods comprise administering a compound of the invention or a pharmaceutically acceptable salt thereof to a subject. Autophagy is essential for maintaining both survival and health of cells. Autophagy is normally suppressed by amino acids and insulin. Autophagy activity and expression of some key autophagy genes were suppressed in the presence of insulin resistance and hyperinsulinemia, two possible symptoms of diabetes. Insulin-mediated suppression of autophagy appears to involve FoxO1-mediated transcription of key autophagy genes. Accordingly, stimulation of autophagy is a potential therapeutic strategy for the treatment of diabetes.

A recent study has shown that disruption of the process that controls the amount of fat that cells store for use as a back-up energy source is a key factor in age-related metabolic diseases such as obesity and type 2 diabetes (Cuervo et al., "Autophagy regulates lipid metabolism" published in the Apr. 1, 2009 online version of Nature).

All cells store lipids, a type of fat, in the form of small droplets that can be broken down for energy when needed. In situations of excessive food intake or in certain diseases such as diabetes or obesity, these lipid droplets become so large that they interfere with normal cell function.

This study showed that the amount of fat stored in these intracellular lipid droplets was controlled through autophagy. Specifically, the lysosomes continuously removed portions of lipid droplets and processed them for energy production. When food is scarce, autophagy becomes a main source of energy for the cells and this process of digesting lipid droplets is accelerated. If autophagy slows down, as occurs in aging, the lipid droplets stored in cells keep growing and eventually become so big that they can no longer be degraded. This slowdown in fat control appears to trigger a vicious cycle in which the enlarging fat droplets impair autophagy, allowing even more fat to accumulate, and so on, which could eventually contribute to diseases such as obesity and diabetes. Thus, therapies aimed at helping autophagy operate more efficiently might prevent disease by keeping fat droplets under control.

Diabetes

Diabetes mellitus is a group of metabolic diseases characterized by hyperglycemia resulting from defects in insulin secretion, insulin action, or both. The chronic hyperglycemia of diabetes is associated with long-term damage, dysfunction, and failure of various organs, especially the eyes, kidneys, nerves, heart, and blood vessels.

Several pathogenic processes are involved in the development of diabetes. These range from autoimmune destruction of the β-cells of the pancreas with consequent insulin deficiency to abnormalities that result in resistance to insulin action. The basis of the abnormalities in carbohydrate, fat, and protein metabolism in diabetes is deficient action of insulin on target tissues. Deficient insulin action results from inadequate insulin secretion and/or diminished tissue responses to insulin at one or more points in the complex pathways of hormone action. Impairment of insulin secretion and defects in insulin action frequently coexist in the same patient, and it is often unclear which abnormality, if either alone, is the primary cause of the hyperglycemia.

Symptoms of marked hyperglycemia include polyuria, polydipsia, weight loss, sometimes with polyphagia, and blurred vision. Impairment of growth and susceptibility to certain infections may also accompany chronic hyperglycemia. Acute, life-threatening consequences of uncontrolled diabetes are hyperglycemia with ketoacidosis or the nonketotic hyperosmolar syndrome.

Long-term complications of diabetes include retinopathy with potential loss of vision; nephropathy leading to renal failure; peripheral neuropathy with risk of foot ulcers, amputations, and Charcot joints; and autonomic neuropathy causing gastrointestinal, genitourinary, and cardiovascular symptoms and sexual dysfunction. Patients with diabetes have an increased incidence of atherosclerotic cardiovascular, peripheral arterial, and cerebrovascular disease. Hypertension and abnormalities of lipoprotein metabolism are often found in indiviudals with diabetes.

The vast majority of cases of diabetes fall into two broad etiopathogenetic categories. In one category, type 1 diabetes, the cause is an absolute deficiency of insulin secretion. Individuals at increased risk of developing this type of diabetes can often be identified by serological evidence of an autoimmune pathologic process occurring in the pancreatic islets and by genetic markers. In the other, much more prevalent category, type 2 diabetes, the cause is a combination of resistance to insulin action and an inadequate compensatory insulin secretory response. In the latter category, a degree of hyperglycemia sufficient to cause pathologic and functional changes in various target tissues, but without clinical symptoms, may be present for a long period of time before diabetes is detected. During this asymptomatic period, it is possible to demonstrate an abnormality in carbohydrate metabolism by measurement of plasma glucose in the fasting state or after a challenge with an oral glucose load.

The degree of hyperglycemia (if any) may change over time, depending on the extent of the underlying disease process. A disease process may be present but may not have progressed far enough to cause hyperglycemia. The same disease process can cause impaired fasting glucose (IFG) and/or impaired glucose tolerance (IGT) without fulfilling the criteria for the diagnosis of diabetes. In some individuals with diabetes, adequate glycemic control can be achieved with weight reduction, exercise, and/or oral glucose-lowering agents. These individuals therefore do not require insulin. Other individuals who have some residual insulin secretion but require exogenous insulin for adequate glycemic control can survive without it. Individuals with extensive β-cell destruction and therefore no residual insulin secretion require insulin for survival. The severity of the metabolic abnormality can progress, regress, or stay the same. Thus, the degree of hyperglycemia reflects the severity of the underlying metabolic process and its treatment more than the nature of the process itself.

Assigning a type of diabetes to an individual often depends on the circumstances present at the time of diagnosis, and many diabetic individuals do not easily fit into a single class. For example, a person with gestational diabetes mellitus (GDM) may continue to be hyperglycemic after delivery and may be determined to have, in fact, type 2 diabetes. Alternatively, a person who acquires diabetes because of large doses of exogenous steroids may become normoglycemic once the glucocorticoids are discontinued, but then may develop diabetes many years later after recurrent episodes of pancreatitis. Another example would be a person treated with thiazides who develops diabetes years later. Because thiazides in themselves seldom cause severe hyperglycemia, such individuals probably have type 2 diabetes that is exacerbated by the drug. Thus, for the clinician and patient, it is less important to label the particular type of diabetes than it is to understand the pathogenesis of the hyperglycemia and to treat it effectively.

Immune-mediated diabetes is a form of diabetes, which accounts for only 5-10% of those with diabetes, previously encompassed by the terms insulin-dependent diabetes, type I diabetes, or juvenile-onset diabetes, results from a cellular-mediated autoimmune destruction of the β-cells of the pancreas. Markers of the immune destruction of the β-cell include islet cell autoantibodies, autoantibodies to insulin, autoantibodies to glutamic acid decarboxylase (GAD65), and autoantibodies to the tyrosine phosphatases IA-2 and IA-2β. One and usually more of these autoantibodies are present in 85-90% of individuals when fasting hyperglycemia is initially detected. Also, the disease has strong HLA associations, with linkage to the DQA and DQB genes, and it is influenced by the DRB genes. These HLA-DR/DQ alleles can be either predisposing or protective.

In this form of diabetes, the rate of β-cell destruction is quite variable, being rapid in some individuals (mainly infants and children) and slow in others (mainly adults). Some patients, particularly children and adolescents, may present ketoacidosis as the first manifestation of the disease. Others have modest fasting hyperglycemia that can rapidly change to severe hyperglycemia and/or ketoacidosis in the presence of infection or other stress. Still others, particularly adults, may retain residual β-cell function sufficient to prevent ketoacidosis for many years; such individuals eventually become dependent on insulin for survival and are at risk for ketoacidosis. At this latter stage of the disease, there is little or no insulin secretion, as manifested by low or undetectable levels of plasma C-peptide. Immune-mediated diabetes commonly occurs in childhood and adolescence, but it can occur at any age, even in the 8th and 9th decades of life.

Autoimmune destruction of β-cells has multiple genetic predispositions and is also related to environmental factors that are still poorly defined. Although patients are rarely obese when they present with this type of diabetes, the presence of obesity is not incompatible with the diagnosis. These patients are also prone to other autoimmune disorders such as Graves' disease, Hashimoto's thyroiditis, Addison's disease, vitiligo, celiac sprue, autoimmune hepatitis, myasthenia gravis, and pernicious anemia.

Some forms of type 1 diabetes have no known etiologies (idiopathic diabetes). Some of these patients have permanent insulinopenia and are prone to ketoacidosis, but have no evidence of autoimmunity. Although only a minority of patients with type 1 diabetes fall into this category, of those who do, most are of African or Asian ancestry. Individuals with this form of diabetes suffer from episodic ketoacidosis and exhibit varying degrees of insulin deficiency between episodes. This form of diabetes is strongly inherited, lacks immunological evidence for β-cell autoimmunity, and is not HLA associated. An absolute requirement for insulin replacement therapy in affected patients may not be consistent over the course of the disease.

Type 2 diabetes (ranging from predominantly insulin resistance with relative insulin deficiency to predominantly an insulin secretory defect with insulin resistance). This form of diabetes, which accounts for about 90-95% of those with diabetes, previously referred to as non-insulin-dependent diabetes, type II diabetes, or adult-onset diabetes, encompasses individuals who have insulin resistance and usually have relative (rather than absolute) insulin deficiency, at least initially, and often throughout their lifetime, these individuals do not need insulin treatment to survive. There are probably many different causes of this form of diabetes.

Although the specific etiologies are not known, autoimmune destruction of β-cells does not occur, and patients do not have any of the other causes of diabetes listed above or below. Most patients with this form of diabetes are obese, and obesity itself causes some degree of insulin resistance. Patients who are not obese by traditional weight criteria may have an increased percentage of body fat distributed predominantly in the abdominal region. Ketoacidosis seldom occurs spontaneously in this type of diabetes; when seen, it usually arises in association with the stress of another illness such as infection. This form of diabetes frequently goes undiagnosed for many years because the hyperglycemia develops gradually and at earlier stages is often not severe enough for the patient to notice any of the classic symptoms of diabetes. Nevertheless, such patients are at increased risk of developing macrovascular and microvascular complications. Whereas patients with this form of diabetes may have insulin levels that appear normal or elevated, the higher blood glucose levels in these diabetic patients would be expected to result in even higher insulin values had their β-cell function been normal. Thus, insulin secretion is defective in these patients and insufficient to compensate for insulin resistance. Insulin resistance may improve with weight reduction and/or pharmacological treatment of hyperglycemia, but is seldom restored to normal. The risk of developing this form of diabetes increases with age, obesity (see below), and lack of physical activity. It occurs more frequently in women with prior GDM and in individuals with hypertension or dyslipidemia, and its frequency varies in different racial/ethnic subgroups. It is often associated with a strong genetic predisposition, more so than is the autoimmune form of type 1 diabetes. However, the genetics of this form of diabetes are complex and not clearly defined.

Several forms of diabetes are associated with monogenetic defects in β-cell function (genetic forms of the β-cell). These forms of diabetes are frequently characterized by onset of hyperglycemia at an early age (generally before age 25 years). They are referred to as maturity-onset diabetes of the young (MODY) and are characterized by impaired insulin secretion with minimal or no defects in insulin action. They are inherited in an autosomal dominant pattern. Abnormalities at six genetic loci on different chromosomes have been identified to date. The most common form is associated with mutations on chromosome 12 in a hepatic transcription factor referred to as hepatocyte nuclear factor (HNF)-1α. A second form is associated with mutations in the glucokinase gene on chromosome 7p and results in a defective glucokinase molecule. Glucokinase converts glucose to glucose-6-phosphate, the metabolism of which, in turn, stimulates insulin secretion by the β-cell. Thus, glucokinase serves as the "glucose sensor" for the β-cell. Because of defects in the glucokinase gene, increased plasma levels of glucose are necessary to elicit normal levels of insulin secretion. The less common forms result from mutations in other transcription factors, including HNF-4α, HNF-1β, insulin promoter factor (IPF)-1, and NeuroD1.

Point mutations in mitochondrial DNA have been found to be associated with diabetes mellitus and deafness. The most common mutation occurs at position 3243 in the tRNA leucine gene, leading to an A-to-G transition. An identical lesion occurs in the MELAS syndrome (mitochondria myopathy, encephalopathy, lactic acidosis, and stroke-like syndrome); however, diabetes is not part of this syndrome, suggesting different phenotypic expressions of this genetic lesion.

Genetic abnormalities that result in the inability to convert proinsulin to insulin have been identified in a few families, and such traits are inherited in an autosomal dominant pattern. The resultant glucose intolerance is mild. Similarly, the production of mutant insulin molecules with resultant impaired receptor binding has also been identified in a few families and is associated with an autosomal inheritance and only mildly impaired or even normal glucose metabolism.

There are unusual causes of diabetes that result from genetically determined abnormalities of insulin action (genetic defects in insulin action). The metabolic abnormalities associated with mutations of the insulin receptor may range from hyperinsulinemia and modest hyperglycemia to severe diabetes. Some individuals with these mutations may have acanthosis nigricans. Women may be virilized and have enlarged, cystic ovaries. In the past, this syndrome was termed type A insulin resistance. Leprechaunism and the Rabson-Mendenhall syndrome are two pediatric syndromes that have mutations in the insulin receptor gene with subsequent alterations in insulin receptor function and extreme insulin resistance. The former has characteristic facial features and is usually fatal in infancy, while the latter is associated with abnormalities of teeth and nails and pineal gland hyperplasia.

Alterations in the structure and function of the insulin receptor cannot be demonstrated in patients with insulin-resistant lipoatrophic diabetes. Therefore, it is assumed that the lesion(s) must reside in the postreceptor signal transduction pathways.

Any process that diffusely injures the pancreas can cause diabetes (diseases of the exocrine pancreas). Acquired processes include pancreatitis, trauma, infection, pancreatectomy, and pancreatic carcinoma. With the exception of that caused by cancer, damage to the pancreas must be extensive for diabetes to occur; adrenocarcinomas that involve only a small portion of the pancreas have been associated with diabetes. This implies a mechanism other than simple reduction in β-cell mass. If extensive enough, cystic fibrosis and hemochromatosis will also damage β-cells and impair insulin secretion. Fibrocalculous pancreatopathy may be accompanied by abdominal pain radiating to the back and pancreatic calcifications identified on X-ray examination. Pancreatic fibrosis and calcium stones in the exocrine ducts have been found at autopsy.

Several hormones (e.g., growth hormone, cortisol, glucagon, epinephrine) antagonize insulin action (endocrinopathies). Excess amounts of these hormones (e.g., acromegaly, Cushing's syndrome, glucagonoma, pheochromocytoma, respectively) can cause diabetes. This generally occurs in individuals with preexisting defects in insulin secretion, and hyperglycemia typically resolves when the hormone excess is resolved.

Somatostatinoma- and aldosteronoma-induced hypokalemia can cause diabetes, at least in part, by inhibiting insulin secretion. Hyperglycemia generally resolves after successful removal of the tumor.

Many drugs can impair insulin secretion (drug- or chemical-induced diabetes) These drugs may not cause diabetes by themselves, but they may precipitate diabetes in individuals with insulin resistance. In such cases, the classification is unclear because the sequence or relative importance of β-cell dysfunction and insulin resistance is unknown. Certain toxins such as Vacor (a rat poison) and intravenous pentamidine can permanently destroy pancreatic β-cells. Such drug reactions fortunately are rare. There are also many drugs and hormones that can impair insulin action. Examples include nicotinic acid and glucocorticoids. Patients receiving α-interferon have been reported to develop diabetes as with islet cell antibodies and, in certain instances, severe insulin deficiency.

Certain viruses have been associated with β-cell destruction. Diabetes occurs in patients with congenital rubella, although most of these patients have HLA and immune markers characteristic of type 1 diabetes. In addition, coxsackievirus B, cytomegalovirus, adenovirus, and mumps have been implicated in inducing certain cases of the disease.

In the category of uncommon forms of immune-mediated diabetes, there are two known conditions, and others are likely to occur. The stiff-man syndrome is an autoimmune disorder of the central nervous system characterized by stiffness of the axial muscles with painful spasms. Patients usually have high titers of the GAD autoantibodies, and approximately one-third will develop diabetes.

Anti-insulin receptor antibodies can cause diabetes by binding to the insulin receptor, thereby blocking the binding of insulin to its receptor in target tissues. However, in some cases, these antibodies can act as an insulin agonist after binding to the receptor and can thereby cause hypoglycemia. Anti-insulin receptor antibodies are occasionally found in patients with systemic lupus erythematosus and other autoimmune diseases. As in other states of extreme insulin resistance, patients with anti-insulin receptor antibodies often have acanthosis nigricans. In the past, this syndrome was termed type B insulin resistance.

Many other genetic syndromes are accompanied by an increased incidence of diabetes mellitus. These include the chromosomal abnormalities of Down's syndrome, Klinefelter's syndrome, and Turner's syndrome. Wolfram's syndrome is an autosomal recessive disorder characterized by insulin-deficient diabetes and the absence of β-cells at autopsy. Additional manifestations include diabetes insipidus, hypogonadism, optic atrophy, and neural deafness.

Gestational diabetes mellitus (GDM) is defined as any degree of glucose intolerance with onset or first recognition during pregnancy. The definition applies regardless of whether insulin or only diet modification is used for treatment or whether the condition persists after pregnancy. It does not exclude the possibility that unrecognized glucose intolerance may have antedated or begun concomitantly with the pregnancy. GDM complicates about 4% of all pregnancies in the U.S., resulting in about 135,000 cases annually. The prevalence may range from 1 to 14% of pregnancies, depending on the population studied. GDM represents nearly 90% of all pregnancies complicated by diabetes.

Deterioration of glucose tolerance occurs normally during pregnancy, particularly in the 3rd trimester.

Treatment of diabetes includes insulin, sulfonylureas, meglitinides, biguanides, thiazolidinediones, alpha-glucosidase inhibitors, DPP-4 inhibitors. Some common medications include Actos, Avandamet, avandaryl, avandia, byetta, cozaar, diabeta, diabinase, glucophage, glucotrol, glucovance, glynase, insulin, januvia, lantus, metaglip, micronase, orinase, prandin, precise, riomet, starlix, tolinase, xenical.

Obesity

Obesity is the state of being well above one's normal weight. A person has been considered to be obese if they are more than 20 percent over their ideal weight. That ideal weight must take into account the person's height, age, sex, and build. Obesity has been more precisely defined by the National Institutes of Health (the NIH) as a BMI of 30 and above (a BMI of 30 is about 30 pounds overweight). The BMI (body mass index), a key index for relating body weight to height, is a person's weight in kilograms (kg) divided by their height in meters (m) squared. Since the BMI describes the body weight relative to height, it correlates strongly (in adults) with the total body fat content. Some very muscular people may have a high BMI without undue health risks.

Obesity is often a multifactorial condition, based on both genetic and behavioral factors. Accordingly, treatment of obesity usually requires more than just dietary changes. Exercise, counseling and support, and sometimes medication can supplement diet to help patients conquer weight problems. Extreme diets, on the other hand, can actually contribute to increased obesity.

Overweight is a significant contributor to health problems. It increases the risk of developing a number of diseases including: type 2 (adult-onset) diabetes, hypertension, stroke (cerebrovascular accident or CVA), myocardial infarction, congestive heart failure, cancer (certain forms such as prostate cancer and cancer of the colon and rectum), gallstones and gall bladder disease (cholecystitis), gout and gouty arthritis, osteoarthritis of the knees, hips, and the lower back, sleep apnea, Pickwickian syndrome (obesity, red face, underventilation, and drowsiness).

Metabolic Syndrome, also called insulin resistance syndrome or metabolic syndrome X, is a group of conditions that puts an individual at risk for heart disease and diabetes. Metabolic syndrome X is commonly found in individuals that are obese and seek medical assistance due to underlying dysfunction that leads to symptoms that affect their daily lives. These dysfunctions include hypertension, hyperglycemia, hypertriglyceridemia, lower blood levels of HDL, and abnormal body fat distribution around the torso mid-section (waist). The cause of metabolic syndrome might be insulin resistance. Abnormally high amounts of blood sugar may set the stage for this multi-factorial disease.

Immunological Disease

The present invention provides methods related to an immune disease or disorder. Immune diseases or disorders are for example, rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xenotransplants, etc. The invention further may be related to treatment of immune disease including treatment or preventing of graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves' disease, psoriasis, atopic dermatitis, Crohn's disease, ulcerative colitis, vasculitis, auto-antibody mediated diseases, aplastic anemia, Evan's syndrome, autoimmune hemolytic anemia, and the like. The invention further relates to treatment or prevention of infectious diseases causing aberrant immune response and/or activation, such as traumatic or pathogen induced immune dysregulation, including for example, that which are caused by hepatitis B and C infections, HIV, *Staphylococcus aureus* infection, viral encephalitis, sepsis, parasitic diseases wherein damage is induced by an inflammatory response (e.g., leprosy).

In some embodiments, the invention relates to treatment or prevention of graft vs host disease (especially with allogenic cells), rheumatoid arthritis, systemic lupus erythematosus, psoriasis, atopic dermatitis, Crohn's disease, ulcerative colitis, other forms of inflammatory bowel disease (collagenous colitis, lymphocytic colitis, ischemic colitis, diversion colitis, Behcet's syndrome, infective colitis, indeterminate colitis) and/or multiple sclerosis.

Alternatively or additionally, in some embodiments, the invention relates to treatment or prevention of an immune response associated with a gene therapy treatment, such as the introduction of foreign genes into autologous cells and expression of the encoded product.

Exemplary of diseases caused or worsened by the host's own immune response are autoimmune diseases such as multiple sclerosis, lupus erythematosus, psoriasis, pulmonary fibrosis, and rheumatoid arthritis and diseases in which the immune response contributes to pathogenesis such as atherosclerosis, inflammatory diseases, osteomyelitis, ulcerative colitis, Crohn's disease, and graft versus host disease (GVHD) often resulting in organ transplant rejection. Additional exemplary inflammatory disease states include fibromyalgia, osteoarthritis, sarcoidosis, systemic sclerosis, Sjogren's syndrome, inflammations of the skin (e.g., psoriasis), glomerulonephritis, proliferative retinopathy, restenosis, and chronic inflammations.

Mitochondrial Disease

The present invention provides methods of treating mitochondrial disease, wherein the methods comprise administering a compound of the invention or a pharmaceutically acceptable salt thereof to a subject. Mitochondrial diseases may be caused by mutations, acquired or inherited, in mitochondrial DNA or in nuclear genes that code for mitochondrial components. They may also be the result of acquired mitochondrial dysfunction due to adverse effects of drugs, infections, aging or other environmental causes.

Mitochondrial DNA inheritance behaves differently from autosomal and sex-linked inheritance. Mitochondrial DNA, unlike nuclear DNA, is strictly inherited from the mother and each mitochondrial organelle typically contains multiple mtDNA copies. During cell division, the mitochondrial DNA copies segregate randomly between the two new mitochondria, and then those new mitochondria make more copies. As a result, if only a few of the mtDNA copies inherited from the mother are defective, mitochondrial division may cause most of the defective copies to end up in just one of the new mitochondria. Mitochondrial disease may become clinically apparent once the number of affected mitochondria reaches a certain level; this phenomenon is called 'threshold expression'. Mitochondrial DNA mutations occur frequently, due to the lack of the error checking capability that nuclear DNA has. This means that mitochondrial DNA disorders may occur spontaneously and relatively often. In addition, defects in enzymes that control mitochondrial DNA replication may cause mitochondrial DNA mutations.

Mitochondrial diseases include any clinically heterogeneous multisystem disease characterized by mutations of the brain-mitochondrial encephalopathies and/or muscule-mitochondrial myopathies due to alterations in the protein complexes of the electron transport chain of oxidative phosphorylation. In some embodiment, the invention relates to the treatment or prevention of mitochondrial diseases. For example, the invention provides methods for the treatment or prevention of Leber's hereditary optic atrophy, MERRF (Myoclonus Epilepsy with Ragged Red Fibers), MELAS (Mitochondrial Encephalopathy, Lactic Acidosis and Stroke-like episodes); Alper syndrome, Lowe syndrome, Lull syndrome, Menke's kinky hair syndrome, Zellweger syndrome, mitochondrial myopathy, and rhizomelic chondrodysplasia punctata.

While not intending to be bound to any particular theory, compounds of the invention protect against neuronal dysfunction and death that causes the neurologic symptoms (e.g., cognitive losses, muscle weakness, cardiac dysfunction) diseases that are characterized by mitochondrial dysfunction. In these diseases, dysfunctional mitochondria accumulate. The normal mechanism of mitochondria recycling is unable to keep up with the increased demand. In one aspect of the invention, compounds of the invention stimulate the so-called mitophagy pathway, leading to regeneration of fully functional mitochondria.

MELAS, MERFF, LHON (leber hereditary optic neuropathy), CPEO (chronic progressive external opthalmoplegia), KSS (Kearns-Sayre syndrome), MNGIE (mitochondrial neurogastrointestinal encephalopathy), NARP (neuropathy, ataxia, retinitis pigmentosa and ptosis), Leigh syndrome, Alpers-Huttenlocher disease, Kearns-Sayre syndrome, Pearson syndrome, and Luft disease are examples of mitochondrial diseases treatable by this mechanism.

Mitochondrial function is critical for the generation of ATP, which is critical for all cellular processes. Mitochondrial function decreases with age, due, in part, to environmental toxins and mutations in mitochondrial DNA that occur over time. In addition, some mutations encoded in the mitochondrial genome (and passed exclusively through the mother) are known to predispose to age-related neurodegenerative disease.

Since mitochondrial dysfunction contributes to many, if not all, age-associated degenerative diseases (e.g., Parkinson's, Alzheimer's, Huntington's disease, dilated cardiomyopathy, type 2 diabetes), therapeutic agents that prevented the decline in mitochondrial function could have wide therapeutic utility. There are two classes of agents that could accomplish this: (1) agents that act on single mitochondria and (2) agents that do not affect individual mitochondria, but act on the mitochondrial pool.

In one aspect, compounds of the invention boost net mitochondrial function in INS-1 cells and in pancreatic islet cells.

Without wishing to be bound by theory, in one aspect, the effect of compounds of the invention on net mitochondrial function is mediated by its optimization of the normal cellular surveillance system, whereby dysfunctional mitochondria are identified and degraded. This process is called mitophagy and is a branch of the broader autophagy pathway, which is involved in removing debris from the cytoplasm. New mitochondria can only be produced in conjunction with degradation of dysfunctional mitochondria. Therefore, stimulation of the mitochondrial clearance process (mitophagy) results in production of new fully functional mitochondria and an increase in net mitochondrial function.

An increase in net mitochondrial function would be beneficial to any disease in which decreased mitochondrial function is thought to be responsible. In one aspect, a stimulation of mitophagy would be beneficial to any disease in which decreased mitochondrial function is thought to be responsible, wholly or in part, for symptoms. These diseases include for example: MELAS, Leber syndrome, type 2 diabetes, Alzheimer's disease, Parkinson's disease, Crohn's disease, myopathies (e.g. inclusion body myositis), progressive supranuclear palsy (PSP), Lewy Body Disease (LBD), ALS (amyotophic lateral sclerosis/Lou Gehrig's disease), and Huntington's disease.

Additional mitochondrial disorders include for example, Alpers Disease (Progressive Infantile Poliodystrophy) Barth Syndrome/LIC (Lethal Infantile Cardiomyopathy) Caritine-Acyl-Carnitine Deficiency, Carnitine Deficiency, Co-Enzyme Q10 Deficiency, Mitochondrial Respiratory Chain Disorders, Complex I Deficiency, Complex II Deficiency, Complex III Deficiency, Complex IV/COX Deficiency, Complex V Deficiency, CPEO (Chronic Progressive External Opthalmoplegia Syndrome) CPT I Deficiency, CPT II Deficiency, KSS (Kearns-Sayre Syndrome), Lactic Acidosis, LCAD (Long-Chain Aycl-CoA Dehydrogenase Deficiency) LCHAD, Leigh Disease or Syndrome (Subacute Necrotizing Encephalmyelopathy) LHON (Leber Hereditary Optic Neuropathy), Luft Disease, MAD/Glutaric Aciduria Type H (Multiple Acyl-CoA Dehydrogenase Deficiency), MACD (Medium Chain Acyl-CoA Dehydrogenase Deficiency), MERRF (Myoclonic Epilepsy and Ragged Red Fibre Disease) Mitochondrial Cytopathy, Mitochondrial DNA Depletion, Mitochondrial Encephalopathy, Mitochondrial Myopathy, MINGIE (Myoneurogastointestinal Disorder and Encephalopathy) NARP (Neuropathy, Ataxia and Retinitis Pigmentosa), Pearson Syndrome, Pyruvate Carboxylase Deficiency, Pyruvate Dehydrogenase Deficiency, SCAD (Short-Chain Acyl-CoA Dehydrogenase Deficiency) SCHAD, and VLCAD (Very Long-Chain Acyl-CoA Dehydrogenase Deficiency. The present invention includes a method of treating a proteinopathic subject, wherein the method comprises administering a compound of the invention or a pharmaceutically acceptable salt thereof, to the subject in an amount that is sufficient to improve mitochondrial health in said subject.

The term "mitochondrial health" refers to the ability of mitochondria to function normally in cells. To "improve mitochondrial health" means to assist in a return to normal mitochondrial function in cells. In one aspect, the phrase "to assist in a return to normal mitochondrial" means to assist in an increase in mitochondrial function. An increase in mitochondrial function includes for example, an increase in insulin secretion by cells under glucose stimulated conditions (not basal conditions), an increase in oxygen consumption of cells, prevention or a decrease in fragmentation and abnormal mitochondrial morphology, prevention- or a decrease in cell apoptosis, prevention or a decrease in mitochondrial mutation, an increase in production of new mitochondria, an increase in mitochondrial fusion and fission processes.

In one aspect, to assist in a return to normal mitochondrial function in cells means at least one or more of the following: (1) to increase the efficiency of ATP conversion and distribution (i.e., actual energy release); (2) to speed up the rate of recycling of ADP back to ATP again (i.e., energy recovery times and energy reserve; (3) to provide the body with enough raw materials to produce new ATP (replenishing depleted energy reserves—having converted some of the ADP to non-recoverable AMP in lieu of any ATP being available. In another aspect, to assist in a return to normal mitochondrial function in cells means to decrease the amount of mitochondrial dysfunction in cells.

Mitochondria are known as the "powerhouse" of cells. The primary function of mitochondria is to generate the cell's supply of adenosine triphosphate (ATP). During cellular respiration, the mitochondria inside each cell take in oxygen, sugar and ADP (effectively spent energy) and produce ATP, which acts to distribute chemical energy inside of the cell for metabolism. The ATP moves outside of the mitochondrial membrane and floats around inside of the cell in the cytoplasm until it is used up in a variety of processes. Energy is released when ATP is converted to ADP. Virtually, every biochemical reaction in the body is driven by the conversion of ATP to ADP. The average person turns over approximately his or her own body weight in ATP each day. Mitochondria also function in other cellular processes, such as signaling, cellular differentiation, cell death, as well as the control of the cell cycle and cell growth. For example, mitochondria are responsible for the β-oxidation of short-, medium-, and long-chain fatty acids as well as central to intermediary metabolism, ROS generation, and apoptosis.

The term "mitochondrial dysfunction" refers to when the ability of the mitochondria to function normally is reduced or decreased in cells. For example, one aspect of mitochondrial dysfunction includes when the mitochondria fail to produce adequate levels of ATP.

In one aspect, mitochondria dysfunction occurs as a result of aging. Studies show that as people age, the efficiency of the mitochondria to convert ADP to ATP diminishes and so does the quantity of mitochondria per cell. As a result, the amount of ATP turned over decreases. For example, a 68-year old person produces approximately half the amount of ATP compared to a 39-year old person. Cells die because mitochondria fail to produce adequate energy molecules.

Aging mitochondria are not only less efficient at converting ADP to ATP, but they can also produce harmful oxidants. For example, mitochondria can be poisoned by numerous substances, including environmental toxins, heavy metals, excess iron (haemocromatosis), pesticides, chronic bacteria, viral and fungal infections and neurotoxins. These agents can induce excess production of reactive oxygen species such as superoxide, hydroxyl radicals, peroxynitrite, etc. which cause oxidation and thus damage of the mitochondria which in effect reduces their ability to produce energy.

Another aspect of mitochondrial dysfunction is inefficient recycling of ADP back to ATP and the undesired production of AMP. If a cell is not efficient at recycling ADP to ATP, then the cell runs out of energy very quickly. The cell must then go into a 'rest' period when no more ATP is available, and then the cell will use ADP instead and convert this into AMP. However, AMP cannot be recycled, which is why the body does not use normally use ADP to produce energy. ATP can only be recycled from ADP and the rest must be created from scratch, which requires the body to break down various proteins, triglycerides, fatty acids, and sugars into their constituent parts, and then the mitochondria must build up the ATP from these components. The ratio between ATP and AMP is a way to measure how much energy is available.

Another aspect of mitochondrial dysfunction involves anaerobic respiration, a mechanism used when insufficient ATP is available. If the body is very short of ATP, it can make a very small amount of ATP directly from glucose by converting it into lactic acid to produce two molecules of ATP for the body to use. However, this type of anaerobic metabolism results in problems—lactic acid quickly builds up and causes pain and the body's glucose is used up and unavailable to make D-ribose, which is needed to generate new ATP. When mitochondria function well, as a person rests following exertion, lactic acid is quickly converted back to glucose and the lactic burn disappears. This process requires six molecules of ATP. If there is no ATP available, e.g., when mitochondria fail, then the lactic acid may persist for several minutes or hours and cause a great deal of pain.

Another potential factor explaining poor ATP availability is a lowered level of mitochondria in patients with mitochondrial dysfunction. Mitochondria themselves have a very short half life. It is estimated that they have a half life of 5-12 days (meaning that half of the mitochondria in the body will have 'died' after 5-12 days if no more were produced). Mitochondria are recycled by the autophagy process. This recycling of mitochondrial to produce new mitochondria requires energy or ATP, which clearly if deficient to start with, may be delayed or postponed, meaning that the resulting remaining functioning mitochondria may be somewhat less than it should be in a healthy organism. Fewer mitochondria means those that remain are put under more pressure to produce ATP and are thus depleted quicker than they would normally be.

Low levels of mitochondrial regeneration may be explained by low basal nitric oxide (NO) levels. NO is a major regulator of ATP levels. Low NO levels cause low ATP levels, which thus disables autophagy, preventing recycling of mitochondria. There is more peroxynitrite damage observed because there is less recycling of mitochondria occurring (less autophagy) and hence less repair of peroxynitrite-damaged proteins. In other words, there is a resulting accumulation of peroxynitrite-damaged proteins and lipids. Because of low NO levels, there is less synchronization between cells in terms of their energy output, meaning some are overloaded and some are underloaded.

In another aspect, the mitochondrial dysfunction is due to the actual integrity of the mitochondrial membranes rather than the actual number of mitochondria, which may or may not be normal. Several factors can affect mitochondrial membrane integrity and severely impact the body's ability to aerobically respire and force it to use anaerobic respiration more. Factors that affect the mitochondrial membrane can severely impact the body's ability to aerobically respire and force it to use anaerobic respiration more to produce energy. Factors affecting mitochondrial membrane integrity include fatty acid imbalances, excessive free radical (oxidative) damage to the mitochondrial membrane, compounds that clogg up the mitochondrial membranes thus reducing mitochondrial membrane permability and ATP production (e.g., toxins, partial detoxification products, foreign/unwanted compounds), elevated hydrogen sulphide levels, too low a pH at the membrane (too acidic), elevated intracellular calcium and reduced intracellular magnesium.

Symptoms of mitochondrial dysfunction may include a lack of physical energy, lack of mental energy and ability to concentrate ('brain fog'), tendency to crash and burn, muscle and joint weakness, cardiac weakness/insufficiency, digestive insufficiency, and perhaps even muscle control. The exact effects vary according to the individual.

Getting sufficient oxygen to the mitochondria is key to enabling proper mitochondrial function. Low blood and body oxygen levels are frequently associated with excessive fat, insufficient cardiovascular exercise, slightly lowered blood/bodily pH (excessive acid producing food consumption), fatty acid imbalances and/or poor membrane permability.

Mitochondrial function can be assessed using a variety of methods for example, a Clark-type electrode probe is used for measuring oxygen consumption, luminescent ATP assays quantitatively measure total energy metabolism, and MTT or Alamar Blue to determine metabolic activity. Alternatively, label-free, assay systems e.g., extracellular flux (XF) assays are used measure the two major energy-producing pathways of the cell simultaneously—mitochondrial respiration (oxygen consumption) and glycolysis (extracellular acidification)—in a sensitive microplate format. XF assays work with adherent cells offering a physiologically relevant, real-time cellular bioenergetic assay.

As used herein, an "improvement in mitochondrial health" is demonstrated, for example, by an increase in insulin secretion by cells under glucose stimulated conditions (not basal conditions), an increase in oxygen consumption of cells, prevention or a decrease in fragmentation and abnormal mitochondrial morphology, prevention or a decrease in cell apoptosis, prevention or a decrease in mitochondrial mutation, an increase in the production of new mitochondria, a promotion in mitochondrial fusion and fission processes. The invention includes a method, wherein administration of said compound promotes mitochondrial fusion and fission processes. In one aspect, the promotion of mitochondrial fusion and fission processes results in an improvement in mitochondrial health.

In healthy cells, mitochondrial morphology is maintained through a dynamic balance between fusion and fission processes, and this regulated balance seems to be required for maintaining normal mitochondrial and cellular function. Dysregulated mitochondrial fusion and fission processes are now be regarded as playing important pathogenic roles in neurodegeneration (Frank, S. Acta Neuropathol (2006) 111: 93-100). Age-dependent decreases in mitochondrial fusion and fission activity have been demonstrated (Jendrach et al. (2005) Mech Ageing Dev 126: 813-821), perhaps indicating that a decline in these important physiological functions could not only contribute to the accumulation of damaged mitochondria, but also to the pathogenesis of age-related neurodegenerative diseases. As such, there is a need for compounds that promote mitochondrial fusion and fission processes thereby improving mitochondrial health.

The invention includes a method, wherein administration of said compound stimulates mitophagy. In one aspect, a stimulation of mitophagy results in an improvement in mitochondrial health. As used herein, the term "stimulates mitophagy" means that the mitochondrial clearance process is stimulated resulting in the production of new fully functional mitochondria and/or an increase in net mitochondrial function.

The invention includes a method, wherein administration of said compound increases autophagic flux in said subject. In one aspect, the increase in autophagic flux results in an improvement in mitochondrial health.

An "increase in mitochondrial function" includes for example, an increase in insulin secretion by cells under glucose stimulated conditions (not basal conditions), an increase in oxygen consumption of cells, prevention or a decrease in fragmentation and abnormal mitochondrial morphology, prevention- or a decrease in cell apoptosis, prevention or a decrease in mitochondrial mutation, an increase in production of new mitochondria, an increase in mitochondrial fusion and fission processes. The invention includes a method, wherein administration of said compound promotes the identification and degradation of dysfunctional mitochondria.

The term "autophagy" refers a catabolic process involving the degradation of a cell's own components through the lysosomal machinery. It is a tightly-regulated process that plays a normal part in cell growth, development, and homeostasis, helping to maintain a balance between the synthesis, degradation, and subsequent recycling of cellular products. It is a major mechanism by which a starving cell reallocates nutrients from unnecessary processes to more-essential processes.

A variety of autophagic processes exist, all having in common the degradation of intracellular components via the lysosome. The most well-known mechanism of autophagy involves the formation of a membrane around a targeted region of the cell, separating the contents from the rest of the cytoplasm. The resultant vesicle then fuses with a lysosome and subsequently degrades the contents.

The invention includes a method, wherein administration of a compound of the invention increases autophagy in said subject. In another aspect, the invention includes a method, wherein administration of a compound of the invention does not increase autophagy in said subject. In one aspect of the invention, administration of a compound of the invention enhances autophagy at certain doses. In one aspect of the invention, administration of a compound of the invention enhances autophagy at certain low doses e.g., <1 nM. In another aspect of the invention, administration of a compound of the invention blocks autophagy at certain doses. In one aspect of the invention, administration of a compound of the invention blocks autophagy at certain high doses e.g., 100 nM.

The invention includes a method, wherein administration of a compound of the invention promotes the production of new fully functional mitochondria.

The invention includes a method, wherein administration of a compound of the invention protects cells from cell death. In one aspect, administration of a compound of the invention protects cells from rotenone-mediated cell death. For example, administration of a compound of the invention protects cells from rotenone-mediated cell death as demonstrated by mitochondrial survival. In one aspect, a compound of the invention works by enhancing mitochondrial survival.

The invention includes a method, wherein the subject is suffering from a mitochondrial disorder, wherein decreased mitochondrial function is responsible, wholly or in part, for the symptoms of said disease.

The invention includes a method, wherein the mitochondrial disorder that the subject is suffering from is selected from MELAS, Leber syndrome, type 2 diabetes, Alzheimer's disease, Parkinson's disease, Crohn's disease, and mitochondrial myopathies (e.g., inclusion body myositis), progressive supranuclear palsy (PSP), Lewy Body Disease (LBD), ALS (amyotophic lateral sclerosis/Lou Gehrig's disease), and Huntington's disease.

The invention includes a method, wherein administration of a compound of the invention provides at least one of the following: (i) the compound prevents cell death from glucolipotoxicity; (ii) the compound protects cells from glucolipotoxicity-induced fragmentation; (iii) the compound increases insulin secretion by cells under glucose stimulated conditions; (iv) the compound does not increase insulin secretion by cells under basal glucose conditions; or (v) the compound increases oxygen consumption of cells. In one aspect of the invention, the cells referred to herein are insulin secreting beta cells. In another aspect of the invention, the cells referred to herein are pancreatic islet cells.

The invention includes a method, wherein administration of a compound of the invention provides at least one of the following:

(i) The compound prevents cell death from glucolipotoxicity (e.g., palmitate toxicity) such that when the compound is administered, there are up to 40% less dead cells than if the compound is not administered. The compound prevents cell death from glucolipotoxicity such that there are up to 30% less dead cells. The compound prevents cell death from glucolipotoxicity such that there are up to 20% less dead cells. The compound prevents cell death from glucolipotoxicity such that there are 1-40%, preferably 3-30%, more preferably 5-20% less dead cells. In one aspect of the invention, there are about 1%, 3%, 5%, 10%, 15%, 20%, 30%, 40% less dead cells when the compound is administered than when the compound is not administered.

(ii) The compound protects cells from glucolipotoxicity-induced fragmentation such that when the compound is administered, fragmentation is reduced by up to 80% in comparison to when the compound is not administered. The compound protects cells from glucolipotoxicity-induced fragmentation such that fragmentation is reduced by up to 65%. The compound protects cells from glucolipotoxicity-induced fragmentation such that fragmentation is reduced by up to 55%. The compound protects cells from glucolipotoxicity-induced fragmentation such that fragmentation is reduced by about 20-80%, preferably 40-75%, more preferably 50-65%. In one aspect of the invention, when the compound is administered, fragmentation is reduced by about 30%, 35%, 40%, 45%, 50%, 55%, 60%, 65%, 70%, 75% in comparison to when the compound is not administered.

(iii) The compound protects cells from glucolipotoxicity-induced fragmentation such that when the compound is administered, up to 85% of the abnormal mitochondrial morphology is normalized in comparison to when the compound is not administered. The compound protects cells from glucolipotoxicity-induced fragmentation such that up to 80% of the abnormal mitochondrial morphology is normalized. The compound protects cells from glucolipotoxicity-induced fragmentation such that 70% of the abnormal mitochondrial morphology is normalized. The compound protects cells from glucolipotoxicity-induced fragmentation such that about 0-90%, preferably 55-80%, more preferably 60-75% of the abnormal mitochondrial morphology is normalized. In one aspect of the invention, when the compound is administered, about 35%, 40%, 45%, 50%, 55%, 60%, 65%, 70%, 75%, 80%, 85%, 90% of the abnormal mitochondrial morphology is normalized in comparison to when the compound is not administered.

(iv) The compound increases insulin secretion by cells by up to 200% under glucose stimulated conditions when the compound is administered in comparison to when the compound is not administered. The compound increases insulin secretion by cells by up to 150% under glucose stimulated conditions. The compound increases insulin secretion by cells by up to 100% under glucose stimulated conditions. The compound increases insulin secretion by cells by about 40-150%, preferably 50-120%, more preferably 55-105%. In one aspect of the invention, when the compound is administered insulin secretion by cells is increased by about 40%, 45% 50%, 55%, 60%, 65% 70%, 75%, 80%, 85%, 90%, 95%, 100%, 120%, 130%, 150%, 175%, 200% in comparison to when the compound is not administered. In another aspect, the compound increases insulin secretion by less than 35% in cells under basal conditions (non-glucose stimulated). In another aspect, the compound increases insulin by less than 25% in cells under basal conditions. In another aspect, the compound increases insulin by 1-35%, preferably 5-30%, more preferably 10-25% under basal conditions. In another aspect, the compound increases insulin by less than 30%, 25%, 20%, 15%, 10%, 5% under basal conditions.

(v) The compound increases oxygen consumption of cells by up to 400% when the compound is administered in comparison to when the compound is not administered. The compound increases oxygen consumption of cells by up to 200% when the compound is administered. The compound increases oxygen consumption of cells by up to 160% when the compound is administered. The compound increases oxygen consumption of cells when the compound is administered by 50-400%, preferably 80-175%, more preferably 100-165%. In one aspect of the invention, when the compound is administered oxygen consumption is increased by about 50%, 60%, 70%, 80%, 90%, 100%, 120%, 130%, 140%, 150%, 155%, 160%, 170%, 175%, 180%, 185%, 190%, 200%, 250%, 300%, 350%, 400% in comparison to when the compound is not administered.

The invention includes a method, wherein administration of a compound of the invention provides at least one of the following: (i) The compound prevents cell death from glucolipotoxicity such that there are 3-30% less dead cells; (ii) The compound protects cells from glucolipotoxicity-induced fragmentation such that fragmentation is reduced by 40-75%; (iii) The compound protects cells from glucolipotoxicity-induced fragmentation such that 55-80% of the abnormal mitochondrial morphology is normalized; (iv) The compound increases insulin secretion by cells under glucose stimulated conditions by 50-120%; and (v) The compound increases oxygen consumption of cells by 80-175%.

The invention includes a method, wherein administration of a compound of the invention provides at least one of the following: (i) The compound prevents cell death from glucolipotoxicity such that there are 5-20% less dead cells; (ii) The compound protects cells from glucolipotoxicity-induced fragmentation such that fragmentation is reduced by 50-65%; (iii) The compound protects cells from glucolipotoxicity-induced fragmentation such that 60-75% of the abnormal mitochondrial morphology is normalized; (iv) The compound increases insulin secretion by cells under glucose stimulated conditions by 55-105%; or (v) The compound increases oxygen consumption of cells by 100-165%.

The invention includes a method, wherein a compound of the invention acts on a single mitochondria. In another aspect of the invention, a compound of the invention does not act on the mitochondrial pool.

The invention includes a method, wherein the amount a compound of the invention or a pharmaceutically acceptable salt thereof, administered ranges from approximately 0.1 mg per day to approximately 50 mg per day. The invention includes a method, wherein the amount a compound of the invention or a pharmaceutically acceptable salt thereof, administered ranges from approximately 0.5 mg per day to approximately 30 mg per day. The invention includes a method, wherein the amount of a compound of the invention or a pharmaceutically acceptable salt thereof, ranges from approximately 4 mg per day to approximately 20 mg per day.

The invention includes a method, wherein the amount of a compound of the invention or a pharmaceutically acceptable salt thereof, is not sufficient to inhibit the farnesylation of Ras in the brain by more than about 50%. The invention includes a method, wherein the amount of a compound of the invention or a pharmaceutically acceptable salt thereof, is sufficient to inhibit the farnesylation of UCH-L1.

The invention includes a method, wherein the proteinopathic subject is suffering from a neurodegerative disease, a cognitive impairment, dementia, depression, anxiety, a lysosomal storage disease, an ocular disease, an inflammatory disease, a cardiovascular disease, a proliferative disease, immunologic disease, myopathy, diabetes, obesity, traumatic brain injury or a mitochondrial disease. The invention includes a method, wherein the neurodegenerative disease is selected from Parkinson's disease, diffuse Lewy body disease, multiple system atrophy, pantothenate kinase-associate neurodegeneration, amyotrophic lateral sclerosis, Huntington's disease, and Alzheimer's disease.

The invention includes a method, further comprising administering to the subject a therapeutically effective amount of a non-farnesyl transferase inhibitor. The invention includes a method, wherein the non-farnesyl transferase inhibitor is selected from the group consisting of dopamine agonists, DOPA decarboxylase inhibitors, dopamine precursors, monoamine oxidase blockers, cathechol O-methyl transferase inhibitors, anticholinergics, acetylcholinesterase inhibitors, activators of neurotrophic receptors, gamma-secretase inhibitors, PDE10 inhibitors, and NMDA antagonists.

The invention includes a method, wherein the subject is a human.

Ocular Disease

The present invention provides methods of treating ocular disease, wherein the methods comprise administering a compound of the invention or a pharmaceutically acceptable salt thereof to a subject.

In some embodiments, compounds of the invention are useful for the treatment of ocular indications that benefit from a compound that simulates cellular autophagy. Ocular indications include but are not limited to retinitis pigmentosa, wet and dry forms of age related macular degeneration, ocular hypertension, glaucoma, corneal dystrophies, retinoschises, Stargardt's disease, autosomal dominant druzen, Best's macular dystrophy, myocilin glaucoma, or Malattia Leventineses. Another ocular indication includes Leber's hereditary optic neuropathy (LHON) or Leber optic atrophy, a mitochondrially inherited (mother to all offspring) degeneration of retinal ganglion cells (RGCs) and their axons that leads to an acute or subacute loss of central vision; this affects predominantly young adult males. However, LHON is only transmitted through the mother as it is primarily due to mutations in the mitochondrial (not nuclear) genome and only the egg contributes mitochondria to the embryo. LHON is usually due to one of three pathogenic mitochondrial DNA (mtDNA) point mutations. These mutations are at nucleotide positions 11778 G to A, 3460 G to A and 14484 T to C, respectively in the ND4, ND1 and ND6 subunit genes of complex I of the oxidative phosphorylation chain in mitochondria. Men cannot pass on the disease to their offspring.

Additional Uses

The present invention provides methods of treating uterine leiomyomata, lymphangioleiomyomatosis, endometriosis, and systemic amyloidoses, wherein the methods comprise administering a compound of the invention or a pharmaceutically acceptable salt thereof to a subject.

Uterine leiomyomas are common, benign, smooth muscle tumors of the uterus. They are found in nearly half of women over age 40 and infrequently cause problems. Synonyms include Fibroids, Myomas, and Leiomyomata.

Lymphangioleiomyomatosis (LAM) is a rare lung disease that results in a proliferation of disorderly smooth muscle growth (leiomyoma) throughout the bronchioles, alveolar septa, perivascular spaces, and lymphatics, resulting in the obstruction of small airways (leading to pulmonary cyst formation and pneumothorax) and lymphatics (leading to chylous pleural effusion). LAM occurs in a sporadic form, which only affects females, who are usually of childbearing age. LAM also occurs in patients who have tuberous sclerosis.

Endometriosis is the growth of cells similar to those that form the inside of the uterus (endometrial cells), but in a location outside of the uterus.

Systemic amyloidosis can be classified as follows: (1) primary systemic amyloidosis (PSA), usually with no evidence of preceding or coexisting disease, paraproteinemia, or plasma-cell dyscrasia; (2) amyloidosis associated with multiple myeloma; or (3) secondary systemic amyloidosis with evidence of coexisting previous chronic inflammatory or infectious conditions.

Primary systemic amyloidosis involves mainly mesenchymal elements, and cutaneous findings are observed in 30-40% of patients. Secondary systemic amyloidosis does not involve the skin, whereas localized amyloidosis does.

Primary systemic amyloidosis involves the deposition of insoluble monoclonal immunoglobulin (Ig) light (L) chains or L-chain fragments in various tissues, including smooth and striated muscles, connective tissues, blood vessel walls, and peripheral nerves. The amyloid of primary systemic amyloidosis is made by plasma cells in the bone marrow. These L-chains are secreted into the serum. Unlike the normal L-chain and the usual form seen in patients with myeloma, these L-chains are unique in that they undergo partial lysosomal proteolysis within macrophages, and they are extracellularly deposited as insoluble amyloid filaments attached to a polysaccharide. Sometimes, instead of an intact L-chain, this amyloid has the amino-terminal fragment of an L-chain.

In some aspects, the invention includes a method of reducing protein aggregation or accumulation toxicity in a cell, the method comprising: administering to a cell a therapeutically effective amount of a compound described herein, or a composition thereof. In some aspects, the invention includes a method of reducing protein aggregation or accumulation toxicity in a neuronal cell. In some aspects, the invention includes a method of reducing protein aggregation or accumulation toxicity in a non-neuronal cell. In some aspects, the invention includes a cell that expresses α-synuclein. In some aspects, the invention includes a method of reducing protein aggregation or accumulation toxicity in a cell that expresses amyloid. In some aspects, the invention includes a method of reducing protein aggregation or accumulation toxicity in a cell that expresses tau.

In some aspects, the invention includes a method of reducing α-synuclein toxicity in a cell, the method comprising administering to a cell a therapeutically effective amount of a compound described herein, or a composition thereof. In some aspects, the invention includes a method of reducing α-synuclein toxicity in a cell, wherein the cell is a neuronal cell. In some aspects, the invention includes a method of reducing α-synuclein toxicity in a cell, wherein the cell is a non-neuronal cell. In some aspects, the invention includes a method of reducing α-synuclein toxicity in a cell, wherein the cell expresses α-synuclein.

In some aspects, the invention includes a method of reducing amyloid beta toxicity in a cell, the method comprising: administering to a cell a therapeutically effective amount of a compound described herein, or a composition thereof. In some aspects, the invention includes a method of reducing amyloid beta toxicity in a cell, wherein the cell is a neuronal cell. In some aspects, the invention includes a method of reducing amyloid beta toxicity in a cell, wherein the cell is a non-neuronal cell. In some aspects, the invention includes a method of reducing amyloid toxicity in a cell, wherein the cell expresses amyloid beta.

A method of reducing tau toxicity in a cell, the method comprising: administering to a cell a therapeutically effective amount of a compound described herein, or a composition thereof. In some aspects, the invention includes a method of reducing tau toxicity in a cell, wherein the cell is a neuronal cell. In some aspects, the invention includes a method of reducing tau toxicity in a cell, wherein the cell is a non-neuronal cell. In some aspects, the invention includes a method of reducing tau toxicity in a cell, wherein the cell expresses tau.

Dosing

Compounds and/or compositions described herein may be administered according to any of a variety of dosing regimens.

In some embodiments, compounds are administered at a dose within the range of 0.0001-100 mg/kg. In some embodiments, doses within the range of 0.001-10 mg/kg are administered. In some embodiments, doses within the range of 0.001-1.0 mg/kg are administered. In some embodiments, doses within the range of 0.001-0.5 mg/kg are administered. In some embodiments, doses within the range of 0.01-1.0, or 0.01-0.5, or 0.001-0.2, or 0.01-0.2 mg/kg are administered. In some embodiments, such doses are utilized as average daily doses.

In certain embodiments, an average daily dose for an adult human may be in the range of approximately 0.1-approximately 150 mg. In certain particular embodiments, for an adult human, the daily dose ranges from approximately 0.1 mg to 100 mg. In certain embodiments, the daily dosage ranges from approximately 0.1 mg to approximately 50 mg. In certain embodiments, the daily dose ranges from approximately 0.5 mg to approximately 30 mg. In certain embodiments, the daily dose ranges from approximately 4 mg to approximately 20 mg. In certain embodiments, the daily dose ranges from approximately 10 mg to approximately 30 mg. In certain embodiments, the daily dose ranges from approximately 10 mg to approximately 25 mg. In certain embodiments, the daily dose ranges from approximately 10 mg to approximately 30 mg. In certain embodiments, the daily dose of the FTI is approximately 1 mg, approximately 5 mg, approximately 10 mg, approximately 15 mg, approximately 20 mg, approximately 25 mg; approximately 30 mg, approximately 35 mg, approximately 40 mg, approximately 45 mg, or approximately 50 mg.

Generally doses of the compound of the invention for a patient, when used for the indicated effects, will range from about 7 to 10,500 mg per kg of body weight per day. Preferably, the daily dosage will range from about 7 to 3500 mg per kg of body weight per day. More preferably the daily dosage will range from 35 to 2100 mg of compound per kg of body weight, and even more preferably from 280 to 1400 mg of compound per kg of body weight. However, lower or higher doses may be used. Such doses may correspond to doses found useful and appropriate in an applicable animal model (e.g., in a transgenic rodent model). In some embodiments, the dose administered to a subject may be modified as the physiology of the subject changes due to age, disease progression, weight, or other factors.

In some embodiments, compounds and/or composition of the present invention are administered according to a regimen that achieves an area under the curve (AUC) that is less than approximately 2500 ng hr/ml. In some embodiments, compounds and/or composition of the present invention are administered according to a regimen that achieves an area under the curve (AUC) that is less than approximately 2000, 1500, 1000, 500, 100, or 50 ng hr/ml.

In some embodiments, compounds and/or compositions are administered using a chronic administration regimen. In some such embodiments, dosing is continued for one or more weeks, months, or years. In some embodiments, compounds and/or compositions are administered for the life of the individual. In some embodiments, chronic administration regimens administer compound and/or composition one or more times per day, week, month, year, etc.

In some embodiments, compounds and/or compositions provided herein are administered via an intermittent dosing regimen. In some embodiments, intermittent dosing involves administration of one or more doses, followed by a cessation of doses for a period of time. In some embodiments, doses are administered again after the period of cessation. To give but a couple of examples of intermittent dosing schedules, in some embodiments, compounds and/or compositions are administered over a period of 3-7 days (e.g., 3, 4, 5, 6, or 7 days), followed by a period of 3-7 days off. In some embodiments, compounds and/or compositions are administered periodically over several months, followed by several months off, etc. In some embodiments, compounds and/or compositions are administered every day for one week, followed by several weeks off and then repeated administration every day for one week, etc.

In some embodiments, compounds and/or compositions provided herein are administered every other day, every third day, every fourth day, once a week, every other week, twice a month, every third week, every fourth week, once a month, every other month, etc.

Various functions and advantages of these and other embodiments of the present invention will be more fully understood from the examples described below. The following examples are intended to illustrate the benefits of the present invention, but do not exemplify the full scope of the invention.

EXEMPLIFICATION

Example 1

Synthetic Procedures

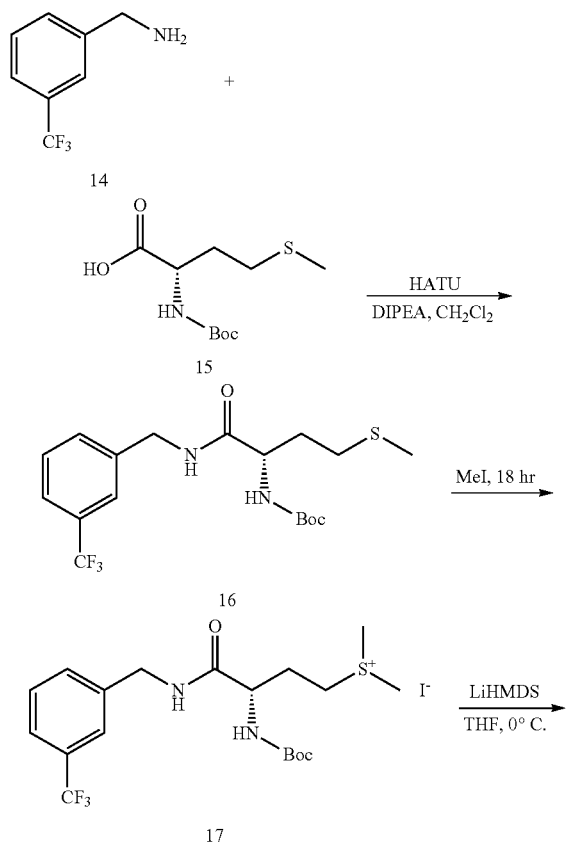

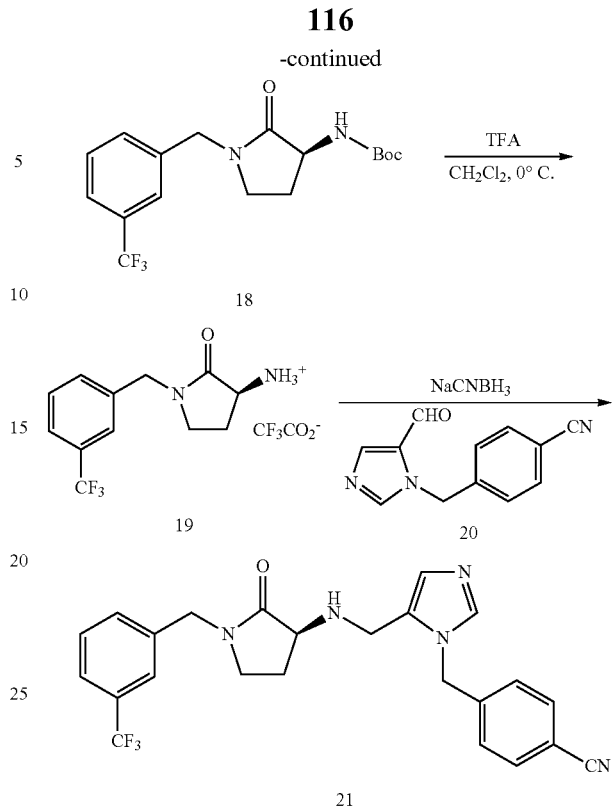

Scheme 4 depicts the synthesis of (S)-4-((5-((2-oxo-1-(3-(trifluoromethyl)benzyl)pyrrolidin-3-ylamino)methyl)-1H-imidazol-1-yl)methyl)benzonitrile 21 from (3-trifluoromethyl)phenyl)methanamine 14 and N-Boc-protected (S)-2-amino-4-(methylthio)butanoic acid 15 as described generally in Schemes 1, 2, and 3 in the general methods section of this application. Specifically, (3-trifluoromethyl)phenyl)methanamine 14 is coupled to N-Boc-protected (S)-2-amino-4-(methylthio)butanoic acid 15 using the peptide coupling reagent HATU in the presence of diisopropylethylamine and methylene chloride to furnish the corresponding amide 16. Methylation of the pendant thiol moiety of (S)-tert-butyl 4-(methylthio)-1-(3-(trifluoromethyl)benzylamino)butan-2-ylcarbamate 16 affords the corresponding sulfonium iodide salt 17, which then undergoes an intramolecular cyclization to afford (S)-tert-butyl 2-oxo(3-(trifluoromethyl)benzyl)pyrrolidin-3-ylcarbamate 18. Deprotection of Boc-protected 18 using trifluoroacetic acid (TFA) affords the corresponding TFA salt 19, which is then added to 4-((5-formyl-1H-imidazol-1-yl)methyl)benzonitrile 20 in the presence of NaCNBH₃ in order to undergo a reductive amination to afford (S)-4-(5-((2-oxo-1-(3-(trifluoromethyl)benzyl)pyrrolidin-3-ylamino)methyl)-1H-imidazol-1-yl)methyl)benzonitrile 21.

Scheme 5

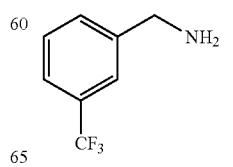

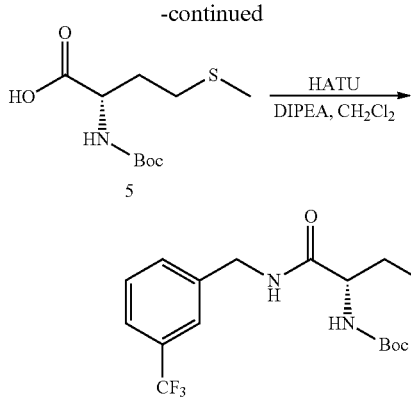

Procedure: To a mixture of Boc-L-methionine (1.47 g, 5.9 mmol) in methylene chloride (10 mL) was added HATU (2.6 g, 6.8 mmol) and DIPEA (1.1 mL) and the solution was cooled to 0-5° C. with an ice bath. Meta-trifluorobenzylamine (1.0 g, 5.7 mmol) in 1 mL methylene chloride was added dropwise over 15 minutes and the reaction was stirred at 0-5° C. for 1 hour and then allowed to stir at room temperature for 16 hours. The reaction was neutralized with 1M citric acid (30 mL) and the layers were separated. The aqueous layer was extracted two times with methylene chloride (25 mL). The organic layers were combined and washed once with brine (50 mL), dried over $Mg_2SO_4$, filtered, and concentrated to an oil. The material was purified by flash chromatography (40% ethyl acetate/hexane) to provide 1.94 g (84%) amide 6 as a white solid.

TLC: $R_f$ 0.30 (40% ethyl acetate/hexane visualized by UV and Iodine); $^1$H NMR ($CDCl_3$): 7.51 (m, 2H), 7.45 (m, 2H), 6.84 (brs, 1H), 5.20 (d, J=7.8 Hz, 1H), 4.49 (brs, 2H), 4.30 (m, 1H), 2.55 (m, 2H), 2.12 (m, 1H), 2.08 (s, 3H), 1.96 (m, 1H), 1.41 (s, 9H); LC/MS: amide 6, $R_t$ 8.4 min, ($M^+$+1) 407.

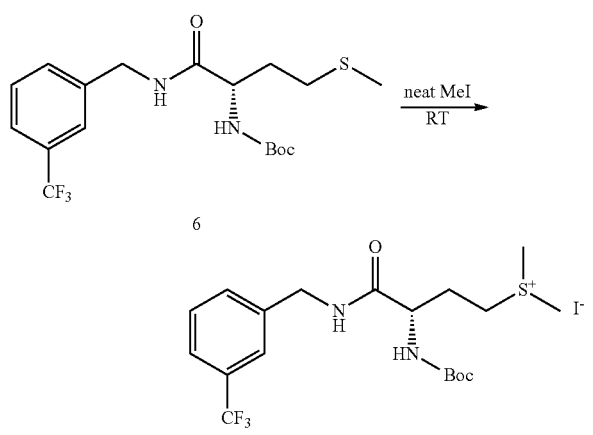

Procedure: Amide 6 (1.9 g, 4.7 mmol) and 20 mL iodomethane was stirred at room temperature for 17 hours. Initially, the mixture was homogeneous but after 17 hours a solid had precipitated. The reaction was diluted with 200 mL hexane and the solid was collected by filtration to provide 1.96 g (76%) of the iodo salt 7 as a light yellow powder. $^1$H NMR ($CD_3OD$): 7.57 (m, 4H), 4.47 (q, J=16.0, 15.2 Hz, 2H), 4.24 (m, 1H), 3.38 (t, J=7.8 Hz, 2H), 2.94 (s, 6H), 2.31 (m, 1H), 2.14 (m, 1H), 1.45 (s, 9H); LC/MS: salt 7, $R_t$ 5.8 min, ($M^+$) 421.3.

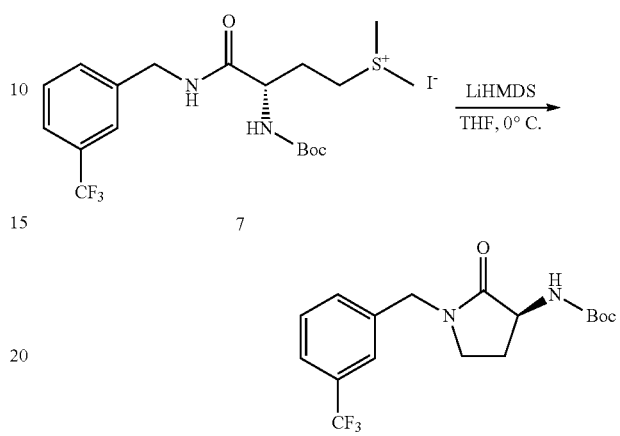

Procedure: Compound 7 (1.96 g, 3.6 mmol) was dissolved in 60 mL anhydrous THF and cooled in an ice bath. A solution of 1M LiHMDS (3.6 mL) was added dropwise and the reaction was stirred at 0° C. for 2 hours. The reaction was warmed to room temperature and stirred for an additional 2 hours. The reaction was quenched with saturated ammonium chloride (60 mL) and extracted twice with ethyl acetate (60 mL). The combined organic layers were washed with brine (100 mL), dried over $Mg_2SO_4$, filtered, and concentrated to an oily solid. The material was purified by chromatography using a gradient (12-100% ethyl acetate/hexane) to provide 0.8 g (62%) pyrrolidone 8 as a white solid. TLC: $R_f$ 0.33 (80% ethyl acetate/hexane visualized by UV); $^1$H NMR ($CDCl_3$): 7.56 (m, 1H), 7.45 (m, 3H), 5.17 (brs, 1H), 4.54 (dd, J=14.8 Hz, 2H), 4.21 (brm, 1H), 3.23 (complex m, 2H), 2.62 (brm, 1H), 1.88 (complex m, 1H), 1.46 (s, 9H); LC/MS: amide 8, $R_t$ 7.7 min, ($M^+$+1) 359.2.

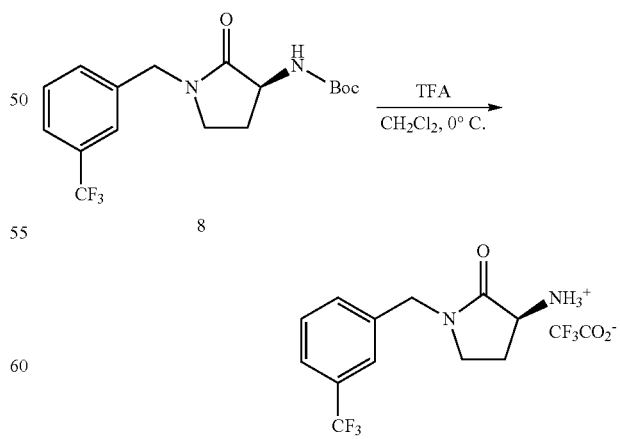

Procedure: Pyrrolidone 8 (0.8 g, 2.2 mmol) was dissolved in methylene chloride (4.8 mL) and cooled in an ice bath.

Trifluoroacetic acid (4.8 mL) was added dropwise and the yellow solution was allowed to warm to room temperature and stirred for 2 hours. The reaction was concentrated under reduced pressure and diluted and concentrated twice with toluene (5 mL). To remove residual TEA and toluene, the sample was dried overnight on the high pressure vacuum pump providing 983 mg (>100%) of amine 2a as an orange oil. The sample was judged to be >95% pure by $^1$H NMR so was used without further purification. $^1$H NMR (CD$_3$OD): 7.62 (m, 1H), 7.57 (m, 3H), 4.65 (d, J=15 Hz, 1H), 4.53 (d, J=15 Hz, 1H), 4.13 (dd, J=9, 10.5 Hz, 1H), 3.41 (complex m, 2H), 2.56 (complex m, 1H), 2.01 (complex m, 1H); LC/MS: R$_t$ 1.68 min, (M$^+$+1) 259.1.

HPLC: R$_t$ 8.96 min, 96%; TLC: R$_f$ 0.35 (0.5% NH$_4$OH/5% MeOH/CH$_2$Cl$_2$ visualized by UV); $^1$H NMR (CD$_3$OD): 7.78 (s, 1H), 7.21 (d, J=8.4 Hz, 2H), 7.35-7.64 (complex m, 3H), 7.31 (d, J=8.4 Hz, 2H), 7.01 (s, 1H), 5.49 (s, 2H), 4.61 (brs, 1H), 4.57 (d, J=15 Hz, 1H), 4.47 (d, J=15 Hz, 1H), 3.85 (d, J=14.1 Hz, 1H), 3.72 (d, J=14.1 Hz, 1H), 3.47 (t, J=8 Hz, 1H), 3.23 (complex m, 1H), 2.23 (complex m, 1H), 1.69 (complex m, 1H); $^{19}$F NMR (CD$_3$OD): −64.5 (s); LC/MS: R$_t$ 3.99 min, (M$^+$+1) 454.2.

Example 1A

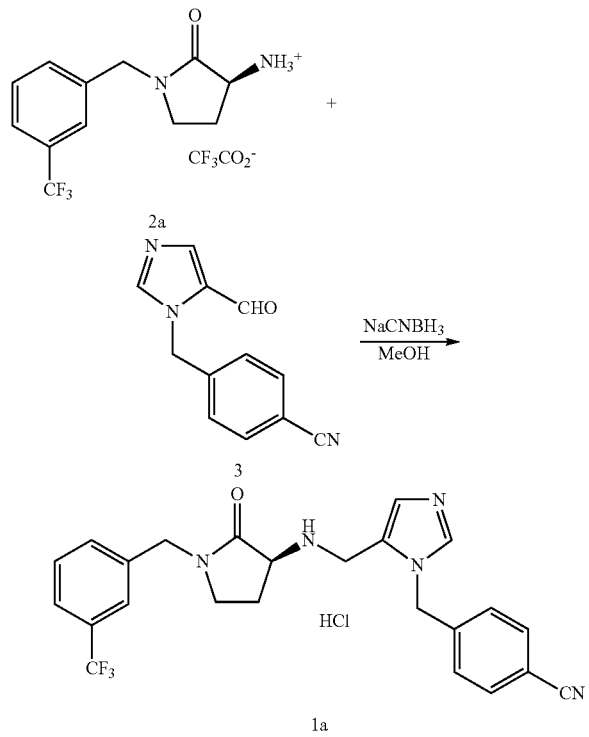

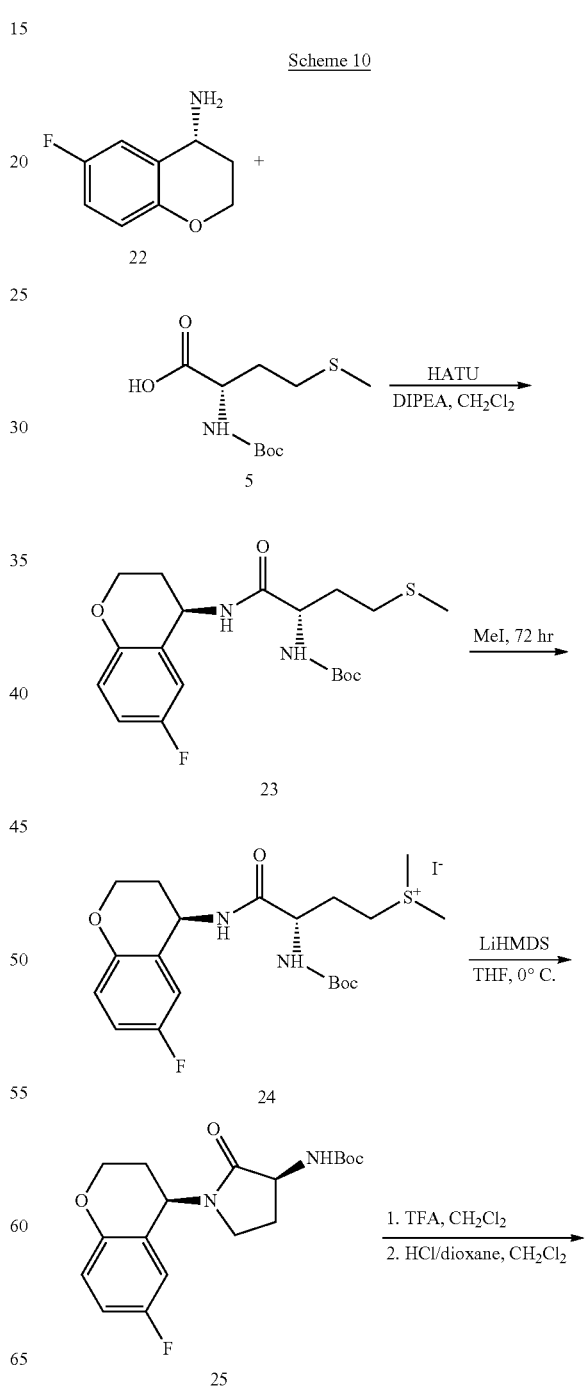

Procedure: In a 4 dram vial, pyrrolidone 2a (264 mg, 0.71 mmol) and aldehyde 3 (150 mg, 0.71 mmol, prepared in a manner substantially similar to that described in Williams et al., *J. Med. Chem.* 1999, 42, 3779) were dissolved in methanol (2.5 mL) and stirred for 1 hour at room temperature. To this was added sodium cyanoborohydride (62 mg, 0.99 mmol) and the reaction was stirred at room temperature overnight. The reaction was quenched with saturated sodium bicarbonate (4 mL) and the methanol was removed under vacuum. The aqueous solution was extracted twice with methylene chloride (5 mL), dried over sodium sulfate, filtered and concentrated to an oil. Initial purification using KP-NH$_2$ silica did not work well so the material was purified by preparative silica plate chromatography using four 1000 μM plates and eluting with 0.5% NH$_4$OH/5% MeOH/CH$_2$Cl$_2$. The amine 1a (115 mg) was dissolved in methylene chloride (4 mL) and 4N HCl in dioxane (65 μL) was added and the mixture stirred for 5 minutes. The volatiles were evaporated with a nitrogen gas stream to give the HCl salt 1a (122 mg, 35% yield, 96% pure).

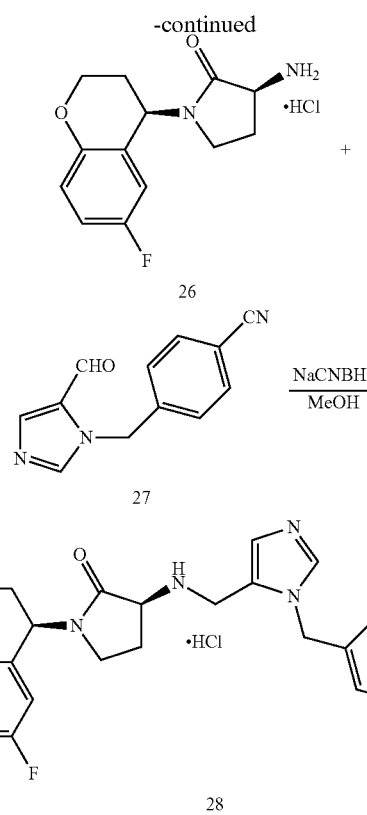

hour and then allowed to stir at room temperature for 16 hours. The reaction was quenched with 0.5M citric acid (8 mL) and the layers were separated. The aqueous layer was extracted two times with methylene chloride (10 mL). The organic layers were combined and washed once with brine (20 mL), dried over MgSO$_4$, filtered, and concentrated to a off white solid. The material was purified by filtration silica chromatography (60% ethyl acetate/hexane) to provide 877 mg (89%) amide 23 as a off white solid. TLC: R$_f$ 0.35 (40% ethyl acetate/hexane visualized by UV and iodine); $^1$H NMR (CDCl$_3$): 6.88 (m, 2H), 6.77 (m, 1H), 6.64 (brs, 1H), 5.14 (m, 2H), 4.23 (m, 2H), 4.13 (m, 1H), 2.58 (complex m, 2H), 2.19 (complex m, 1H), 2.12 (s, 3H), 1.98 (complex m, 2H), 1.42 (s, 9H); $^{19}$F NMR (CDCl$_3$): −123.31; LC/MS: amide 23, R$_t$ 8.15 min, 398.9 (M$^+$+1).

Prepared by the Same Procedure:

(R)-6-Chloro-chroman-amide 23: from (R)-6-chlorochroman-4-amine hydrochloride (500 mg, 2.27 mmol) isolated 752 mg 3 (80% yield); TLC: R$_f$ 0.30 (50% ethyl acetate/hexane visualized by UV and iodine); $^1$H NMR (CDCl$_3$): 7.12 (m, 2H), 6.76 (d, J=8.6 Hz, 1H), 6.63 (brs, 1H), 5.11 (complex m, 2H), 4.25 (complex m, 2H), 4.13 (complex m, 1H), 2.58 (complex m, 2H), 2.17 (complex m, 2H), 2.12 (s, 3H), 1.98 (m, 2H), 1.43 (s, 9H); LC/MS: R$_t$ 8.66 min, 415.0 (M$^+$+1).

(R)-7-Chlorotetrahydronaphthyl-amide 23: from (R)-7-chloro-1,2,3,4-tetrahydronaphthyl-1-amine hydrochloride (500 mg, 2.29 mmol) isolated 800 mg 3 (85% yield); TLC: R$_f$ 0.30 (40% ethyl acetate/hexane visualized by UV and iodine); $^1$H NMR (CDCl$_3$): 7.22 (d, J=2.0 Hz, 1H), 7.13 (ddd, J=8.2; 2.3; 1.6 Hz, 1H), 7.02 (dd, J=8.2; 2.7 Hz, 1H), 6.50 (brs, 1H), 5.15 (complex m, 2H), 4.24 (m, 1H), 2.74 (complex m, 2H), 2.69 (complex m, 2H), 2.14 (complex m overlapped by methanol, 1H), 2.12 (s, 3H), 2.01 (complex m, 2H), 1.80 (br complex m, 1H), 1.43 (s, 9H); LC/MS: R$_t$ 9.10 min, 413.1 (M$^+$+1).

Scheme 11

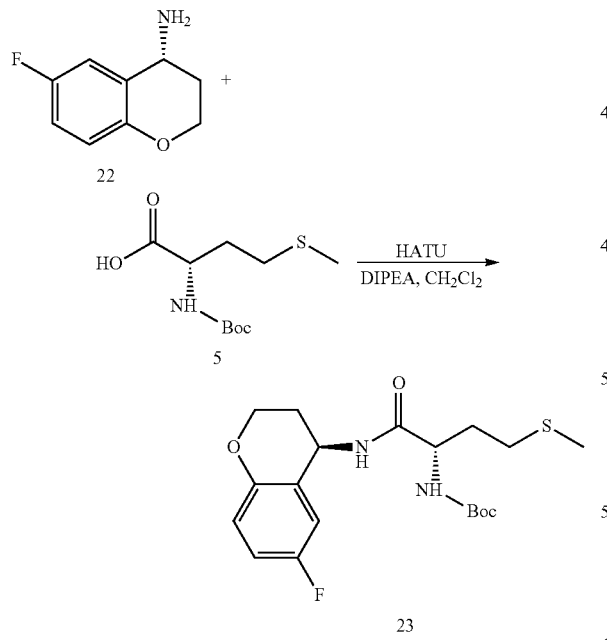

Procedure: To a mixture of Boc-L-methionine (631 mg, 2.53 mmol) in methylene chloride (8 mL) was added HATU (1.12 g, 2.95 mmol) and DIPEA (920 μL, 5.28 mmol) and the solution was cooled to 0-5° C. with an ice bath. (R)-6-Fluorochroman-4-amine hydrochloride (500 mg, 2.46 mmol) was added as a solid and the reaction was stirred at 0-5° C. for 1

Scheme 12

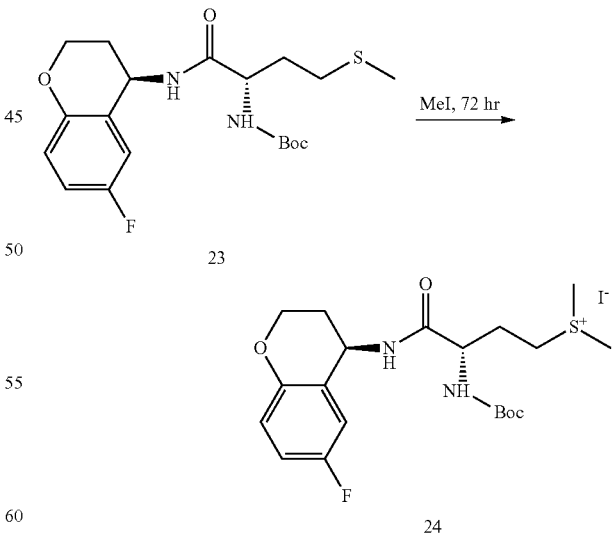

Procedure: Amide 23 (877 mg, 2.2 mmol) and 15 mL iodomethane were stirred at room temperature for 72 hours. Initially, the mixture was homogeneous but after 17 hours a tacky solid had precipitated. The reaction was diluted with ethyl acetate and stirred until a nice solid formed. The solid was collected by filtration to provide 1.0 g (83%) of the iodo salt 24 as a off white powder. $^1$H NMR (CD$_3$OD): 6.96 (dd, J=9.0; 6.6 Hz, 1H), 6.89 (m, 1H), 6.76 (m, 1H), 5.10 (t, J=6.3 Hz, 1H), 4.20 (complex m, 3H), 3.40 (complex m, 2H), 2.96 (s, 6H), 2.30 (complex m, 1H), 2.15 (complex m, 2H), 2.12 (complex m, 1H), 1.45 (s, 9H); $^{19}$F NMR (CDCl$_3$): −125.92; LC/MS: salt 24, R$_t$ 5.30 min, 413.1 (M$^+$).

Prepared by the Same Procedure:

(R)-6-Chloro-chroman-iodo salt 24: from (R)-6-chloro-chromane-amide 23 (752 mg, 1.8 mmol) obtained 694 mg 24 (69% yield); $^1$H NMR (CD$_3$OD): 7.22 (d, J=2.3 Hz, 1H), 7.12 (dd, J=8.3, 2.3 Hz, 1H), 6.77 (d, J=8.6 Hz, 1H), 5.08 (m, 1H), 4.21 (complex m, 3H), 3.39 (m, 2H), 2.96 (s, 6H), 2.29 (complex m, 1H), 2.15 (complex m, 2H), 2.03 (complex m, 1H), 1.45 (s, 9H); LC/MS: R$_t$ 6.20 min, 429.1 (M$^+$).

(R)-7-Chlorotetrahydronaphthyl-iodo salt 24: from (R)-7-chlorotetrahydronaphthyl-amide 3 (800 mg, 1.94 mmol) obtained 1.1 g, (100% yield); $^1$H NMR (CD$_3$OD): 7.25 (d, J=1.95 Hz, 1H), 7.12 (complex m, 2H), 5.05 (t, J=6.3 Hz, 1H), 4.20 (complex m, 1H), 3.43 (complex m, 2H), 2.98 (s, 6H), 2.77 (complex m, 2H), 2.30 (complex m, 1H), 2.15 (complex m, 1H), 1.92 (complex m, 1H), 1.81 (complex m, 1H), 1.45 (s, 9H); LC/MS: R$_t$ 6.68 min, 427.1 (M$^+$).

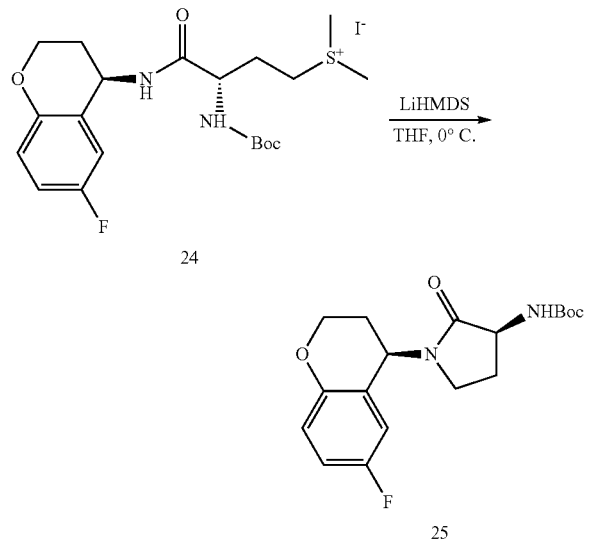

Scheme 13

Procedure: Compound 24 (1.0 g, 1.8 mmol) was dissolved in 40 mL anhydrous THF and cooled in an ice bath. A solution of 1M LiHMDS in THF (2.2 mL) was added dropwise and the reaction was stirred at 0° C. for 2 hours. The reaction was warmed to room temperature and stirred for an additional 16 hours. The reaction was quenched with saturated ammonium chloride (40 mL) and extracted twice with ethyl acetate (40 mL). The combined organic layers were washed with brine (80 mL), dried over MgSO$_4$, filtered, and concentrated to an off white solid. The material was purified by chromatography using a gradient (10-80% ethyl acetate/hexane) to provide 0.56 g (89%) pyrrolidone 25 as a white solid. TLC: R$_f$ 0.39 (60% ethyl acetate/hexane visualized by UV and iodine); $^1$H NMR (CDCl$_3$): 6.88 (m, 1H), 6.79 (m, 1H), 6.61 (m, 1H), 5.47 (m, 1H), 5.14 (brs, 1H), 4.28 (complex m, 2H), 4.20 (m, 1H), 3.20 (m, 1H), 3.07 (m, 1H), 2.63 (complex in, 1H), 2.17-2.10 (complex m, 21H), 1.89 (complex m, 1H), 1.47 (s, 9H); $^{19}$F NMR (CDCl$_3$): −123.03; LC/MS: amide 25, R$_t$ 7.21 min, 351.0 (M$^+$+1).

Prepared by the Same Procedure:

(R)-6-Chloro-chroman-pyrrolidone Boc amide 25: from (R)-6-chloro-chromane-iodo salt 24 (694 mg, 1.25 mmol) obtained 225 mg 25 (49% yield); $^1$H NMR (CD$_3$OD): 7.11 (dd, J=8.8; 2.5 Hz, 1H), 6.86 (d, J=2.7 Hz, 1H), 6.78 (d, J=8.9 Hz, 1H), 5.45 (m, 1H), 5.14 (brm, 1H), 4.29 (complex m, 2H), 4.20 (complex m, 1H), 3.19 (t, J=8.9 Hz, 1H), 3.07 (complex m, 1H), 2.64 (m, 1H), 2.14 (complex m, 2H), 1.89 (complex m, 1H), 1.47 (s, 9H); LC/MS: R$_t$ 7.70 min, 366.9 (M$^+$+1).

(R)-7-Chloro-tetrahydronaphthyl-pyrrolidone Boc amide 25: from (R)-7-chloro-tetrahydronaphthyl-iodo salt 24 (1.2 g, 2.16 mmol) obtained 359 mg 25 (46% yield); 7.13 (dd, J=8.4; 1.8 Hz, 1H), 7.05 (d, J=8.2 Hz, 1H), 6.89 (d, J=1.6 Hz, 1H), 5.37 (m, 1H), 5.18 (br s, 1H), 4.31 (complex m, 1H), 3.18 (complex m, 1H), 3.03 (complex m, 1H), 2.74 (m, 2H), 2.64 (complex m, 1H), 2.00 (complex m, 2H), 1.84 (complex m, 3H), 1.47 (s, 9H); LC/MS: R$_t$ 8.36 min, 365.0 (M$^+$+1).

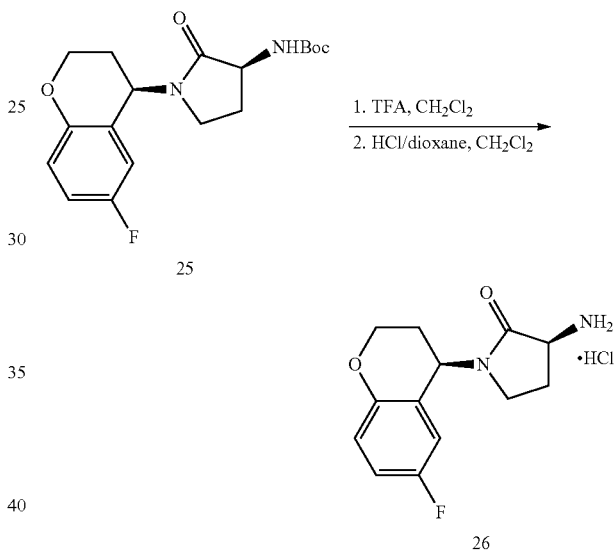

Scheme 14

Procedure: Pyrrolidone 25 (676 mg, 1.93 mmol) was dissolved in methylene chloride (5 mL) and cooled in an ice bath. Trifluoroacetic acid (2.4 mL) was added dropwise and the yellow solution was allowed to warm to room temperature and stirred for 2 hours. The reaction was concentrated under reduced pressure and diluted with 10 mL ethyl acetate. The mixture was basified carefully with saturated sodium bicarbonate solution and the layers were separated. The aqueous layer was extracted once with 4% methanol/methylene chloride. The combined organic layer was dried over sodium sulfate, filtered and concentrated to give an oil. The oil was dissolved in 2 mL methylene chloride and acidified with 480 uL 4M HCl in dioxane solution. The HCl salt of amine 26 was precipitated by addition of ether. The solid was sonicated to break up clumps, and stirred overnight. The solid was collected by filtration to provide 375 mg (68%) amine hydrochloride 26 as a off white solid. $^1$H NMR (CD$_3$OD): 6.93 (m, 1H), 6.81 (m, 2H), 5.37 (m, 1H), 4.25 (complex m, 3H), 3.40 (t, J=9.2 Hz, 1H), 3.21 (m, 1H), 2.56 (complex m, 1H), 2.23 (complex m, 1H), 2.11-2.01 (complex m, 2H); $^{19}$F NMR (CD$_3$OD): −125.37; LC/MS: R$_t$ 1.10 min, 251.0 (M$^+$+1).

Prepared by a Similar Procedure:

(R)-6-Chloro-chroman-pyrrolidone amine 26: from (R)-6-chloro-chromane-pyrrolidone Boc amide 25 (225 mg, 0.613 mmol) obtained 162 mg 26 (88% yield); $^1$H NMR (CD$_3$OD): 7.15 (d, J=8.6 Hz, 1H), 7.04 (s, 1H), 6.81 (d, J=8.6 Hz, 1H), 5.36 (t, J=6.9 Hz, 1H), 4.28 (complex m, 3H), 3.39 (m, 1H), 3.23 (m, 1H), 2.59 (m, 1H), 2.27 (m, 1H), 2.11 (m, 2H); LC/MS: R$_t$ 2.48 min, 266.9 (M$^+$+1).

(R)-7-chloro-tetrahydronaphthyl-iodo salt 24

(R)-7-Chloro-tetrahydronaphthyl-pyrrolidone amine 26: from (R)-7-chlorotetrahydro-naphthyl-pyrrolidone Boc amide 25 (359 mg, 0.98 mmol) obtained 246 mg 26 (83% yield); $^1$H NMR (CD$_3$OD): 7.16 (complex m, 2H), 7.03 (d, J=1.6 Hz, 1H), 5.28 (m, 1H), 4.28 (t, J=9.4 Hz, 1H), 3.39 (t, J=9.4 Hz, 1H), 3.17 (m, 1H), 2.78 (complex m, 2H), 2.58 (complex m, 1H), 1.93 (complex m, 5H); LC/MS: R$_t$ 3.33 min, 264.9 (M$^+$+1).

Scheme 15

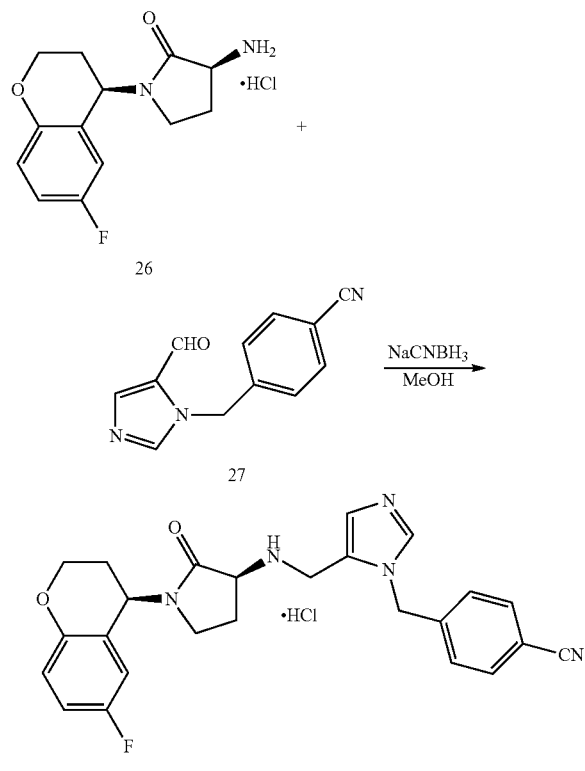

Procedure: In a 4 dram vial, pyrrolidone 26 (200 mg, 0.70 mmol) and aldehyde 27 (172 mg, 0.82 mmol), prepared in a manner substantially similar to that described in Williams et al., *J. Med. Chem.* 1999, 42, 3779) were dissolved in methanol (1.8 mL) and the pH of the solution was adjusted to around 5 using DIPEA and pre-wetted pH paper. After stirring for 1 hour at room temperature, sodium cyanoborohydride (51 mg, 0.82 mmol) was added and the reaction was stirred at room temperature overnight. The reaction was quenched with saturated sodium bicarbonate (4 mL) and the aqueous solution was extracted twice with methylene chloride (5 mL), dried over sodium sulfate, filtered and concentrated to an oil. The crude material was purified by flash silica chromatography using a gradient of 0-3% MeOH/CH$_2$Cl$_2$ containing 0.5% NH$_4$OH. The fractions containing the product were concentrated to an oil (157 mg), dissolved in methylene chloride (4 mL) and 4N HCl in dioxane (84 µL) was added. The salt was precipitated by addition of ether. The mixture was sonicated to break up any clumps and then stirred for 1 hour. The solid was isolated by filtration and dried in a vacuum oven overnight to provide the HCl salt of 28 (99 mg, 29% yield, >95% pure).

HPLC: R$_t$ 7.95 min, 100%; TLC: R$_f$ 0.35 (0.5% NR$_4$OH/5% MeOH/CH$_2$Cl$_2$ visualized by UV); $^1$H NMR (CD$_3$OD): 8.81 (s, 1H), 7.89 (d, J=8.2 Hz, 2H), 7.57 (s, 1H), 7.49 (d, J=8.2 Hz, 2H), 6.91 (td, J=8.2, 3.1 Hz, 1H), 6.81 (m, 1H), 6.79 (dd, J=9.0, 2.7 Hz, 1H), 5.72 (s, 2H), 5.35 (m, 1H), 4.32-4.02 (complex m, 3H), 3.81 (t, J=8.3 Hz, 1H), 3.35 (m under methanol peak, 1H), 3.07 (m, 1H), 2.35 (complex m, 1H), 2.21 (complex m, 1H), 2.04 (complex m, 1H), 1.86 (complex m, 1H); $^{19}$F NMR (CD$_3$OD): −125.48 (q); LC/MS: R$_t$ 3.17 min, (M$^+$+1) 446.1.

Prepared by the Same Procedure:

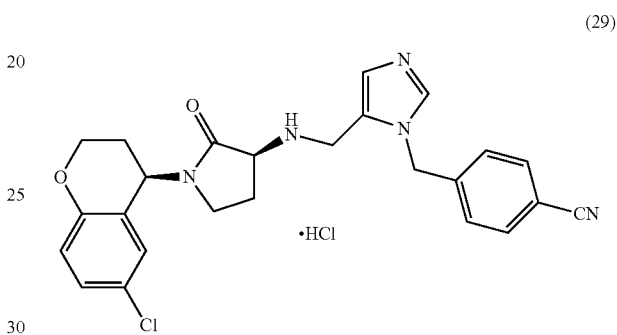

(29)

(R)-6-Chloro-chroman-pyrrolidone analog 28: from (R)-6-chloro-chromane-pyrrolidone amine 26 (268 mg, 0.88 mmol) obtained 127 mg 28 (48% yield); HPLC: R$_t$ 8.49 min, 91%; TLC: R$_f$ 0.35 (0.5% NH$_4$OH/5% MeOH/CH$_2$Cl$_2$ visualized by UV); $^1$H NMR (CD$_3$OD): 9.18 (d, J=1.2 Hz, 1H), 7.98 (s, 1H), 7.83 (d, J=8.2 Hz, 2H), 7.60 (d, J=8.2 Hz, 2H), 7.17 (dd, J=8.8; 2.5 Hz, 1H), 7.06 (d, J=1.95 Hz, 1H), 6.82 (d, J=8.9 Hz, 1H), 5.85 (s, 2H), 5.40 (m, 1H), 4.92 (overlapped with HOD peak), 4.56 (d, J=14.8 Hz, 1H), 4.46 (t, J=9.4 Hz, 1H), 4.29 (complex m, 2H), 3.46 (m, 1H), 3.23 (m, 1H), 2.64 (complex m, 1H), 2.26 (complex m, 2H), 2.15 (complex m, 2H); LC/MS: R$_t$ 4.43 min, 462.0 (M$^+$+1).

Prepared by the Same Procedure:

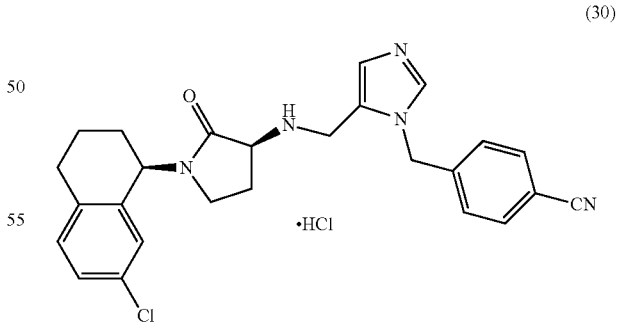

(30)

(R)-7-Chloro-tetrahydronaphthyl-pyrrolidone analog 28: from (R)-7-chlorotetrahydro-naphthyl-pyrrolidone amine 6 (246 mg, 0.82 mmol) obtained 250 mg 28 (61% yield); HPLC: R$_t$ 9.03 min, 90%; TLC: R$_f$ 0.35 (0.5% NH$_4$OH/3% MeOH/CH$_2$Cl$_2$ visualized by UV); $^1$H NMR (CD$_3$OD): 9.18 (d, J=1.2 Hz, 1H), 7.98 (s, 1H), 7.83 (d, J=8.2 Hz, 2H), 7.59 (d, J=8.2 Hz, 2H), 7.17 (complex m, 2H), 7.05 (s, 1H), 5.84 (s, 2H), 5.33 (m, 1H), 4.90 (m overlapped with HOD peak), 4.55 (d, J=14.8 Hz, 1H), 4.48 (t, J=9.4 Hz, 1H), 3.44 (t, J=9.4 Hz, 1H), 3.17 (complex m, 1H), 2.84-2.7 (overlapping m, 3H), 2.61 (complex m, 1H), 2.21 (complex m, 1H), 2.18-1.95 (overlapping m, 3H), 1.85 (complex m, 1H); LC/MS: $R_t$ 5.61 min, 460.1 (M$^+$+1).

Example 2

In Vitro Farnesyl Transferase Assay

Compounds were analyzed for inhibition of farnesyl transferase (FTase) activity using an established fluorescent peptide-based assay (Pompliano et al 1992 *J. Am. Chem. Soc.* 114:7945; U.S. Pat. No. 5,525,479, issued Jun. 11, 1996; each of which is incorporated herein by reference). In summary, a dansyl-pentapeptide (dGCVLS) was incubated at 4 µM with 5 µM farnesyl pyrophosphate (FPP) and 25-50 nM FTase in 50 mM Tris-HCl/12 mM MgCl$_2$/12 µM ZnCl$_2$/6 mM DTT/0.2% octyl-D-β-glucopyranoside/pH 7.0 at room temperature while the increase in fluorescence of the peptide at Ex=340 nm, Em=485 nm upon farnesyl addition was monitored continuously by a spectrofluorometer. Test compounds were added to the reaction mixture and the final results were compared to negative control (with solvent only), to allow measurement of the degreee of inhibition at each concentration of compound tested. Serial dilution series of test compounds were used to allow measurement of the IC50s and calculation of the resultant $K_i$. The linear portion of the reaction progress curve thus created was measured to yield an initial rate (Vo); a plot of Vo versus inhibitor concentration was fit by non-linear regression analysis (GraphPad Prism software) to calculate the IC % 0 and the $K_i$. All reactions in the inhibitor experiments contain a final concentration of 1% DMSO. Results for some exemplary compounds are shown in the table below.

| Compound No. | Structure | FTase assay Ki (nM) |
|---|---|---|
| 30 | 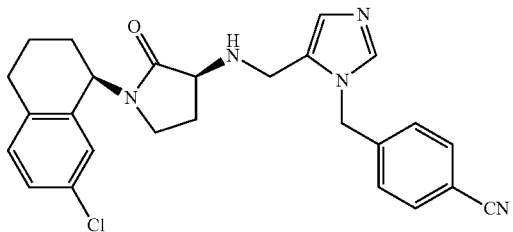 | 0.12 |
| 29 | 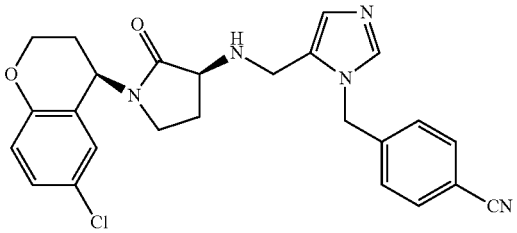 | 0.021 |
| 28 | 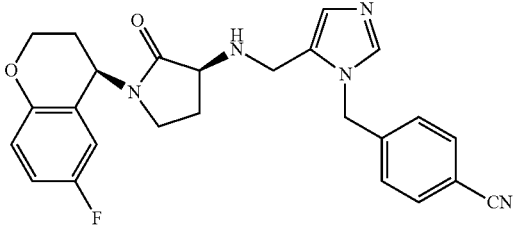 | 0.059 |

Example 3

Cellular Assay for Measurement of Farnesyl Transferase Activity

Ras is a small GTP binding protein whose farnesylation and condequent membrane association can be reduced by inhibition of farnesyl transferase (Appels et al., *Oncologist* 10:565-578, 2005; Basso et al., *J. Lipid Res.* 47:15-31, 2006; Tamanoi, *Trends Biochem. Sci.* 18:349-353, 1993; each of which is incorporated herein by reference). Treatment with certain farnesyl transferase inhibitors (FTIs) reduces the farnesylation and membrane association of Ras, leading to accumulation of Ras in the cytosol of the cells. An assay was developed to monitor FTase activity, based on the amount of Ras present in the cytosolic fraction of COS-7 cells after FTI treatment. On day 0, COS-7 cells were passaged into 6-well plates at a density of $4 \times 10^5$ cells/well. Beginning on day 1, cells were treated with test compounds (e.g. FTIs) in 0.2% DMSO for 24 hr. On day 2, cells were lysed by passage through a 25 gauge needle 10 times in 100 μl Buffer 1 (50 mM Tris, 140 mM NaCl, 2 mM EDTA, protease inhibitor cocktail, pH 7.4) and lysates were centrifuged at 16,000 g for 30 min to isolate the cytosolic fraction (supernatant). The cytosolic fraction was analyzed by Western blot using anti-Ras antibody and anti-actin antibody for loaning control.

Western Blotting: Following transfer of SDS gels onto NC membrane, all membranes were blocked with 5% non-fat milk in TBST (50 mM Tris-HCl pH7.4, 150 mM NaCl, 0.1% Tween 20), incubated with primary antibody overnight with 1% BSA in TBST, washed three times with TBST, and incubated with horseradish peroxidase-conjugated secondary antibody for 1 hour (Promega). Bound antibodies were detected using enhanced chemiluminascence (NEM). Results were quantified based on densitometric analysis of Ras signal normalized to actin signal (Ras/actin ratio). Dose response curves were generated for serial dilutions of test compounds, which were then used to measure an IC50 for the test compound by curve fitting with Prism or equivalent software product. Results for some exemplary compounds are shown in the table below:

| Compound No. | Structure | Cell IC50 (nM) |
|---|---|---|
| 30 | 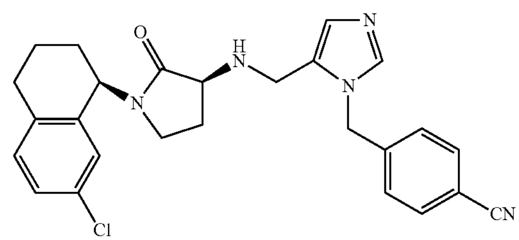 | 2.8 |
| 29 | 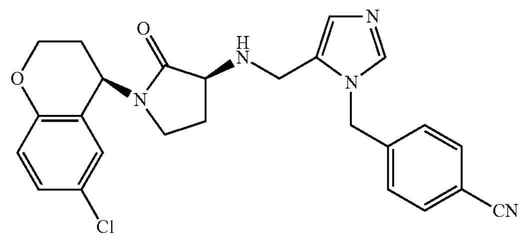 | 1.8 |
| 28 | 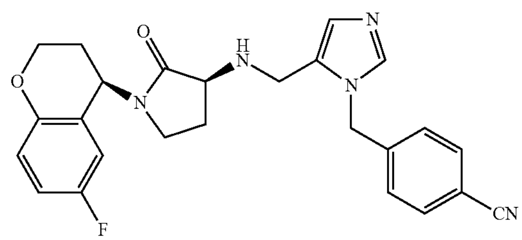 | 1.4 |
| 70 | 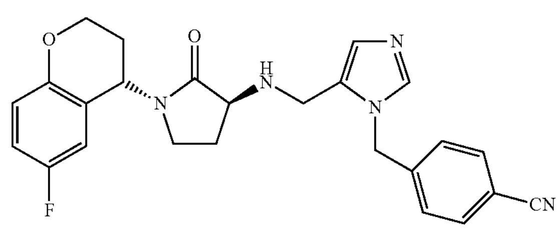 | 42 |

| Compound No. | Structure | Cell IC50 (nM) |
|---|---|---|
| 71 | 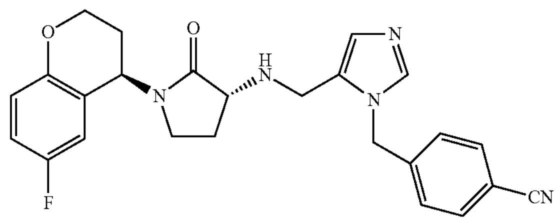 | 2.5 |

Example 4

Treatment with FTI Decreases α-Synuclein Levels in the Brain

Farnesyl transferase inhibitors and other test compounds are administered to mice of the α-synuclein transgenic line described in Masliah et al. (Masliah et al. "Dopaminergic loss and inclusion body formation in alpha-synuclein mice: implications for neurodegenerative disorders" *Science* 287(5456): 1265-69, 2000; incorporated herein by reference). This assay serves as a general model for multiple types of proteinopathies, although it is based on α-synuclein. Animals from the line referenced have α-synuclein neuronal inclusions in the cortex, hippocampus, and the olfactory bulb (Masliah et al. "Dopaminergic loss and inclusion body formation in alpha-synuclein mice: implications for neurodegenerative disorders" *Science* 287(5456):1265-69, 2000). Transgenic mice are orally administered different doses of either test compound in vehicle or the same volume of vehicle alone once or twice a day for 30 or 90 days. In some cases, non-transgenic mice also receive the test compound in vehicle, or vehicle alone once or twice a day for 30 to 90 days. At the end of treatment, mice are sacrificed, and the brains are removed and hemisected. One hemisphere of each is fixed in 4% paraformaldehyde/PBS (pH 7.4), cryopreserved, then sectioned for histology. The other hemisphere is subdivided into four brain regions, including the cortex and hippocampus, that are homogenized and processed into cytoplasmic and membrane fractions.

Formation of α-synuclein inclusions in the cortex and hippocampus is probed by immunostaining with an antibody for human α-synuclein. Cells positive for human α-synuclein are quantified. Brain sections were stained with a monoclonal human α-synuclein specific antibody (Alexis®; Cat# 804-258-L001; dilution 1:5), followed by a secondary Ab Cy 2-Goat Anti-Rat (Jackson ImmunoResearch®; dilution 1:200). IR positive cells were quantified using microscopy and specialized image analysis software (Image Pro Plus, version 4.5.1.29). Total α-synuclein levels in specific brain regions of treated animals are analyzed by a sandwich ELISA assay similar to one previously described (El-Agnaf et al. "Detection of oligomeric forms of alpha-synuclein protein in human plasma as a potential biomarker for Parkinson's disease" *FASEB J.* 20(3):419-25, 2006; incorporated herein by reference). In the cortex of the vehicle treated animals, α-synuclein protein levels in both cytoplasmic and membrane fractions in the brains of test compound treated α-synuclein transgenic mice are measured and compared with vehicle treated mice.

Brain homogenate was centrifuged and the supernatant saved as fraction F1. The pellet was washed then resuspended and saved as fraction F2. Plates (Nunc, 464718) were coated with the anti <-synuclein antibody SYN-1 (1:1000, BD Transduction Labs, 610787). Monomeric recombinant <-synuclein was included as an internal standard. Biotinylated antibody FL-140 (1:300, Santa Cruz Biotechnology, sc-10717-B) and ExtrAvidin-Alkaline phosphatase (3:5000, Sigma, E2636) was added followed by pNPP substrate solution (Sigma, N1891). Raw absorbance (405 nm) was then normalized to the total protein concentration of each sample. Concentration of α-synuclein in test samples was determined by comparison with a standard curve.

Treatment with test compounds as above decreases levels of α-synuclein protein in either the cortex, or the hippocampus, or in both, as measured by immunohistochemistry or ELISA.

Example 5

Measurement of Autophagy Stimulation In Vitro

Cell culture media and reagents were purchased from Gibco. SH-SY5Y cells were grown in DMEM medium supplemented with 10% FBS and 1% pen/strep at 37° C. and 5% $CO_2$. Cells were plated in either 12 well plates for qPCR or 8 well chamber slides for immunohistochemistry, and allowed to grow until 70% confluent. Cells were then differentiated with 10 µM retinoic acid for 72 hr. Differentiated cells were then treated with the either rapamycin (100 nM or 1 µM) as a positive control, or with test compounds for 48-72 hr. For immunohistochemistry, cells were then fixed with 4% paraformaldehyde/PBS or ice cold methanol. Cells were then stained for LC3 (Novus biological, NB100-2331, dilution1: 800) followed by secondary Alexa-564 Anti-Rabbit (A-11011). Slides were then mounted using ProLong Gold antifade reagent with DAPI (Invitrogen).

For Western analysis of LC3-I and LC3-II ratio changes as a measurement of autophagy, SH-SY5Y cells were differentiated with 10 uM retinoic acid for 2-4 days prior to treatment with either DMSO or a test substance for 48-72 hr. For the last 18 hr, cells were treated with 5 nM bafilomycin A1. Cells were lysed in SDS-PAGE sample buffer and LC3-II levels were analyzed by Western blot, normalized to actin, and plotted relative to control cells treated with DMSO only (no bafilomycin). Antibodies used were anti-LC3B (Cell Signaling #2775) and anti-actin (Chemicon MAB1501R).

Autophagy gene expression profiles were done by qPCR on series of known autophagy genes. For cells used for qPCR, total RNA was extracted using Tri-reagent (Sigma) according to the manufacturer's specifications. The targeted genes and primers used are listed below. The primers (18-22 mer) were designed using Primer3 (http://wwwgenome.wi.mit.edu/cgi-bin/primer/primer3_www.cgi). These primer sets were designed to amplify small amplicons for candidate mRNAs ranging from 100-300 bp in size. First-strand cDNA synthesis was carried out on total RNA extracted with Tri-reagent (Sigma), using iScript cDNA synthesis kit (Biorad) according to the manufacturers specifications. qPCR analysis was carried out in a 96 well plate using an iCycler (BioRad, Hercules, Calif.), and iQ SYBR Green Supermix (Biorad) according to the manufacturer's specifications. A concentration curve with known concentrations of cDNA extracts from undifferentiated SH-SY5Y was used to calculate standard curves. The final concentration of each transcript was calculated using the myIQ2 software provided by Biorad followed by normalization to GAPDH (normalization to actin gave similar results).

| Primer sets | Gene name |
|---|---|
| AACGGATTTGGTCGTATTGG (SEQ ID NO. 2) | L-h-GAPDH |
| GCTCCTGGAAGATGGTGATG (SEQ ID NO. 3) | R-h-GAPDH |
| AAGCCATCAAGGTGATGAGG (SEQ ID NO. 4) | R-h-ATG1 |
| GGTCACACGCCACATAACAG (SEQ ID NO. 5) | L-h-ATG1 |
| ATCACCTAGTCCACCACTGTCC (SEQ ID NO. 6) | L-h-ATG3 |
| GTATCTACCATCCGCCATC (SEQ ID NO. 7) | R-h-ATG3 |
| TTATGTCATGTCGGGTGTGG (SEQ ID NO. 8) | L-h-ATG4 |
| ACAGGTGTAGGGCTCTGTG (SEQ ID NO. 9) | R-h-ATG4 |
| GAGGAAAGCAGAGGTGATGC (SEQ ID NO. 10) | R-h-ATG5 |
| GAGGCAACCTGACCAGAAAC (SEQ ID NO. 11) | L-h-ATG5 |
| GGTTGAGAAAGGCGAGACAC (SEQ ID NO. 12) | L-h-ATG(beclin 1) |
| TGAGGACACCCAAGCAAGAC (SEQ ID NO. 13) | R-h-ATG6 |
| GAACATGGTGCTGGTTTCCT (SEQ ID NO. 14) | L-h-ATG7 |
| CATCCAGGGTACTGGGCTAA (SEQ ID NO. 15) | R-h-ATG7 |
| AGGGACAACCCTAACACGAC (SEQ ID NO. 16) | R-h-ATG8 (LC3) |
| AGCAGGAGAAAGACGAGGAC (SEQ ID NO. 17) | L-h-ATG8 (LC3) |
| GAAGCTGCAACACAGACTGC (SEQ ID NO. 18) | R-h-ATG12 |
| TTGAATGACTAGCCGGGAAC (SEQ ID NO. 19) | L-hATG12 |
| GCATGGCCATCTTCTCTTTC (SEQ ID NO. 20) | R-h-p62. |
| TGGATGGGACTCCATAGCTC (SEQ ID NO. 21) | L-h-p62 |

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

Example 6

Effect on Oxygen Consumption

Impaired mitochondrial function is shown by a decreased rate of oxygen consumption. For example, INS1 cells exposed to palmitate show a significant decrease in oxygen consumption rate, both under basal glucose and following stimulation with glucose. The effect of compound 28 at 1 nM on oxygen consumption was determined at 2.5 and 3.5 day incubation time points. Oxygen consumption in INS1 was measured using a Seahorse XF24 bioenergetic assay. Assays have been previously described in detail (See, Wu M, et al. Am J Physiol Cell Physiol 2007; 292:C125-36).

In one aspect, islet oxygen consumption was measured using the XF24 Islet Capture Microplate available from Seahorse Biosciences. An example of an assay to measure islet consumption is as follows:

Reagents, Materials, and Injected Compounds

Modified XF Assay Media (MA Media): Supplement XF DMEM assay media with 3 mM glucose and 1% FBS to run whole islets. (FBS is needed to prevent islets from becoming too adherent). Components/Formulation of Modified XF Assay Media:

| Compound | Brand | Catalog Number | MW or Molar Concentration | Final Concentration | Grams or ml for 500 ml of XF Assay Media |
|---|---|---|---|---|---|
| Glucose | Sigma | G7528 | 180 | 3 mM | 0.27 g |
| FBS | Hyclone | SH30070.03 | 100% | 1% | 5 ml |

Components/Formulation of compounds to affect mitochondrial function.

| Compound | Brand | Catalog Number | Final Concentration | Dissolve in: |
|---|---|---|---|---|
| Rotenone | Sigma | R8875 | 5 µM | Stock 1000X in DMSO Dilute to 10X in MA Media |
| Oligomycin | Sigma | O4876 | 5 µM | Stock 10000X in DMSO Dilute to 10X in MA Media |
| FCCP | Sigma | C2920 | 1 µM | Stock 10000X in DMSO Dilute to 10X in MA Media |
| Glucose | Sigma | G7528 | 20 mM | Stock 1000X in DMSO Dilute to 10X in MA Media |
| Myxothiazol | MP Biomedicals | 155765 | 5 uM | Methanol |

Note:
Oligomycin, FCCP, rotenone, and myxothiazol should be freshly diluted in MA Media for each experiment. Stock solutions in DMSO may be stored at −20° C.

The XF assay template is prepared via the Assay Wizard using the XF24 operation manual. The assay template is uploaded to the XF24 Analyzer before starting the assay. The XF sensor cartridge is prepared. The XF sensor is hydrated overnight in XF Calibration Buffer at 37 degrees C., without CO2.

Whole islets are prepared by standard laboratory procedure. For example ~8 mice are sacrificed to obtain ~1200 islets—enough for 20 wells at 70 islets/well. Whole islets are incubated in a petri dish overnight under standard conditions for islet culture (e.g., culture islets in RPMI media with 11 mM glucose, 10% FBS, and 1% pen/strep). Whole cell islets and capture screens are added to the wells according to the following procedure: Islets are aspirated from Petri dish and dispensed into a 50 ml tube, washed 1× in MA Media. The supernatant is removed and cells are re-suspended in 2 ml MA Media. While creating turbulence in the tube with a pipettor, 20 microliter aliquots are removed and drops placed on a culture dish—three drops total. The islets are counted under a dissecting microscope. This gives an average amount of islets per volume from which the total number of islets is estimated. The count of the islets is determined and the volume adjusted so that there are ~70 islets for every 100 microliters of the islet suspension. The final volume should be 500 microliters per well. When the islets are seeded, a 20 microliter pipette is used to remove the islets into the depressed chamber at the bottom of the well. This is repeated so that each well gets a total of 100 microliters of media (700 islets/ml). 400 microliters of MA Media is added to each well of the XF24 islet plate. 50 microliters of the islet suspension is added to each well and repeated so that each well has a total of 100 microliters of the islet suspension. The final volume is 500 microliters per well. The islets are seeded using a 20 microliter pipette and all of the islets are moved into the depressed chamber in the bottom of the well. A dissecting microscope is used to be sure that all of the islets are in the depression at the bottom of the well. Screens are added by pre-wetting them in MA Media in a small petri dish to remove any air bubbles. A pair of sterile forceps is used to position the screens so that the ring is facing up. The islet capture screens are placed in the bottom of each well using a capture screen insert tool—being careful not to cause too much turbulence so as to keep the islets resting in the depression at the bottom of the well. The islet capture screen is released into the well by pulling up on the T-lever on the capture screen insert tool. The islet capture rings are stuck firmly at the bottom of the well. This is confirmed by gently pushing the screens down with a blunt tip pipette tip. The microplate is placed in an incubator set at 37 degrees Celsius, without CO2. The microplate is stored in the incubator for at least one hour to equilibrate temperature and to adjust islet metabolism to 3 mM glucose. While the plate is incubating, the XF sensor cartridge injection ports are prepared with the desired injections (see, table below) and calibrated.

| Injection Ports | Volume | Concentration in | Final Concentration in |
|---|---|---|---|
| A: Glucose | 50 µl | 200 mM | 20 mM |
| B: Oligomycin | 55 µl | 50 µM | 5 µM |
| C: FCCP | 60 µl | 10 µM | 1 µM |
| D: Rotenone | 65 µl | 50 µM | 5 µM |
| D: Myxothiazol | 65 µl | 50 µM | 5 µM |

Note:
Vigorous mixing of the stock 20 uM oligomycin is required to prevent precipitation.
Rotenone and Myxothiazol are mixed together in the appropriate concentrations for injection.

After the cartridge is filled with compounds for injection, the cartridge is loaded and the program and calibration started. When the XF24 calibration is complete, the islet plate is placed into the XF24. After the program is complete, normalization is done by counting the number of islets per well with the dissecting microscope.

Figure 2:
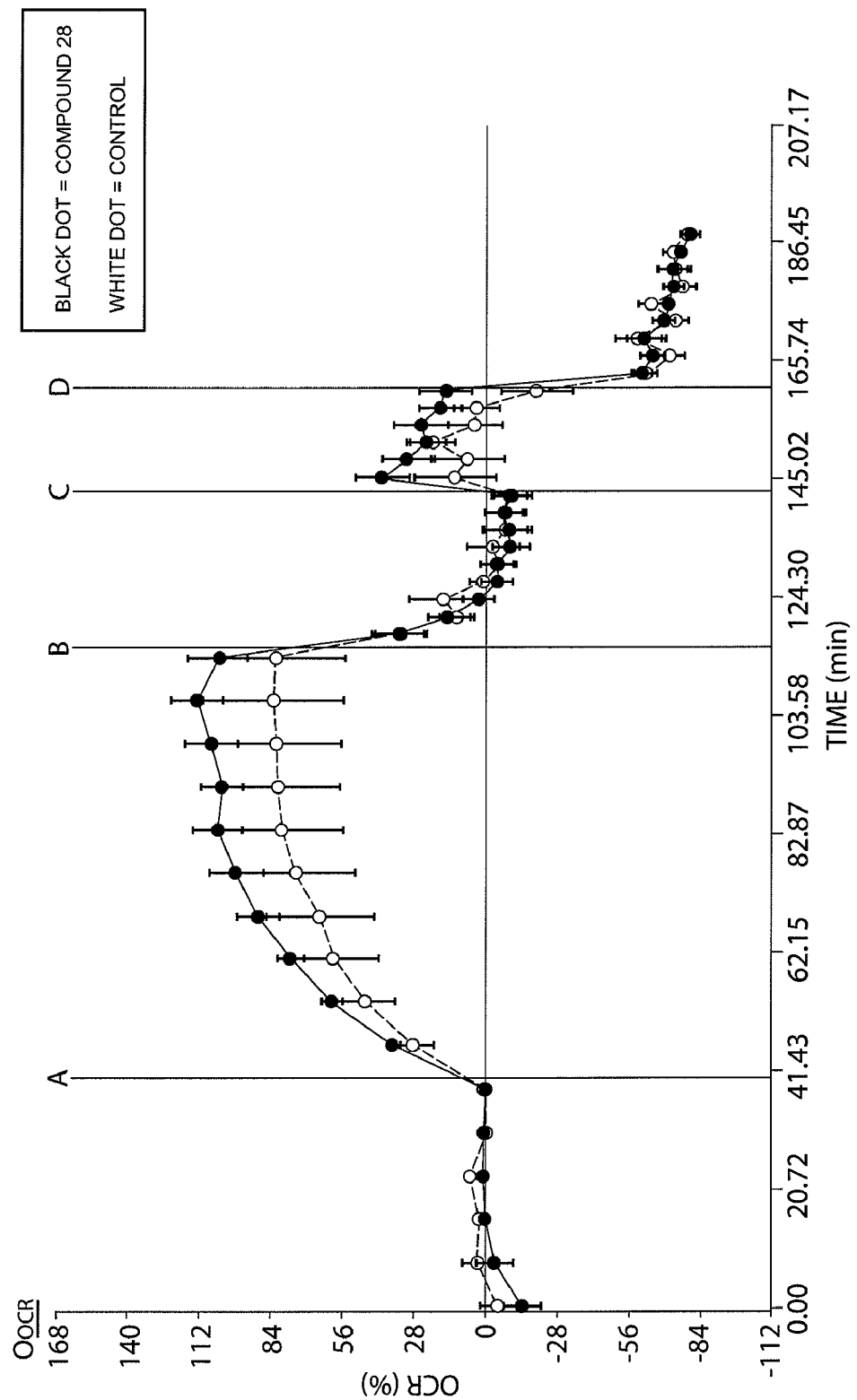
FIG. 2 is a graph that shows respiratory of compound 28 at 1 nM/3.5 days incubation; Oxygen Consumption Rate (OCR) vs. time (% of base line)(Avg).

FIGS. 1 and 2 show the respirometry of compound 28 Oxygen Consumption Rate vs time (% of baseline) (Avg). Compound 28 (1 nM) increases oxygen consumption by 50% in isolated islets.

Example 7

Effect on INS1 Cell Viability/Apoptosis in the Presence of Glucolipotoxicity (GLT)

Glucolipotoxicity (GLT) refers to exposure to high concentrations of both high glucose and high lipids and is a standard condition that is known to injure insulin-secreting beta cells (INS1 cells). Fatty acids and glucose impair insulin secretion and induce beta-cell death by a mechanism that was recently reported to involve macroautophagy (also referred to as "autophagy"). Nutrient abundance, i.e., high glucose or high palmitate or oleate increase the number of autophagosomes (APs) in vitro and in vivo in beta-cells and in liver cells. For example, palmitate derivatives such as ceramide have been implicated in lipotoxicity acting to impair autophagic flux in different cell types. Induction of autophagic flux is associated with cellular quality control mechanism, while impaired autophagic flux is associated with the accumulation of damage that may lead to malfunction and death at the cellular level, and to various diseases at the level of the organism.

Compounds of the invention are tested using a cell death assay to determine whether they have any effect on palmitate-induced cell death. For Example, one example of such an assay is as follows: INS1 cells are incubated in control medium or in medium containing palmitate for 18 hours and either rapamycin or a compound of the invention at 0.25 nM, 0.5 nM, 1 nM, 10 nM, and 100 nM is added for the last 12 hours of incubation. At the end of the incubation, the cells are washed with PBS and stained with 1 µg/ml propidium iodide (e.g., Molecular Probes, P3566). FACS data analysis is performed and cell debris is excluded. Rapamycin has been shown to protect cells from the toxic effect of palmitate. Compounds of the invention protect INS1 cells from palmitate toxicity.

Example 8

Effect on Glucolipotoxicity-Induced Mitochondrial Fragmentation in INS1 Cells

Mitochondrial fragmentation is a hallmark of beta cell dysfunction and type 2 diabetes. It is well-known that INS1 cells, when treated with palmitate, reproduce the abnormal fragmented mitochondrial phenotype that is characteristic of diabetic islet cells (See also, for methods and procedures for culturing INS1 cells, Molina et. al. Diabetes, vol. 58, October 2009). Preventing fragmentation is sufficient to prevent apoptosis.

To determine the effect of the compounds of the invention on glucolipotoxicity-induced mitochondrial fragmentation, a compound of the invention at 1 nM and 100 nM concentrations is cultured with INS1 cells in media containing palmitate according to methods and procedures described in Molina et. al. 2009. Imaging analysis is used to determine to the extent to which the compound normalizes mitochondrial morphology.

Example 9

Effect on Insulin Secretion Under Glucose Stimulated Conditions

An insulin secretion assay is used to determine whether compounds of the invention have an effect on insulin secretion conditions. One example of such an assay is as follows: prior to glucose-induced insulin secretion, cells are cultured for two hours in RPMI containing 3 mM glucose without serum. Cells are then washed and preincubated for 30 min in modified Krebs-Ringer bicarbonate buffer (KRB) containing (in mM): 119 NaCl, 4.6 KCl, 5 NaHCO$_3$, 2 CaCl$_2$, 1 MgSO$_4$, 0.15 Na$_2$HPO$_4$, 0.4 KH$_2$PO$_4$, 20 HEPES, 2 glucose, 0.05% BSA, pH 7.4. This is followed by 30 min incubation in media containing either 3 mM glucose (to simulate low glucose conditions) or 15 mM glucose (to simulate high glucose conditions). Media are treated with varying concentrations of compound (1 nM and 10 nM). Media was collected and stored at −20° C. for insulin measurement. Insulin is measured by ELISA. Compounds which stimulate insulin secretion at high glucose conditions but not at basal glucose levels provide an advantage over sulfonyl urea compounds, the current standard oral anti-diabetic drug, which increases insulin secretion under all conditions (not desired).

Example 10

Enhancement of Mitochondrial Dynamics

Mitochondrial dynamics are necessary for the maintenance of bioenergetic functions and maintenance of homogenous population of mitochondria. Mutations in Mfn2 and Opa1 have been implicated in neuropathies. A whole cell fusion assay is used to evaluate the effect of compounds of the invention on the enhancement of mitochondrial fusion and fission events. Photo-activateable GFP is used to label and follow an individual mitochondrion. Photo-activatable GFP becomes fluorescent only after absorbing UV light. Mitochondria undergo frequent fusion and fission. During fusion, the labeled mitochondrion passes fluorescent GFP to a neighboring unlabeled mitochondrion (Molina and Shirihai, Medical Informatics Europe (MIE), 2009). A diffusion of dye indicates that bioenergetics are increased i.e., there is an increase in mitochondrial fission and fussion events. The following assay protocol is followed: paGFP expression is carried out using adenoviral transduction if INS-1 cells. The cells are treated for 48 hours with a compound of the invention. Mitochondria are labeled with TMRE to facilitate tagging. UV pulse is delivered by two-photon laser. Z-stacks of individual cells are taken every 5 minutes for 30 minutes. Three separate runs are performed over 3 weeks at imaging facilities.

Further detail regarding the assay protocol in general are noted below.

Targeting PAGFP to the mitochondrial matrix delineates the borders of a mitochondrion. By photoconverting regions within a mitochondrion with a 2 photon laser, photoconverted GFP molecules in the matrix will trace the extent of luminal continuity as GFP molecules move freely through the matrix space. The movement of GFP within this space is not hindered despite protein density and high viscosity of the matrix. In addition to quantifying mitochondrion size, the diffusion ability of GFP molecules within the mitochondrial matrix can be used to observe mitochondrial fusion events in real time. PAGFPmt can be used alone or in combination with other probes for a number of different applications that can measure the following parameters; mitochondrial movement, membrane potential of individual mitochondria over time, fusion frequency, fusion site/localization, fusion rate of a cell's mitochondrial population, and the transfer and organization of proteins in fusing mitochondria. The methodologies described can be easily applied to the measurement of all these parameters.

The photoactivateable form of green fluorescent protein increases fluorescence intensity 100 fold after irradiation with 413 nm light. The development of a photoactivatable GFP that is useful at physiological conditions has opened new doors in the study of temporal and spatial dynamic interactions within a cell. Combined with 2 photon laser stimulation, it is possible to specifically stimulate individual organelles within a living cell and to monitor its interactions with other organelles.

Wild type GFP is a mixed population of fluorophores with a major and minor absorbance peaks at 397 nm and 475 nm respectively. Intense illumination with ultraviolet light causes the fluorophore population to give rise to the anionic form which demonstrates an increase in the minor peak absorbance. This causes an increase in fluorescence with subsequent 488 nM excitation. PAGFPmt is a variant that possesses a minor absorbance peak (475 nM) that is significantly lower than wildtype. This further enlarges the increase in fluorescence emission detected following photoconversion if excitation is done with a 488 nm laser.

A mitochondrial targeting sequence to PAGFP cDNA was added. DNA coding for the mitochondrial targeting sequence of COXVIII was amplified by PCR and inserted 5' to GFP thereby targeting it to the mitochondrial matrix. Transfection of this construct works well in many systems such as COS7 cells, primary human myocytes, hippocampal neurons, and MEF cells. Expression of PAGFPmt becomes evident after 48 hours. PAGFPmt expression can be visualized by eye with blue light excitation and green emission. Alternatively expression can be verified by western blot analysis with GFP antibody. Transfection is a stressful treatment and in some cells may lead to a change in mitochondrial architecture and dynamics. If cells are transfected with the PAGFPmt plasmid using lipofection, it is recommended that mitochondrial architecture of transfected and non transfected cells be compared. Some level of mitochondrial fragmentation has been observed to occur due to the stress of lipofection in the clonal beta cell line, INS1. To prevent lipofection induced stress, lentiviral and adenoviral vectors were generated. Although the initial infection may cause some degree of cell death (1-10%) after 48 hours, this becomes less evident over time and is not observed in subsequent passages of the cell line.

PAGFPmt for lentiviral and adenoviral delivery using pWPI (Trono) or pAdEasy (Adenoeasy) respectively have been packaged. Lentiviral transduction is highly efficient in cell lines such as INS1 while adenoviral transduction exhibits better efficiency in primary preparations such as beta cells from the islets of Langerhans. In addition, lentiviral transduction allows the PAGFPmt to integrate into the host genome. Expression is stable for as many as 10 passages. Freezing the cells and storing in liquid nitrogen leads to noticeably lower expression when the cells are thawed for use. This may be due to selection influences during the freeze thaw cycle.

By tagging individual mitochondria with photoconverted PAGFPmt, individual fusion events are observed. These events occur under normal conditions and without stimulation or stress. By generating time lapse, these events and quantification of their occurrence is captured. A fusion event is characterized by the transfer of photoconverted PAGFPmt molecules from the tagged mitochondrion to another previously unlabeled unit. Fission events typically follow fusion events and are characterized by the loss of PAGFPmt continuity. The average duration of a fusion event is ~1 minute. It is notable that fission can occur without a change in the apposition of the two daughter mitochondria, a process referred to as "hidden fission". Fission events often generate daughter mitochondria with disparate membrane potential that can be appreciated when using a potential sensitive dye such as TMRE. Daughter mitochondria resulting from a fission event will appear more red when hyperpolarized and stained with TMRE or more green when depolarized due to the presence of PAGFPmt. Therefore, some "hidden fission" events can be identified by the two daughter mitochondria having disparate changes in membrane potential.

Mitochondria were labeled with the mitochondrion-specific dye tetramethylrhodamine ethyl ester perchlorate (TMRE; Invitrogen). TMRE concentration should be adjusted for the cell type with a low concentration being preferred. Keep in mind that laser toxicity is proportional to the dye concentration in the mitochondria. Typically, for freshly isolated primary cells 3-5 nM should be sufficient; immortalized cell lines may require higher concentrations, 7-15 nM. Freshly prepared TMRE was added to culture in DMSO to give a final concentration and incubated for 45 min in a 37C incubator before imaging. Cells loaded with TMRE should be kept in dark to avoid phototoxicity. At the end of the loading period, the dye is not removed from the media. TMRE can be used to dynamically monitor membrane potential in mitochondria. Increases in TMRE fluorescence indicate hyperpolarization while decreases report depolarization. Since membrane potential influences mitochondrial fusion, it is expected that mitochondria with reduced TMRE intensity will have reduced probability for a fusion event within the duration of the experiment. During a fission event the concentration of matrix targeted mtPAGFP in the two daughters is identical. It is therefore possible to use the ratio (R) of TMRE/mtPAGFP for ratio imaging and comparison of membrane potential between the two daughter mitochondria generated during the fission event. The membrane potential difference between daughter (a) and daughter (b) can be calculated in millivolts $\Delta\Psi=61.5\mathrm{Log}(Ra/Rb)$ in experiments performed at 37 C.

Other fluorophores such as the dsRED protein and Mitotracker Red dye (MTR, Invitrogen) can be used to identify and characterize non fusing mitochondria. In mitochondria, it has been observed that slight increase in the intensity of 2-photon laser (750 nm) will result in dsRED bleaching during the photoconversion of PAGFPmt. This characteristic can be used to identify non fusing mitochondria, because these will have very high dsRED fluorescence. In addition, cells expressing mitochondrial dsRED can be fixed with 4% paraformaldehyde for 15 minutes while preserving fluorescence and mitochondrial architecture. This allows the user to further characterize the non-fusing mitochondrial subpopulation. For example, using an antibody to probe for the mitochondrial fusion protein OPA1 in fixed cells, it has been found that OPA1 expression is decreased in the non-fusing population. MTR loading into mitochondria is dependent on $\Delta\Psi$. Therefore, short pulses of MTR exposure can be used to identify polarized mitochondria versus those that are depolarized. Once the dye is loaded, it does not leave the mitochondria during fixation allowing further characterization of MTR stained mitochondria by immunofluorescence.

Cells transfected or virally transduced with PA-GFPmt should be allowed to accumulate the protein in the mitochondrial matrix for 48 h. A transition to its active (fluorescent) form is achieved by photoisomerization with a two-photon laser (750 nm) to give a 375-nm photon equivalence at the focal plane. This allows for selective photoconversion of areas as small as 0.5 um2 with a thickness of less than 0.5 um. In the absence of photoconversion, PA-GFPmt protein molecules remained stable in their pre-converted form. The presence of pre-converted PA-GFPmt was detected with high-intensity excitation at 488 nm (25-μW laser set at 1%) in combination with a fully opened pinhole. Spatially precise laser excitation can be used to label individual segments of the mitochondrial network at a time. The extent that photoconverted PAGFPmt is able to travel within a mitochondrion can be measured in order to quantify the size distribution of mitochondrial populations (Molina et. al., in press).

Confocal microscopy was performed on live cells in glass slide-bottomed dishes (MatTek, Ashland, Mass.) with a Zeiss LSM 510 Meta microscope with a plan apochromat 100× (numerical aperture 1.4) oil immersion objective. Three configurations were set using the multitrack mode. One for detection of the pre-converted PAGFP (higher 488 nm intensity), a second for photoconversion (750 nm with 2P laser), and a third for recording photoconverted PAGFP (low intensity 488 nm). Red-emitting TMRE was excited with a 1-mW, 543 nm helium/neon laser set at 0.3%, and emission was recorded through a BP 650 to 710 nm filter. Photoconverted PA-GFPmt protein was excited with a 25-mW, 488-nm argon laser set between 0.2%-0.5%. Emission was recorded through a BP 500 to 550 nm filter.

PAGFPmt can be similarly used to monitor and quantify networking activity in a whole cell. By photoconverting PAGFPmt in a subpopulation of mitochondria, the spread of photo-converted mtPAGFP signal throughout a cell via fusion and fission events and by mitochondrial movement as well has been observed. Fusion events not only lead to the spread of the photoconverted mtPAGFP across the networking population; it also leads to a dilution in the concentration of photoconverted molecules. This is translated into a reduction in the average GFP fluorescent intensity in the mitochondria that carry the photoconverted form. Therefore, by monitoring the decrease in PAGFPmt fluorescence intensity over time, fusion events that result in the transfer of PAGFPmt between mitochondria can be distinguished from the spread of PAGFPmt due to mitochondrial movement alone. This type of analysis can be used to compare the rate of mitochondrial dynamics between cells and due to various treatments. For example, it has been reported that mitochondrial fusion is halted in pancreatic beta cells with exposure to toxic nutrient levels (Molina et. al., in press).

The size of the mitochondrial subpopulation to be photoconverted should be kept constant if the user wishes to compare the rate of fusion between different conditions or cells. Photoconverting larger subpopulations will lead to shorter equilibration times. Two numerical values can be used to quantify the rate of mitochondrial dynamics;

The extent of dilution after a specified period of time (30 minutes or 1 hour)

Time to steady state (Equilibration time), defined by time after which no further dilution is measured.

Although the size of the area of photoconversion can be kept constant by using the same zoom value for activation, the number of mitochondria and size of the photoconverted population can still vary. This is due to the ability of matrix targeted GFP molecules to diffuse freely through any mitochondria with interconnected lumen and variations in the density of mitochondria. It has been found that with INS1 cells, activating an area that is 20% of the total cell area with 2P laser will provide an average equilibration time of around 45 minutes.

The same laser settings used for the monitoring of single mitochondria can be used for activating subpopulations. However, it is important to ensure that the 2-photon laser intensity is sufficient to photoconvert GFP while leaving the TMRE signal intact. The loss of TMRE fluorescence is indicative of phototoxicity and mitochondrial depolarization.

For some experiments, a Coherent Mira 900 femto second laser (Santa Clara, Calif.) was used. It was determined the minimum intensity and duration of laser exposure that initiated changes in $\Delta\Psi\mu$ and/or mitochondrial morphology in cells treated with TMRE. The parameters utilized in the reported experiments were well below these thresholds. To determine the safety limits of 2-Photon laser stimulation in INS1 cells, excitation was delivered over a wide range of intensities and durations. Excitation for 600 milliseconds/µm2 at 1 mW laser intensity at the objective was found to be the threshold dosage for INS1 and COST cells above which a reduction in mitochondrial membrane potential can be observed. All subsequent experiments using 2-photon illumination were conducted with duration of 150 ms/µm2 and an intensity of 1 mW. Due to variability in laser output, it is suggested that the user determine these values for the particular system being used. These intensity values can be used as a starting point and fine tuned.

It is sufficient to collect 6 images from different focal planes at each time point (this is compared to 20 images or more that would be required for 3D reconstruction) because the extent of fusion activity is derived from the dilution of the photoconverted PAGFP. After photoconversion, a z-stack of 6 images is collected every 5 minutes for 50 minutes. This can be adjusted to ensure that photobleaching or phototoxicity does not reduce the cellular PAGFP or TMRE fluorescent intensity. It is conceivable that PAGFPmt bleaching may contribute to a decrease in PAGFPmt signal over time. This would present an artifact in the analysis and quantification of PAGFPmt dilution. When fusion is inhibited, the PAGFPmt intensity/(pixel area) remains stable over 50 minutes. For this measurement pixel area is defined as the total area of photoconverted PAGFP. Without fusion and dilution of PAGFPmt, there is no bleaching due to repeated excitation and no loss of fluorescence intensity over a period of 50 minutes.

Monitoring the dilution of photoconverted mtPAGFP is an efficient way of quantification the sharing of GFP between mitochondria. Theoretically, when one mitochondrion carrying a matrix targeted photoconverted mtPAGFP fuses with another, the number of photoconverted molecules equilibrates between the two units and each ends up with half, causing a decrease in fluorescence intensity.

Quantification of fusion was performed using Metamorph (Molecular Devices CA) by measuring the average fluorescence intensity (FI) of the mitochondria that became PAGFPmt positive. The procedure involved first the elimination of non-mitochondrial pixels from the green (mtPAGFP) image followed by the measurement of green FI from mitochondria that were mtPAGFP positive.

Prior to measuring FI, an "Integrated Morphometry Analysis" function was used designed for these experiments in order to extract TMRE (or dsRed) positive structures that were larger than 10 pixels. These areas were interpreted as mitochondria, and their mtPAGFP was recorded. This procedure enabled the selection of mitochondrial structures from which mtPAGFP was measured using very low threshold levels in the green channel (approximately 10% of the image average intensity) assuring that over 90% of the mitochondrial pixels were included for analysis. It was verified that all intensity measurements were below saturation.

A low threshold (~10%) was applied to the green channel to identify the mtPAGFP positive mitochondria. Average FI (mtPAGFP) was measured from thresholded areas using Region Measurement. To set the threshold level, a test-threshold function first measured the average green FI of the mitochondria. The lower (inclusive) threshold was set at two thirds of this average. An upper threshold was not necessary since saturated images were carefully avoided during collection.

The FI values of PAGFPmt at each time point were normalized to the GFP FI value immediately after photoconversion and then fitted to a hyperbolic function:

$$F(t)=1-F\text{plateau}*t/(t+T50)$$

F and Fplateau denote fluorescent intensity (FI) at time t and in the plateau phase. T50 denote the time interval to a 50% decrease in normalized GFP FI ([1−Fplateau]/2). All fitting procedures and statistical tests were conducted using Kaleida-Graph software (Synergy Software, Reading, Pa.). Paired student's T-tests were performed to calculate statistical significance.

Using colocalization as a metric for quantification is problematic for a number of reasons. The decrease in GFP intensity with each fusion event is so prominent that it affects the perceived colocalization and confounds the results. It has been found that at later time points, the GFP intensity can become so weak that its colocalization with red pixels becomes unreliable. With photoconversion of 10-20% of the cell area, it is typically found that the GFP intensity at equilibrium is on average 60% lower compared to the beginning of the trial. In addition, in order to perform the colocalization analysis, it is necessary to scan an interlaced z-series through the cell. This is because fusion events can occur in any orientation. Higher rates of image acquisition should be avoided in order to prevent artifacts caused by photobleaching. GFP intensity dilution can report fusion events occurring outside of the focal plane.

There are a number of sources for potential artifacts that will lead to errors in the calculation of mitochondrial fusion measurements. This section will address these concerns and discuss ways to avoid these problems. It should be noted that any values for settings provided are for reference only and have only been tested on our system. The optimal settings may differ between systems, even from the same manufacturer.

Photoconversion of PAGFPmt into its fluorescent form requires careful calibration of the 2-photon laser intensity. This potential problem has been addressed in detail in the photoconversion section earlier in this manuscript. It has been observed that high 2-photon laser intensity can damage mitochondria and cause instability of $\Delta\Psi$ as well as permanent depolarization. This could confound measurements of mitochondrial fusion rates because depolarized mitochondria are unable to undergo fusion. By using TMRE to co-stain mitochondria in the PAGFPmt fusion assay, it is possible to monitor if the photoconversion event itself caused depolarization of mitochondria. In order to determine the correct laser parameters to use for PAGFPmt photoconversion, increasing doses of laser intensity must be tested in order to determine if the TMRE fluorescence intensity is affected. It is important to consider that in order to use such low photoconversion stimuli, it is necessary to have sufficient expression of mitochondrial PAGFPmt. With the described lentiviral delivery system, it has been found that increases in dosage of virus for transduction correlates with greater expression efficiency.

During image acquisition, it is essential to carefully monitor the images for the effects of photobleaching or saturation. Photobleaching occurs when the 488 nM excitation laser is too strong. This can confound the measurements of PAGFPmt dilution and overestimate the level of mitochondrial fusion.

To determine the laser intensity that does not cause bleaching, PAGFPmt intensity should be monitored over time in a system where mitochondrial fusion is blocked. It has been shown that MEF cells lacking MFN1 have mitochondria that are fragmented and unable to undergo fusion. These cells do not exhibit dilution of the mitochondrial PAGFPmt signal over time. It has been found that INS1 cells treated with high levels of fatty acid and glucose also exhibit mitochondrial fragmentation and generate a non-fusing mitochondrial sub-population (Molina et. al., in press). Using this system, it has been possible to show that the image acquisition protocol described herein does not cause photobleaching as reported by a photoconverted PAGFPmt signal that remains stable for the duration of the recording, up to 2 hours. Alternatively, if non-fusing condition can not be reached, the whole cell mtPAGFP FI should be monitored over time. When appropriate intensity is used in the 488 nm laser, spreading of mtPAGFP signal should not result in the reduction of whole cell mtPAGFP FI. This can be measured by dividing the GFP fluorescence by the entire pixel area of the cell. On a Zeiss LSM 510 system, it is found that using a 25 mW 488 nM argon laser set at 0.2%-0.5% does not cause photobleaching even when 6 image z-stacks are obtained every 5 minutes for a recording time of one hour.

PAGFPmt fluorescence saturation is also problematic because it can significantly limit the dynamic range of the fluorescence intensity curve. This would cause some fusion events, especially early in the recording time frame to go unrecognized. In addition to exceedingly strong 488 nM excitation, high gain settings for the image collection CCD camera are a likely culprit for saturation issues. Using the image acquisition software, it is important to ensure that the PAGFPmt image is not saturated after photoconversion to its fluorescent form.

For image analysis, it is necessary to set a lower inclusive threshold in order to define which pixels are to be included in the quantification of intensity over time. The parameters that have been chosen for the determination of this threshold have been described earlier. Careful consideration must be applied when choosing this threshold value because picking one that is too low will introduce noise from non mitochondrial fluorescence and one that is too high will limit the bottom end of the PAGFPmt intensity dynamic range. In order to prevent this issue, it is necessary to ensure that the chosen threshold value is suitable not only at time 0, right after photoconversion, but also at the end time point. It is important to make sure that pixels are not lost towards the end of the recording time, when equilibrium has been reached.

I claim:

1. A compound:

or a pharmaceutically acceptable salt thereof.

2. A pharmaceutical composition comprising a compound of claim 1 or a pharmaceutically acceptable salt thereof and a pharmaceutically acceptable excipient.

* * * * *

SEQUENCE LISTING

<160> NUMBER OF SEQ ID NOS: 21

<210> SEQ ID NO 1
<211> LENGTH: 6
<212> TYPE: PRT
<213> ORGANISM: Homo sapiens

<400> SEQUENCE: 1

Lys Thr Lys Glu Gly Val
1               5

<210> SEQ ID NO 2
<211> LENGTH: 20
<212> TYPE: DNA
<213> ORGANISM: Artificial Sequence

```
<220> FEATURE:
<223> OTHER INFORMATION: Chemically synthesized

<400> SEQUENCE: 2
aacggatttg gtcgtattgg                                                    20

<210> SEQ ID NO 3
<211> LENGTH: 20
<212> TYPE: DNA
<213> ORGANISM: Artificial Sequence
<220> FEATURE:
<223> OTHER INFORMATION: Chemically synthesized

<400> SEQUENCE: 3
gctcctggaa gatggtgatg                                                    20

<210> SEQ ID NO 4
<211> LENGTH: 20
<212> TYPE: DNA
<213> ORGANISM: Artificial Sequence
<220> FEATURE:
<223> OTHER INFORMATION: Chemically synthesized

<400> SEQUENCE: 4
aagccatcaa ggtgatgagg                                                    20

<210> SEQ ID NO 5
<211> LENGTH: 20
<212> TYPE: DNA
<213> ORGANISM: Artificial Sequence
<220> FEATURE:
<223> OTHER INFORMATION: Chemically synthesized

<400> SEQUENCE: 5
ggtcacacgc cacataacag                                                    20

<210> SEQ ID NO 6
<211> LENGTH: 22
<212> TYPE: DNA
<213> ORGANISM: Artificial Sequence
<220> FEATURE:
<223> OTHER INFORMATION: Chemically synthesized

<400> SEQUENCE: 6
atcacctagt ccaccactgt cc                                                 22

<210> SEQ ID NO 7
<211> LENGTH: 19
<212> TYPE: DNA
<213> ORGANISM: Artificial Sequence
<220> FEATURE:
<223> OTHER INFORMATION: Chemically synthesized

<400> SEQUENCE: 7
gtatctacca tccgccatc                                                     19

<210> SEQ ID NO 8
<211> LENGTH: 20
<212> TYPE: DNA
<213> ORGANISM: Artificial Sequence
<220> FEATURE:
<223> OTHER INFORMATION: Chemically synthesized

<400> SEQUENCE: 8
ttatgtcatg tcgggtgtgg                                                    20
```

```
<210> SEQ ID NO 9
<211> LENGTH: 19
<212> TYPE: DNA
<213> ORGANISM: Artificial Sequence
<220> FEATURE:
<223> OTHER INFORMATION: Chemically synthesized

<400> SEQUENCE: 9
acaggtgtag ggctctgtg                                                    19

<210> SEQ ID NO 10
<211> LENGTH: 20
<212> TYPE: DNA
<213> ORGANISM: Artificial Sequence
<220> FEATURE:
<223> OTHER INFORMATION: Chemically synthesized

<400> SEQUENCE: 10
gaggaaagca gaggtgatgc                                                   20

<210> SEQ ID NO 11
<211> LENGTH: 20
<212> TYPE: DNA
<213> ORGANISM: Artificial Sequence
<220> FEATURE:
<223> OTHER INFORMATION: Chemically synthesized

<400> SEQUENCE: 11
gaggcaacct gaccagaaac                                                   20

<210> SEQ ID NO 12
<211> LENGTH: 20
<212> TYPE: DNA
<213> ORGANISM: Artificial Sequence
<220> FEATURE:
<223> OTHER INFORMATION: Chemically synthesized

<400> SEQUENCE: 12
ggttgagaaa ggcgagacac                                                   20

<210> SEQ ID NO 13
<211> LENGTH: 20
<212> TYPE: DNA
<213> ORGANISM: Artificial Sequence
<220> FEATURE:
<223> OTHER INFORMATION: Chemically synthesized

<400> SEQUENCE: 13
tgaggacacc caagcaagac                                                   20

<210> SEQ ID NO 14
<211> LENGTH: 20
<212> TYPE: DNA
<213> ORGANISM: Artificial Sequence
<220> FEATURE:
<223> OTHER INFORMATION: Chemically synthesized

<400> SEQUENCE: 14
gaacatggtg ctggtttcct                                                   20

<210> SEQ ID NO 15
<211> LENGTH: 20
<212> TYPE: DNA
<213> ORGANISM: Artificial Sequence
<220> FEATURE:
<223> OTHER INFORMATION: Chemically synthesized

<400> SEQUENCE: 15
```

```
catccagggt actgggctaa                                                   20

<210> SEQ ID NO 16
<211> LENGTH: 20
<212> TYPE: DNA
<213> ORGANISM: Artificial Sequence
<220> FEATURE:
<223> OTHER INFORMATION: Chemically synthesized

<400> SEQUENCE: 16
agggacaacc ctaacacgac                                                   20

<210> SEQ ID NO 17
<211> LENGTH: 20
<212> TYPE: DNA
<213> ORGANISM: Artificial Sequence
<220> FEATURE:
<223> OTHER INFORMATION: Chemically synthesized

<400> SEQUENCE: 17
agcaggagaa agacgaggac                                                   20

<210> SEQ ID NO 18
<211> LENGTH: 20
<212> TYPE: DNA
<213> ORGANISM: Artificial Sequence
<220> FEATURE:
<223> OTHER INFORMATION: Chemically synthesized

<400> SEQUENCE: 18
gaagctgcaa cacagactgc                                                   20

<210> SEQ ID NO 19
<211> LENGTH: 20
<212> TYPE: DNA
<213> ORGANISM: Artificial Sequence
<220> FEATURE:
<223> OTHER INFORMATION: Chemically synthesized

<400> SEQUENCE: 19
ttgaatgact agccgggaac                                                   20

<210> SEQ ID NO 20
<211> LENGTH: 20
<212> TYPE: DNA
<213> ORGANISM: Artificial Sequence
<220> FEATURE:
<223> OTHER INFORMATION: Chemically synthesized

<400> SEQUENCE: 20
gcatggccat cttctctttc                                                   20

<210> SEQ ID NO 21
<211> LENGTH: 20
<212> TYPE: DNA
<213> ORGANISM: Artificial Sequence
<220> FEATURE:
<223> OTHER INFORMATION: Chemically synthesized

<400> SEQUENCE: 21
tggatgggac tccatagctc                                                   20
```